US012765898B2

(12) United States Patent
Lambert et al.

(10) Patent No.: US 12,765,898 B2
(45) Date of Patent: Oct. 20, 2026

(54) INTRAVASCULAR LITHOTRIPSY CATHETERS WITH LATERALLY MOVABLE AND POSITIONABLE EMITTERS

(71) Applicant: Shockwave Medical, Inc., Santa Clara, CA (US)

(72) Inventors: Christopher M. Lambert, Hayward, CA (US); Nancy P. Nguyen, San Jose, CA (US)

(73) Assignee: SHOCKWAVE MEDICAL, INC., Santa Clara, CA (US)

( * ) Notice: Subject to any disclaimer, the term of this patent is extended or adjusted under 35 U.S.C. 154(b) by 0 days.

(21) Appl. No.: 18/810,877

(22) Filed: Aug. 21, 2024

(65) Prior Publication Data

US 2025/0064470 A1 Feb. 27, 2025

Related U.S. Application Data

(60) Provisional application No. 63/534,711, filed on Aug. 25, 2023.

(51) Int. Cl.
*A61B 17/22* (2006.01)

(52) U.S. Cl.
CPC .................. *A61B 17/22022* (2013.01); *A61B 2017/22061* (2013.01); *A61B 2017/22062* (2013.01)

(58) Field of Classification Search
CPC ............ A61B 2017/22061; A61B 2017/22062
See application file for complete search history.

(56) References Cited

U.S. PATENT DOCUMENTS 2,916,647 A 12/1959 George
3,412,288 A 11/1968 Ostrander
(Continued)

FOREIGN PATENT DOCUMENTS

AU 2009313507 B2 11/2014
AU 2013284490 B2 5/2018
(Continued)

OTHER PUBLICATIONS

International Search Report and Written Opinion received for International Patent Application No. PCT/US2024/043439, mailed on Dec. 9, 2024, 12 pages.
(Continued)

*Primary Examiner* — William J Levicky
*Assistant Examiner* — Jessandra F Hough
(74) *Attorney, Agent, or Firm* — Morrison & Foerster LLP

(57) ABSTRACT

A shock wave catheter for performing intravascular lithotripsy (IVL) is provided. The catheter includes an elongated tube having a central longitudinal axis, an enclosure sealed to the distal end of the elongated tube, and an adjustable emitter assembly disposed within the enclosure. The emitter assembly includes at least one laterally moveable or positionable shock wave generating emitter that, in a first configuration, is closer to the central longitudinal axis of the catheter, and, in a second configuration, is farther from the central longitudinal axis than in the first position. Various embodiments include support structures for the emitters, multiple balloons for positioning the emitters, helical ribbons, angled emitter ports, and other exemplary features for moving and/or positioning the emitters. Systems and methods for treating lesions in a body lumen are also provided herein.

80 Claims, 22 Drawing Sheets

(56) References Cited

U.S. PATENT DOCUMENTS 3,413,976 A 12/1968 Roze
3,524,101 A 8/1970 Barbini
3,583,766 A 6/1971 Padberg
3,785,382 A 1/1974 Schmidt-Kloiber et al.
3,902,499 A 9/1975 Shene
3,942,531 A 3/1976 Hoff et al.
4,027,674 A 6/1977 Tessler et al.
4,030,505 A 6/1977 Tessler
4,445,509 A 5/1984 Auth
4,662,126 A 5/1987 Malcolm
4,662,375 A 5/1987 Hepp et al.
4,671,254 A 6/1987 Fair
4,685,458 A 8/1987 Leckrone
4,741,405 A 5/1988 Moeny et al.
4,809,682 A 3/1989 Forssmann et al.
4,813,934 A 3/1989 Engelson et al.
4,878,495 A 11/1989 Grayzei
4,890,603 A 1/1990 Filler
4,900,303 A 2/1990 Lemelson
4,990,134 A 2/1991 Auth
4,994,032 A 2/1991 Sugiyama et al.
5,009,232 A 4/1991 Hassler et al.
5,046,503 A 9/1991 Schneiderman
5,057,103 A 10/1991 Davis
5,057,106 A 10/1991 Kasevich et al.
5,061,240 A 10/1991 Cherian
5,078,717 A 1/1992 Parins et al.
5,102,402 A 4/1992 Dror et al.
5,103,804 A 4/1992 Abele et al.
5,116,227 A 5/1992 Levy
5,152,767 A 10/1992 Sypal et al.
5,152,768 A 10/1992 Bhatta
5,154,722 A 10/1992 Filip et al.
5,176,675 A 1/1993 Watson et al.
5,195,508 A 3/1993 Muller et al.
5,245,988 A 9/1993 Einars et al.
5,246,447 A 9/1993 Rosen et al.
5,254,121 A 10/1993 Manevitz et al.
5,281,231 A 1/1994 Rosen et al.
5,295,958 A 3/1994 Shturman
5,304,134 A 4/1994 Kraus et al.
5,321,715 A 6/1994 Trost
5,324,255 A 6/1994 Passafaro et al.
5,336,234 A 8/1994 Vigil et al.
5,362,309 A 11/1994 Carter
5,364,393 A 11/1994 Auth et al.
5,368,591 A 11/1994 Lennox et al.
5,395,335 A 3/1995 Jang
5,417,208 A 5/1995 Winkler
5,425,735 A 6/1995 Rosen et al.
5,454,809 A 10/1995 Janssen
5,460,616 A 10/1995 Weinstein et al.
5,472,406 A 12/1995 de la Torre et al.
5,582,578 A 12/1996 Zhong et al.
5,584,843 A 12/1996 Wulfman et al.
5,603,731 A 2/1997 Whitney
5,609,606 A 3/1997 O'Boyle
5,662,590 A 9/1997 de la Torre et al.
5,709,676 A 1/1998 Alt
5,846,218 A 12/1998 Brisken et al.
5,891,089 A 4/1999 Katz et al.
5,893,840 A 4/1999 Hull et al.
5,931,805 A 8/1999 Brisken
6,007,530 A 12/1999 Dornhofer et al.
6,033,371 A 3/2000 Torre et al.
6,056,722 A 5/2000 Jayaraman
6,080,119 A 6/2000 Schwarze et al.
6,083,232 A 7/2000 Cox
6,090,104 A 7/2000 Webster et al.
6,113,560 A 9/2000 Simnacher
6,132,444 A 10/2000 Shturman et al.
6,146,358 A 11/2000 Rowe
6,186,963 B1 2/2001 Schwarze et al.
6,210,408 B1 4/2001 Chandrasekaran et al.
6,215,734 B1 4/2001 Moeny et al.
6,217,531 B1 4/2001 Reitmajer
6,267,747 B1 7/2001 Samson et al.
6,277,138 B1 8/2001 Levinson et al.
6,287,272 B1 9/2001 Brisken et al.
6,352,535 B1 3/2002 Lewis et al.
6,364,894 B1 4/2002 Healy et al.
6,367,203 B1 4/2002 Graham et al.
6,371,971 B1 4/2002 Tsugita et al.
6,398,792 B1 6/2002 O'Connor
6,406,486 B1 6/2002 de la Torre et al.
6,440,124 B1 8/2002 Esch et al.
6,488,673 B1 * 12/2002 Laufer .................. A61M 29/02 604/516
6,494,890 B1 12/2002 Shturman et al.
6,514,203 B2 2/2003 Bukshpan
6,524,251 B2 2/2003 Rabiner et al.
6,589,253 B1 7/2003 Cornish et al.
6,607,003 B1 8/2003 Wilson
6,638,246 B1 10/2003 Naimark et al.
6,652,547 B2 11/2003 Rabiner et al.
6,666,834 B2 12/2003 Restle et al.
6,689,089 B1 2/2004 Tiedtke et al.
6,736,784 B1 5/2004 Menne et al.
6,740,081 B2 5/2004 Hilal
6,755,821 B1 6/2004 Fry
6,939,320 B2 9/2005 Lennox
6,989,009 B2 1/2006 Lafontaine
7,066,904 B2 6/2006 Rosenthal et al.
7,087,061 B2 8/2006 Chernenko et al.
7,241,295 B2 7/2007 Maguire
7,309,324 B2 12/2007 Hayes et al.
7,389,148 B1 6/2008 Morgan
7,505,812 B1 3/2009 Eggers et al.
7,569,032 B2 8/2009 Naimark et al.
7,850,685 B2 12/2010 Kunis et al.
7,853,332 B2 12/2010 Olsen et al.
7,873,404 B1 1/2011 Patton
7,951,111 B2 5/2011 Drasler et al.
8,162,859 B2 4/2012 Schultheiss et al.
8,177,801 B2 5/2012 Kallok et al.
8,353,923 B2 1/2013 Shturman
8,556,813 B2 10/2013 Cioanta et al.
8,574,247 B2 11/2013 Adams et al.
8,728,091 B2 5/2014 Hakala et al.
8,747,416 B2 6/2014 Hakala et al.
8,888,788 B2 11/2014 Hakala et al.
8,956,371 B2 2/2015 Hawkins et al.
8,956,374 B2 2/2015 Hawkins et al.
9,005,216 B2 4/2015 Hakala et al.
9,011,462 B2 4/2015 Adams et al.
9,011,463 B2 4/2015 Adams et al.
9,044,618 B2 6/2015 Hawkins et al.
9,044,619 B2 6/2015 Hawkins et al.
9,072,534 B2 7/2015 Hakala et al.
9,138,249 B2 9/2015 Adams et al.
9,198,825 B2 12/2015 Katragadda et al.
9,333,000 B2 5/2016 Hakala et al.
9,421,025 B2 8/2016 Hawkins et al.
9,433,428 B2 9/2016 Hakala et al.
9,522,012 B2 12/2016 Adams
9,642,673 B2 5/2017 Adams et al.
9,993,292 B2 6/2018 Adams et al.
10,039,561 B2 8/2018 Adams et al.
10,118,015 B2 11/2018 De La Rama et al.
10,149,690 B2 12/2018 Hawkins et al.
10,154,799 B2 12/2018 Van Der Weide et al.
10,159,505 B2 12/2018 Hakala et al.
10,206,698 B2 2/2019 Hakala et al.
10,226,265 B2 3/2019 Ku et al.
10,357,264 B2 7/2019 Kat-Kouy
10,517,620 B2 12/2019 Adams
10,517,621 B1 12/2019 Adams
10,555,744 B2 2/2020 Nguyen et al.
10,682,178 B2 6/2020 Adams et al.
10,702,293 B2 7/2020 Hawkins et al.
10,709,462 B2 7/2020 Nguyen et al.
10,959,743 B2 3/2021 Adams et al.
10,966,737 B2 4/2021 Nguyen
10,973,538 B2 4/2021 Hakala et al.

(56) References Cited

U.S. PATENT DOCUMENTS

| | | | |
|---|---|---|---|
| 10,980,553 | B2 | 4/2021 | Or et al. |
| 11,000,299 | B2 | 5/2021 | Hawkins et al. |
| 11,076,874 | B2 | 8/2021 | Hakala et al. |
| 11,337,713 | B2 | 5/2022 | Nguyen et al. |
| 11,432,834 | B2 | 9/2022 | Adams |
| 11,478,261 | B2 | 10/2022 | Nguyen |
| 11,534,187 | B2 | 12/2022 | Bonutti |
| 11,596,423 | B2 | 3/2023 | Nguyen et al. |
| 11,596,424 | B2 | 3/2023 | Hakala et al. |
| 11,622,780 | B2 | 4/2023 | Nguyen et al. |
| 11,696,799 | B2 | 7/2023 | Adams et al. |
| 11,766,271 | B2 | 9/2023 | Adams |
| 11,771,449 | B2 | 10/2023 | Adams et al. |
| 11,786,704 | B2 | 10/2023 | Stapleton et al. |
| 12,035,932 | B1 | 7/2024 | Nunes et al. |
| 12,048,821 | B2 | 7/2024 | Kawwas et al. |
| 12,402,899 | B2 | 9/2025 | Hasenberg et al. |
| 12,433,620 | B2 | 10/2025 | Rond et al. |
| 2001/0044596 | A1 | 11/2001 | Jaafar |
| 2002/0045890 | A1 | 4/2002 | Celliers et al. |
| 2002/0082553 | A1 | 6/2002 | Duchamp |
| 2002/0133150 | A1 | 9/2002 | Whayne et al. |
| 2002/0177889 | A1 | 11/2002 | Brisken et al. |
| 2003/0004434 | A1 | 1/2003 | Greco et al. |
| 2003/0176873 | A1 | 9/2003 | Chernenko et al. |
| 2003/0229370 | A1 | 12/2003 | Miller |
| 2004/0006333 | A1 | 1/2004 | Arnold et al. |
| 2004/0010249 | A1 | 1/2004 | Truckai et al. |
| 2004/0044308 | A1 | 3/2004 | Naimark et al. |
| 2004/0097963 | A1 | 5/2004 | Seddon |
| 2004/0097996 | A1 | 5/2004 | Rabiner et al. |
| 2004/0162508 | A1 | 8/2004 | Uebelacker |
| 2004/0249401 | A1 | 12/2004 | Rabiner et al. |
| 2004/0254570 | A1 | 12/2004 | Hadjicostis et al. |
| 2005/0015953 | A1 | 1/2005 | Keidar |
| 2005/0021013 | A1 | 1/2005 | Visuri et al. |
| 2005/0059965 | A1 | 3/2005 | Eberl et al. |
| 2005/0075662 | A1 | 4/2005 | Pedersen et al. |
| 2005/0090888 | A1 | 4/2005 | Hines et al. |
| 2005/0113722 | A1 | 5/2005 | Schultheiss |
| 2005/0113822 | A1 | 5/2005 | Fuimaono et al. |
| 2005/0171527 | A1 | 8/2005 | Bhola |
| 2005/0228372 | A1 | 10/2005 | Truckai et al. |
| 2005/0245866 | A1 | 11/2005 | Azizi |
| 2005/0251131 | A1 | 11/2005 | Lesh |
| 2006/0004286 | A1 | 1/2006 | Chang et al. |
| 2006/0069424 | A1 | 3/2006 | Acosta et al. |
| 2006/0074484 | A1 | 4/2006 | Huber |
| 2006/0184076 | A1 | 8/2006 | Gill et al. |
| 2006/0190022 | A1 | 8/2006 | Beyar et al. |
| 2006/0221528 | A1 | 10/2006 | Li et al. |
| 2007/0016112 | A1 | 1/2007 | Schultheiss et al. |
| 2007/0088380 | A1 | 4/2007 | Hirszowicz et al. |
| 2007/0129667 | A1 | 6/2007 | Tiedtke et al. |
| 2007/0156129 | A1 | 7/2007 | Kovalcheck |
| 2007/0239082 | A1 | 10/2007 | Schultheiss et al. |
| 2007/0239253 | A1 | 10/2007 | Jagger et al. |
| 2007/0244423 | A1 | 10/2007 | Zumeris et al. |
| 2007/0250052 | A1 | 10/2007 | Wham |
| 2007/0255270 | A1 | 11/2007 | Carney |
| 2007/0282301 | A1 | 12/2007 | Segalescu et al. |
| 2007/0299481 | A1 | 12/2007 | Syed et al. |
| 2008/0097251 | A1 | 4/2008 | Babaev |
| 2008/0188913 | A1 | 8/2008 | Stone et al. |
| 2009/0041833 | A1 | 2/2009 | Bettinger et al. |
| 2009/0227992 | A1 | 9/2009 | Nir et al. |
| 2009/0230822 | A1 | 9/2009 | Kushculey et al. |
| 2009/0247945 | A1 | 10/2009 | Levit et al. |
| 2009/0254114 | A1 | 10/2009 | Hirszowicz et al. |
| 2009/0299447 | A1 | 12/2009 | Jensen et al. |
| 2010/0016862 | A1 | 1/2010 | Hawkins et al. |
| 2010/0036294 | A1 | 2/2010 | Mantell et al. |
| 2010/0094209 | A1 | 4/2010 | Drasler et al. |
| 2010/0114020 | A1 | 5/2010 | Hawkins et al. |
| 2010/0114065 | A1 | 5/2010 | Hawkins et al. |
| 2010/0121322 | A1 | 5/2010 | Swanson |
| 2010/0179424 | A1 | 7/2010 | Warnking et al. |
| 2010/0286709 | A1 | 11/2010 | Diamant et al. |
| 2010/0305565 | A1 | 12/2010 | Truckai et al. |
| 2011/0034832 | A1 | 2/2011 | Cioanta et al. |
| 2011/0118634 | A1 | 5/2011 | Golan |
| 2011/0208185 | A1 | 8/2011 | Diamant et al. |
| 2011/0257523 | A1 | 10/2011 | Hastings et al. |
| 2011/0295227 | A1 | 12/2011 | Hawkins et al. |
| 2012/0071889 | A1 | 3/2012 | Mantell et al. |
| 2012/0095461 | A1 | 4/2012 | Herscher et al. |
| 2012/0116289 | A1 | 5/2012 | Hawkins et al. |
| 2012/0143177 | A1 | 6/2012 | Avitall et al. |
| 2012/0157991 | A1 | 6/2012 | Christian |
| 2012/0203255 | A1 | 8/2012 | Hawkins et al. |
| 2012/0253358 | A1 | 10/2012 | Golan et al. |
| 2013/0030431 | A1 | 1/2013 | Adams |
| 2013/0041355 | A1 | 2/2013 | Heeren et al. |
| 2013/0116714 | A1 | 5/2013 | Adams et al. |
| 2013/0123694 | A1 | 5/2013 | Subramaniyan et al. |
| 2013/0150874 | A1 | 6/2013 | Kassab |
| 2013/0253622 | A1 | 9/2013 | Hooven |
| 2014/0046229 | A1 | 2/2014 | Hawkins et al. |
| 2014/0163592 | A1* | 6/2014 | Hawkins .......... A61B 17/22012 606/159 |
| 2014/0214061 | A1 | 7/2014 | Adams et al. |
| 2015/0320432 | A1 | 11/2015 | Adams |
| 2016/0135828 | A1 | 5/2016 | Hawkins et al. |
| 2016/0151081 | A1 | 6/2016 | Adams et al. |
| 2016/0324534 | A1 | 11/2016 | Hawkins et al. |
| 2017/0135709 | A1 | 5/2017 | Nguyen et al. |
| 2017/0311965 | A1 | 11/2017 | Adams |
| 2021/0085347 | A1 | 3/2021 | Phan et al. |
| 2021/0085383 | A1 | 3/2021 | Vo et al. |
| 2021/0338258 | A1 | 11/2021 | Hawkins et al. |
| 2022/0015785 | A1 | 1/2022 | Hakala et al. |
| 2022/0183738 | A1 | 6/2022 | Flores et al. |
| 2022/0240958 | A1 | 8/2022 | Nguyen et al. |
| 2022/0287732 | A1* | 9/2022 | Anderson .......... A61M 25/104 |
| 2023/0043475 | A1 | 2/2023 | Adams |
| 2023/0107690 | A1 | 4/2023 | Nguyen |
| 2023/0165598 | A1 | 6/2023 | Nguyen et al. |
| 2023/0293197 | A1 | 9/2023 | Nguyen et al. |
| 2023/0310073 | A1 | 10/2023 | Adams et al. |
| 2023/0329731 | A1 | 10/2023 | Hakala et al. |
| 2023/0355302 | A1 | 11/2023 | Achterhoff et al. |
| 2023/0380849 | A1 | 11/2023 | Adams et al. |
| 2024/0260982 | A1 | 8/2024 | Peterson |
| 2024/0285296 | A1 | 8/2024 | Vo |
| 2026/0069297 | A1 | 3/2026 | Moosavi et al. |

FOREIGN PATENT DOCUMENTS

| | | | |
|---|---|---|---|
| CA | 2104414 | A1 | 2/1995 |
| CN | 1204242 | A | 1/1999 |
| CN | 1269708 | A | 10/2000 |
| CN | 1942145 | A | 4/2007 |
| CN | 101043914 | A | 9/2007 |
| CN | 102057422 | A | 5/2011 |
| CN | 102271748 | A | 12/2011 |
| CN | 102355856 | A | 2/2012 |
| CN | 102765785 | A | 11/2012 |
| CN | 203564304 | U | 4/2014 |
| CN | 109674508 | A | 4/2019 |
| CN | 211094481 | U | 7/2020 |
| CN | 211705595 | U | 10/2020 |
| CN | 107550559 | B | 10/2021 |
| CN | 215228131 | U | 12/2021 |
| CN | 114831697 | A | 8/2022 |
| CN | 114983516 | A | 9/2022 |
| CN | 116058918 | A | 5/2023 |
| CN | 116269628 | A | 6/2023 |
| CN | 219166543 | U | 6/2023 |
| CN | 116492012 | A | 7/2023 |
| CN | 116831696 | A | 10/2023 |
| DE | 3038445 | A1 | 5/1982 |
| DE | 202006014285 | U1 | 12/2006 |
| EP | 0442199 | A2 | 8/1991 |
| EP | 0571306 | A1 | 11/1993 |

(56) References Cited

FOREIGN PATENT DOCUMENTS

| | | | |
|---|---|---|---|
| EP | 623360 | A1 | 11/1994 |
| EP | 0647435 | A1 | 4/1995 |
| EP | 2253884 | A1 | 11/2010 |
| EP | 2362798 | B1 | 4/2014 |
| EP | 4011304 | A1 | 6/2022 |
| EP | 3511047 | B1 | 3/2024 |
| GB | 2601761 | A | 6/2022 |
| JP | S62-099210 | U | 6/1987 |
| JP | S62-275446 | A | 11/1987 |
| JP | H03-63059 | A | 3/1991 |
| JP | H06-125915 | A | 5/1994 |
| JP | H07-47135 | A | 2/1995 |
| JP | H08-89511 | A | 4/1996 |
| JP | H10-99444 | A | 4/1998 |
| JP | H10-314177 | A | 12/1998 |
| JP | H10-513379 | A | 12/1998 |
| JP | 2002538932 | A | 11/2002 |
| JP | 2004081374 | A | 3/2004 |
| JP | 2004357792 | A | 12/2004 |
| JP | 2005501597 | A | 1/2005 |
| JP | 2005095410 | A | 4/2005 |
| JP | 2005515825 | A | 6/2005 |
| JP | 2006516465 | A | 7/2006 |
| JP | 2007289707 | A | 11/2007 |
| JP | 2007532182 | A | 11/2007 |
| JP | 2008506447 | A | 3/2008 |
| JP | 2011513694 | A | 4/2011 |
| JP | 2011520248 | A | 7/2011 |
| JP | 2011524203 | A | 9/2011 |
| JP | 2011528963 | A | 12/2011 |
| JP | 2012505050 | A | 3/2012 |
| JP | 2012508042 | A | 4/2012 |
| JP | 2015525657 | A | 9/2015 |
| JP | 2015528327 | A | 9/2015 |
| JP | 6029828 | B2 | 11/2016 |
| JP | 6081510 | B2 | 2/2017 |
| JP | 2022544651 | A | 10/2022 |
| KR | 20220072854 | A | 6/2022 |
| WO | WO-1989011307 | A1 | 11/1989 |
| WO | WO-1996024297 | A1 | 8/1996 |
| WO | WO-1999000060 | A1 | 1/1999 |
| WO | WO-1999002096 | A1 | 1/1999 |
| WO | WO-2000056237 | A2 | 9/2000 |
| WO | WO-2004069072 | A2 | 8/2004 |
| WO | WO-2005099594 | A1 | 10/2005 |
| WO | WO-2005102199 | A1 | 11/2005 |
| WO | WO-2006006169 | A2 | 1/2006 |
| WO | WO-2006127158 | A2 | 11/2006 |
| WO | WO-2007088546 | A2 | 8/2007 |
| WO | WO-2007149905 | A2 | 12/2007 |
| WO | WO-2009121017 | A1 | 10/2009 |
| WO | WO-2009126544 | A1 | 10/2009 |
| WO | WO-2009136268 | A1 | 11/2009 |
| WO | WO-2009152352 | A2 | 12/2009 |
| WO | WO-2010014515 | A2 | 2/2010 |
| WO | WO-2010054048 | A2 | 9/2010 |
| WO | WO-2011006017 | A1 | 1/2011 |
| WO | WO-2011094111 | A2 | 8/2011 |
| WO | WO-2011143468 | A2 | 11/2011 |
| WO | WO-2012025833 | A2 | 3/2012 |
| WO | WO-2013059735 | A1 | 4/2013 |
| WO | WO-2014025397 | A1 | 2/2014 |
| WO | WO-2014025620 | A1 | 2/2014 |
| WO | WO-2015017499 | A1 | 2/2015 |
| WO | WO-2019099218 | A1 | 5/2019 |
| WO | WO-2020048274 | A1 | 3/2020 |
| WO | WO-2021022849 | A1 | 2/2021 |
| WO | WO-2022166881 | A1 | 8/2022 |
| WO | WO-2022166883 | A1 | 8/2022 |
| WO | WO-2022166884 | A1 | 8/2022 |
| WO | WO-2024067823 | A1 | 4/2024 |
| WO | WO-2024118970 | A1 | 6/2024 |
| WO | WO-2025040948 | A1 | 2/2025 |

OTHER PUBLICATIONS

Unpublished U.S. Appl. No. 18/680,853, filed May 31, 2024, titled "Laser Intravasular Lithotripsy Device for Stenosis Calcified Lesions," (Copy not submitted herewith pursuant to the waiver of 37 C.F.R. § 1.98(a)(2)(iii)).

Unpublished U.S. Appl. No. 19/319,045, filed Sep. 4, 2025, titled "Shock Wave Catheter and Shock Wave Catheter System," (Copy not submitted herewith pursuant to the waiver of 37 C.F.R. § 1.98(a)(2)(iii)).

Bernava et al., (2022). "Lithotripsy of Calcified Aortic Valve Leaflets by a Novel Ultrasound Transcatheter-Based Device," Front. Cardiovasc. Med., 9:850393, 9 pages.

Fermi et al., (2021). "Trans-Catheter Double-Frequency Ultrasound Ablator for tThe Treatment of Aortic Valve Leaflets Calcification," Biomed J Sci & Tech Res, 33(4)25952-25957.

International Search Report and Written Opinion received for International Patent Application No. PCT/US2025/045094, mailed on Feb. 23, 2026, 18 pages.

International Search Report and Written Opinion received for International Patent Application No. PCT/US2025/045112, mailed on Feb. 13, 2026, 18 pages.

Perico et al., (2025). "A Novel Transcatheter Device to Treat Calcific Aortic Valve Stenosis: An Ex Vivo Study," Cardiovascular Engineering and Technology, 16:296-306.

Tiengo et al., (2022). "In Vitro Model for the Evaluation of Innovative Transcatheter Debridement Device (TDD): Pericardium-Based Scaffold and Stem Cells to Reproduce Calcificated Valves," Biomedicines, 10:2352, 12 pages.

* cited by examiner

INTRAVASCULAR LITHOTRIPSY CATHETERS WITH LATERALLY MOVABLE AND POSITIONABLE EMITTERS

PRIORITY

This application claims priority to U.S. Provisional Patent Application Ser. No. 63/534,711, filed Aug. 25, 2023.

FIELD OF THE DISCLOSURE

The present disclosure relates generally to the field of medical devices and methods, and more specifically to shock wave catheter devices for treating lesions in body lumens.

BACKGROUND

A wide variety of catheters have been developed for treating calcified lesions, such as calcified lesions in vasculature associated with arterial disease. For example, treatment systems for percutaneous coronary angioplasty or peripheral angioplasty use angioplasty balloons to dilate a calcified lesion and restore normal blood flow in a vessel. In these types of procedures, a catheter carrying a balloon is advanced into the vasculature along a guide wire until the balloon is aligned with calcified plaques. The balloon is then pressurized (normally to greater than 10 atm), causing the balloon to expand in the vessel to push calcified plaques back into the vessel wall and dilate occluded regions of vasculature.

More recently, the technique and treatment of intravascular lithotripsy (IVL) has been developed, which is an interventional procedure to modify calcified plaque in diseased arteries. The mechanism of plaque modification is through use of a catheter having one or more acoustic shock wave generating sources located within a liquid that can generate acoustic shock waves that modify the calcified plaque. IVL devices vary in design with respect to the energy source used to generate the acoustic shock waves, with two exemplary energy sources being electrohydraulic generation and laser generation.

For electrohydraulic generation of acoustic shock waves, a conductive solution (e.g., saline) may be contained within an enclosure that surrounds electrodes or can be flushed through a tube that surrounds the electrodes. The calcified plaque modification is achieved by creating acoustic shock waves within the catheter by an electrical discharge across the electrodes. This discharge creates one or more rapidly expanding vapor bubbles that generate the acoustic shock waves. These shock waves propagate radially outward and modify calcified plaque within the blood vessels. For laser generation of acoustic shock waves, a laser pulse is transmitted into and absorbed by a fluid within the catheter. This absorption process rapidly heats and vaporizes the fluid, thereby generating the rapidly expanding vapor bubble, as well as the acoustic shock waves that propagate outward and modify the calcified plaque. The acoustic shock wave intensity is higher if a fluid is chosen that exhibits strong absorption at the laser wavelength that is employed. These examples of IVL devices are not intended to be a comprehensive list of potential energy sources to create IVL shock waves.

The IVL process may be considered different from standard atherectomy procedures in that it cracks calcium but does not liberate the cracked calcium from the tissue. Hence, generally speaking, IVL should not require aspiration nor embolic protection. Further, due to the compliance of a normal blood vessel and non-calcified plaque, the shock waves produced by IVL do not modify the normal vessel or non-calcified plaque.

More specifically, catheters to deliver IVL therapy have been developed that include pairs of electrodes for electrohydraulically generating shock waves inside an angioplasty balloon. Shock wave devices can be particularly effective for treating calcified plaque lesions because the acoustic pressure from the shock waves can crack and disrupt lesions near the angioplasty balloon without harming the surrounding tissue. In these devices, a catheter is advanced over a guidewire through a patient's vasculature until it is positioned proximal to and/or aligned with a calcified lesion in a body lumen. The balloon is then inflated with a fluid (e.g., for electrohydraulically generated acoustic shock waves, a conductive fluid such as a saline solution) so that the balloon expands (e.g., to a relatively low pressure of 2-4 atm) to contact the lesion, but is not inflated to a pressure that substantively displaces the lesion. Voltage pulses can then be supplied to the emitters (e.g., by applying a voltage across one or more electrode pairs of an emitter) to produce acoustic shock waves that propagate through the walls of the angioplasty balloon and into the lesions. Once the lesions have been cracked by the acoustic shock waves, the balloon can be expanded further to increase the cross-sectional area of the lumen and improve blood flow through the lumen. Alternative devices to deliver IVL therapy can be within a closed volume other than an angioplasty balloon, such as a cap, balloons of variable compliancy, or other enclosures.

However, conventional shock wave catheters may be less effective for treating lesions in large blood vessels and valves. Catheters should be sufficiently small to maneuver through vessels that the catheters traverse to reach the large blood vessels and valves. Once in the large blood vessels and valves, a balloon of the catheter is inflated to a relatively large diameter that moves the walls of the balloon farther from the emitters within the balloon, which are typically located along a central tube running along the longitudinal axis of the catheter. Accordingly, when shock waves are emitted, they may need to propagate farther in larger blood vessels to reach lesions than in smaller blood vessels, which may reduce the force applied to crack the lesions. To address the decreased force output from emitters inside large angioplasty balloons, some catheters increase the supplied power to the emitters to produce higher magnitude shock waves in the balloon. However, increasing the magnitude of the shock waves requires increased power and may introduce other issues, such as increased wear on the emitters of the device and a risk of rupturing the balloon wall with high voltage shock waves. Other treatment protocols for large vessels and valves may require longer shock wave treatments, which risks ischemia and other complications during an angioplasty procedure.

BRIEF SUMMARY

In view of the above, there is a need to position emitters for IVL devices more proximate to lesions in relatively large vasculature or other body lumens and chambers (e.g., heart valve chambers). Embodiments of the present disclosure generally accomplish such positioning through mechanical and structural techniques. According to an aspect of the present disclosure, a shock wave catheter includes at least one shock wave emitter configured to move laterally relative to a central longitudinal axis of the catheter to decrease the distance between the at least one emitter and a lesion in a body lumen. The emitter(s) may be movably connected to an elongated tube of the catheter, such that, in a first configuration, the emitter(s) are in a first position and, in a second configuration, the emitter(s) are in a second position farther from the central longitudinal axis than the first position. The emitter(s) can be supported by an expanding support structure that can laterally expand to move the emitter(s) farther from a central longitudinal axis of the catheter and closer to the lesion. The support structure can then be collapsed back into a low profile state to enable the catheter to maneuver through smaller body lumens if needed. The emitter(s) can be positioned within one or more laterally expandable enclosures. The enclosures may be configured such that the lumen is not occluded when the enclosures are laterally expanded (e.g., to maintain blood flow during treatment). The emitter(s) can be positioned in one or more balloons of a multiple balloon configuration that, when inflated, can move the emitter(s) closer to the lesion. The emitters can be positioned within a plurality of enclosures (e.g., balloons or non-inflatable enclosures), that are moveable closer to a lesion using a movable shaft that causes the multiple enclosures to move into an expanded configuration. In yet another approach, the emitter(s) can be positioned on an inner wall of a balloon such that expansion of the balloon moves the emitter(s) closer to the lesion.

Decreasing the distance between the emitters and lesions in a body lumen may result in the delivery of increased forces to the lesions during a shock wave treatment, without the need for longer treatments or higher power applied to the emitters. Such catheters may facilitate the treatment of larger body lumens, such as large blood vessels and valves, as well as irregular lesions, such as nonconcentric and/or nodular calcified lesions. Advantageously, according to one or more embodiments, a single sized expandable catheter may be employed to optimally treat lesions of a relatively wide range of vasculature sizes and/or a wide range of vessel occlusions.

In some embodiments, a catheter for treating a lesion in a body lumen is provided, the catheter including: an elongated tube, an enclosure sealed to a distal end of the elongated tube, an emitter assembly disposed within the enclosure. In some embodiments, the emitter assembly comprises at least one emitter configured to generate shock waves inside the enclosure when power is supplied to the at least one emitter. In some embodiments, the catheter further includes a support structure supporting the at least one emitter. In some embodiments, the support structure is configured to expand outwardly relative to a central longitudinal axis of the elongated tube to move the at least one emitter farther from the central longitudinal axis.

In some embodiments, the support structure includes a plurality of segments connected by respective joints.

In some embodiments, at least one emitter is mounted on the support structure proximate to one or more of the joints.

In some embodiments, at least one emitter includes a first emitter mounted proximate to a first joint of the support structure and a second emitter mounted proximate to a second joint of the support structure.

In some embodiments, the joints of the support structure are configured to hinge in alternating directions such that the first emitter moves outward from the longitudinal axis in a first direction, and the second emitter moves outward from the longitudinal axis in a second direction opposite the first direction.

In some embodiments, the at least one emitter includes a first electrode mounted on a first segment and a second electrode mounted on a second segment such that a spark gap between the electrodes is between the first and second segments.

In some embodiments, one or more of the joints is a living hinge.

In some embodiments, the at least one emitter includes a first emitter and a second emitter, and wherein expansion of the support structure moves the first emitter outward from the longitudinal axis in a first direction and the second emitter outward from the longitudinal axis in a second direction transverse to the first direction.

In some embodiments, the at least one emitter further includes a third emitter, and wherein expansion of the support structure moves the third emitter outward from the longitudinal axis in a third direction transverse to the first direction and the second direction.

In some embodiments, the at least one emitter includes a first emitter and a second emitter, and wherein lateral expansion of the support structure moves the first emitter and the second emitter laterally away from the longitudinal axis in opposing directions along a first plane intersecting the longitudinal axis.

In some embodiments, the at least one emitter includes a first emitter and a second emitter, and wherein lateral expansion of the support structure moves the first emitter laterally away from the longitudinal axis along a first plane that is coplanar with the longitudinal axis and moves the second emitter outward from the longitudinal axis along a second plane that is coplanar with the longitudinal axis and transverse to the first plane.

In some embodiments, the first and the second plane are perpendicular to each other.

In some embodiments, the at least one emitter further includes a third emitter, and wherein expansion of the support structure moves the third emitter outward from the longitudinal axis along a third plane that is coplanar with the longitudinal axis and transverse to the first plane and the second plane.

In some embodiments, the at least one emitter further includes a third emitter and a fourth emitter, and wherein expansion of the support structure moves the first emitter and the third emitter outward from the longitudinal axis in opposing directions along the first plane, and wherein expansion of the support structure moves the second emitter and the fourth emitter outward from the longitudinal axis in opposing directions along the second plane.

In some embodiments, the emitter assembly further comprising an elongate member that extends along the longitudinal axis through at least a portion of the expandable support structure.

In some embodiments, the support structure includes one or more apertures, and the elongate member extends through one or more of the apertures.

In some embodiments, movement of the elongate member in a proximal direction or a distal direction causes expansion of the support structure.

In some embodiments, the expanded diameter of the support structure is controllable by moving the elongate member in the proximal direction or the distal direction.

In some embodiments, the elongate member includes one or more markings that indicate to a user an amount of movement of the elongate member associated with one or more expanded diameters of the support structure.

In some embodiments, the support structure includes a first stop and a second stop that are spaced apart in a collapsed state of the support structure and abutting in an expanded state of the support structure.

In some embodiments, the elongate member is operably coupled to at least one of the first stop and the second stop such that movement of the elongate member moves the first stop relative to the second stop.

In some embodiments, the elongate member includes a wire, and wherein movement of the wire in a proximal direction causes expansion of the support structure.

In some embodiments, the elongate member includes a first tube and a second tube surrounding at least a portion of the first tube, and wherein movement of the first tube relative to the second tube causes expansion of the support structure.

In some embodiments, moving the elongate member a predetermined distance causes the support structure to reversibly lock in an expanded state.

In some embodiments, in a collapsed state, the support structure has a diameter less than 1 mm.

In some embodiments, the support structure is expandable to a diameter of at least five millimeters (5 mm).

In some embodiments, the support structure is expandable to a diameter of at least one centimeter (1 cm).

In some embodiments, the enclosure is an angioplasty balloon.

In some embodiments, the enclosure has an inflated diameter between eight millimeters (8 mm) and twelve millimeters (12 mm).

In some embodiments, the enclosure has an inflated diameter greater than twenty millimeters (20 mm).

In some embodiments, the body lumen is a blood vessel or a valve.

In some embodiments, the support structure is formed of a resilient material selected from the group consisting of a metal or a polymeric material.

In some embodiments, after expansion of the support structure, the structure can return to substantially the same configuration in the collapsed state.

In some embodiments, material properties of the support structure bias the support structure in a collapsed state.

In some embodiments, material properties of the support structure bias the support structure in an expanded state.

In some embodiments, the catheter further includes one or more springs connected to a proximal end or a distal end of the support structure.

In some embodiments, the one or more springs are configured to bias the support structure in a collapsed state.

In some embodiments, the one or more springs are configured to bias the support structure in an expanded state.

In some embodiments, the emitter assembly further comprising a first wire and a second wire, the first and second wires extending along at least a portion of the elongated tube and configured to apply a voltage to one or more of the at least one emitter such that a current is transmitted across at least one electrode pair of the at least one emitter.

In some embodiments, at least a portion of the support structure is conductive and configured to provide a voltage to the at least one emitter.

In some embodiments, the at least one emitter is oriented to generate shock waves outwardly from the longitudinal axis.

In some embodiments, the support structure comprises a flexible ribbon and wherein: in a first configuration, the ribbon is substantially uncoiled, and in a second configuration, the ribbon is helically coiled and the at least one emitter is no less than 1 mm away from a central longitudinal axis of the enclosure.

In some embodiments, in the second configuration, the at least one emitter is about 3 mm-6 mm away from the central longitudinal axis of the enclosure.

In some embodiments, in the second configuration, the at least one emitter is less than 1 mm away from the wall of the enclosure.

In some embodiments, the enclosure is an angioplasty balloon, and, in the second configuration, the balloon is filled to a pressure of about 1 atm to about 6 atm.

In some embodiments, the ribbon is in the first configuration when the enclosure is uninflated and configured to automatically change to the second configuration when the enclosure is inflated.

In some embodiments, the support structure is connected to a rotatable proximal handle and rotation of the proximal handle changes the ribbon from the first configuration to the second configuration.

In some embodiments, a catheter for treating a lesion in a body lumen is provided, the catheter comprising an elongated tube, at least one emitter configured to generate shock waves when power is supplied to the at least one emitter a first enclosure surrounding a first emitter of the at least one emitter and being fillable with a fluid, and a second enclosure, the second enclosure being fillable with the fluid for expanding the second enclosure. In some embodiments, expansion of the second enclosure while the catheter is disposed within a body lumen moves the at least one emitter closer to the lesion in the body lumen.

In some embodiments, the first enclosure and the second enclosure are independently fillable with the fluid.

In some embodiments, the elongated tube includes a first channel for introducing the fluid into the first enclosure and a second channel for introducing the fluid into the second enclosure.

In some embodiments, the first enclosure is sealed at one end to the elongated tube.

In some embodiments, the first emitter is mounted on the elongated tube inside the first enclosure.

In some embodiments, the first emitter is disposed on an inner surface of the first enclosure.

In some embodiments, the second enclosure surrounds a second emitter of the at least one emitter.

In some embodiments, the catheter includes a second elongated tube, wherein the second enclosure is sealed to a region of the second elongated tube.

In some embodiments, the second elongated tube includes a fluid lumen for introducing fluid into the second enclosure.

In some embodiments, the second emitter is mounted on the second elongated tube.

In some embodiments, the catheter further includes a third enclosure, wherein the third enclosure surrounds a third emitter of the at least one emitter.

In some embodiments, the second enclosure is a central enclosure, and wherein the first enclosure and the third enclosure are disposed adjacent and peripheral to the central enclosure when the catheter is disposed within a body lumen.

In some embodiments, the first emitter of the first enclosure and the third emitter of the third enclosure are configured to selectively generate shock waves.

In some embodiments, the central enclosure does not surround an emitter.

In some embodiments, the fluid is a conductive fluid.

In some embodiments, a catheter for treating a lesion in a body lumen is provided, the catheter comprising an elongated tube, an enclosure sealed to the elongated tube and being fillable with fluid, and at least one emitter disposed on an inner surface of the enclosure and configured to generate shock waves inside the enclosure when power is supplied to the at least one emitter. In some embodiments, expansion of the enclosure while the catheter is disposed within the body lumen moves the at least one emitter closer to a wall of the body lumen.

In some embodiments, the at least one emitter is adhesively attached to the inner surface of the balloon.

In some embodiments, the at least one emitter includes a plurality of emitters.

In some embodiments, the plurality of emitters is disposed on the inner surface of the balloon in a spiral pattern or a grid pattern.

In some embodiments, the at least one emitter is oriented to generate shock waves outwardly from a longitudinal axis of the catheter.

In some embodiments, each of the at least one emitter includes a pair of electrodes forming a spark gap between the electrodes, and wherein the spark gap is at least one-tenth of a millimeter (0.1 mm) away from the inner surface of the enclosure.

In some embodiments, each of the at least one emitter includes a spacer configured to maintain the spark gap at least one-tenth of a millimeter (0.1 mm) away from the inner surface of the enclosure.

In some embodiments, the catheter further includes a first wire and a second wire, the first and second wires extending along at least a portion of the elongated tube and configured to supply power to one or more of the at least one emitter.

In some embodiments, the fluid is a conductive fluid.

In some embodiments, a system for treating a lesion in a body lumen is provided, the system comprising a catheter and a power source configured to supply power to at least one emitter to generate shock waves for treating the lesion.

In some embodiments, a method for treating a lesion in a body lumen is provided, the method comprising advancing a catheter within the body lumen to a position proximate to the lesion. In some embodiments, the method includes inflating an enclosure of the catheter so that an outer surface of the enclosure contacts the body lumen. In some embodiments, the method includes expanding a support structure inside the enclosure to position at least one emitter disposed on the support structure closer to the lesion in the body lumen. In some embodiments, the method includes supplying power to the at least one emitter to generate one or more shock waves inside the enclosure to treat the lesion.

In some embodiments, expanding the support structure moves a first emitter outward from a longitudinal axis of the catheter in a first direction and moves a second emitter outward from the longitudinal axis in a second direction.

In some embodiments, the first direction is opposite the second direction.

In some embodiments, the support structure includes a first stop and a second stop that are spaced apart in a collapsed state of the support structure and abutting in an expanded state of the support structure, and wherein expanding the support structure includes moving the second stop toward the first stop.

In some embodiments, expanding the support structure includes moving an elongate member in a proximal direction or a distal direction, and the elongate member extends between and is operably coupled to at least one of the first stop and the second stop.

In some embodiments, the elongate member includes a first tube and a second tube surrounding at least a portion of the first tube, and movement of the second tube relative to the first tube causes expansion of the support structure.

In some embodiments, expanding the support structure includes pulling a wire operably coupled to at least one of the first stop and the second stop.

In some embodiments, the method further includes rotating the support structure to position the at least one emitter closer to the lesion in the body lumen.

In some embodiments, the enclosure is in a folded state when the catheter is advanced through the body lumen.

In some embodiments, the diameter of the support structure is less than 1 mm when the catheter is advanced through the body lumen.

In some embodiments, expanding the support structure includes expanding the support structure to a diameter between eight millimeters (8 mm) and twelve millimeters (12 mm).

In some embodiments, expanding the support structure includes expanding the support structure to a diameter greater than one centimeter (1 cm).

In some embodiments, the catheter further includes, after supplying power to the one or more emitters to generate the one or more shock waves, further expanding the support structure.

In some embodiments, a method for treating a lesion in a body lumen is provided, the method including advancing a catheter within the body lumen to a position proximate to the lesion.

In some embodiments, the method includes inflating a first enclosure of the catheter, wherein the first enclosure surrounds a first emitter. In some embodiments, the method includes inflating a second enclosure of the catheter, wherein inflating the second enclosure while the catheter is disposed within the body lumen moves the first emitter closer to the lesion in the body lumen. In some embodiments, the method includes supplying power to the first emitter to generate one or more shock waves inside the first enclosure to treat the lesion.

In some embodiments, the second enclosure surrounds a second emitter, and the method further includes supplying power to the second emitter to generate one or more shock waves inside the second enclosure.

In some embodiments, inflating the first enclosure and the second enclosure includes filling the enclosures with a conductive fluid.

In some embodiments, inflating the first enclosure includes filling the first enclosure with conductive fluid via a first fluid lumen, and wherein inflating second enclosure includes filling the second enclosure with conductive fluid via a second fluid lumen.

In some embodiments, the first enclosure and the second enclosure are in a folded state when the catheter is advanced through the body lumen.

In some embodiments, the method further includes rotating the first enclosure and the second enclosure around a longitudinal axis of the catheter to move the first emitter closer to the occlusion in the body lumen.

In some embodiments, the method further includes inflating a third enclosure of the catheter, wherein inflating the third enclosure while the catheter is disposed within the body lumen moves the first emitter closer to the lesion in the body lumen.

In some embodiments, the third enclosure surrounds a third emitter, and the method further includes supplying power to the third emitter to generate one or more shock waves inside the third enclosure.

In some embodiments, a method for treating a lesion in a body lumen is provided, the method including advancing a catheter within the body lumen to a position proximate to the lesion. In some embodiments, the method includes inflating an enclosure of the catheter such that a plurality of emitters disposed on an inner surface of the enclosure move closer to the lesion in the body lumen. In some embodiments, the method includes supplying power to the plurality of emitters to generate one or more shock waves to treat the lesion.

In some embodiments, a shock wave catheter is provided including an elongated tube having a central longitudinal axis, an enclosure sealed to the distal end of the elongated tube, an adjustable emitter assembly disposed within the enclosure. In some embodiments, the emitter assembly includes at least one shock wave generating emitter movably connected to the elongated tube such that, in a first configuration, the at least one emitter is in a first position and, in a second configuration, the at least one emitter is in a second position that is no less than 3 mm farther from the central longitudinal axis than the first position.

In some embodiments, a shock wave catheter is provided including an elongated tube having an emitter port and defining a central longitudinal axis, an enclosure sealed to a distal end of the elongated tube, and a shock wave generating emitter that is located along an emitter axis that is not parallel to the central longitudinal axis. In some embodiments, the emitter axis extends from the central longitudinal axis through the emitter port.

In some embodiments, in a first configuration, the shock wave generating emitter is located within the emitter port, and, in a second configuration, the shock wave generating emitter is located at least one-half millimeter (0.5 mm) outside of the emitter port.

In some embodiments, the catheter further includes a second shock wave generating emitter located along a second emitter axis that is not parallel to the central longitudinal axis, and the elongated tube has a second emitter port, and the second emitter axis extends through the second emitter port.

In some embodiments, a method for treating a lesion in a body lumen is provided, the method including advancing a catheter having a distal end and a proximal end within the body lumen to a position proximate to the lesion such that a first shock wave generating emitter of the catheter is located distal to the lesion and a second shock wave generating emitter of the catheter is located proximal to the lesion. In some embodiments, the method further includes inflating an enclosure of the catheter with a fluid, wherein the enclosure surrounds the first and second shock wave generating emitters. In some embodiments, the method further includes moving the first and second shock wave generating emitters laterally away from an elongated tube of the catheter. In some embodiments, the method further includes supplying power to the first and second shock wave generating emitters to generate at least one shock wave from each of the first and second shock wave generating emitters to treat the lesion.

In some embodiments, the first and second shock wave generating emitters are supplied with power such that shock waves are generated from the first and second emitters at substantially the same time.

In some embodiments, the first and second shock wave generating emitters each comprise a pair of electrodes and supplying power to the emitters includes applying a voltage across each electrode pair.

In some embodiments, a method for treating a lesion in a body lumen is provided, the method including advancing a catheter within the body lumen to a position proximate to the lesion. In some embodiments, the catheter includes an elongated tube, an enclosure sealed to a distal end of the elongated tube, and a shock wave generating emitter assembly disposed within the enclosure. In some embodiments, the emitter assembly includes a first emitter, a second emitter circumferentially aligned with the first emitter, a third emitter axially aligned with the first emitter and circumferentially offset form the second emitter, a fourth emitter circumferentially aligned with the third emitter and axially aligned with second emitter, and a support structure supporting the first, second, third, and fourth emitters. In some embodiments, the support structure is configured to expand laterally relative to a central longitudinal axis of the elongated tube to move the first, second, third, and fourth emitters farther from the central longitudinal axis. In some embodiments, the method further includes inflating an enclosure of the catheter with a fluid, wherein the enclosure surrounds the first, second, third, and fourth shock wave generating emitters. In some embodiments, the method further includes moving the first, second, third, and fourth emitters laterally away from the elongated tube. In some embodiments, the method further includes supplying power to the emitter assembly to generate one or more shock waves from at least one of the first, second, third, and fourth shock wave generating emitters.

In some embodiments, the method further includes positioning the catheter such that the first emitter is located distal to the lesion and the second emitter is located proximal to the lesion, wherein supplying power to the emitter assembly includes supplying power to the first and second emitters.

In some embodiments, moving the first and second emitters laterally away from the elongated tube moves the first and second emitters closer to each other.

In some embodiments, a shock wave catheter is provided including an elongated tube, an enclosure sealed to the elongated tube and being fillable with fluid via a lumen of the elongate tube, and a flexible ribbon including at least one emitter configured to generate a shock wave supplied with power. In some embodiments, in a first configuration, the ribbon is substantially uncoiled, and in a second configuration, the ribbon is helically coiled and the at least one emitter is no less than 1 mm away from a central longitudinal axis of the balloon.

In some embodiments, in the second configuration, the at least one emitter is about three millimeters to six millimeters (3 mm-6 mm) away from the central longitudinal axis of the balloon.

In some embodiments, in the second configuration, the at least one emitter is less than 1 mm away from the wall of the enclosure.

In some embodiments, the enclosure is an angioplasty balloon, and, in the second configuration, the balloon is filled to a pressure of about two atmospheres (2 atm) to about six atmospheres (6 atm).

According to an aspect, an exemplary catheter for treating a lesion in a body lumen comprises: a catheter body comprising a plurality of lumens; a distal tip; a movable shaft that extends from a proximal portion of the catheter to the distal tip and is longitudinally movable in a first lumen of the plurality of lumens of the proximal shaft; and a laterally expandable structure including at least one emitter support fixedly positioned in a second lumen of the plurality of lumens of the proximal shaft and extending to the distal tip, the at least one emitter support comprising: an outer elongate member; an inner elongate member; a shock wave emitter assembly positioned on the inner elongate member; where: in a laterally collapsed configuration of the expandable structure, the movable shaft is in a proximal position, in a laterally expanded configuration of the expandable structure, the movable shaft is in a distal position, in the laterally expanded configuration, the catheter is configured to allow passage of fluid around the laterally expanded structure.

In some embodiments, in the laterally expanded configuration, the catheter has an expanded maximum width w, the catheter has an expanded footprint FP, $FP=\pi(w/2)^2$, a distal end of the catheter body, at the laterally expandable structure, has a cross-sectional area less than 50% of FP.

In some embodiments, the laterally expandable structure includes a plurality of emitter supports that are laterally expandable.

In some embodiments, each of the plurality of emitter supports comprises an emitter assembly and each emitter assembly is separately connected to the energy source.

In some embodiments, each of the plurality of emitter supports is fluidically connected to a fluid source.

In some embodiments, each of the plurality of emitter supports extends proximally through individual lumens of the plurality of lumens of the proximal shaft.

In some embodiments, the plurality of emitter supports extends proximally together in one lumen of the catheter body.

In some embodiments, the laterally expandable structure includes three emitter supports.

In some embodiments, the emitter support comprises a plurality of hinges.

In some embodiments, the emitter support comprises a shape memory material.

In some embodiments, in the expanded configuration, the emitter support is in contact with a wall of the body lumen.

In some embodiments, the emitter assembly includes at least one shock wave emitter comprising at least one electrode pair.

In some embodiments, the catheter body comprises a guidewire lumen.

In some embodiments, the emitter assembly is farther from a central longitudinal axis of the catheter in the laterally expanded configuration than in the laterally collapsed configuration.

In some embodiments, the emitter support comprises: a proximal region extending from the proximal shaft; a distal region extending to the distal tip; a central region located between the proximal region and the distal region; and transition regions between the central region and the proximal and distal regions, wherein the central region is parallel to a central longitudinal axis of the catheter in both the laterally collapsed configuration and the laterally expanded configuration.

In some embodiments, the emitter support further comprises bending regions at proximal and distal ends of each transition region.

In some embodiments, the bending regions comprise a thinner outer elongate member than the central region.

In some embodiments, the movable shaft is longitudinally slidable relative to the emitter support.

In some embodiments, the proximal shaft has a proximal outer diameter and the expandable structure has a maximum width in the collapsed configuration less than or equal to the proximal outer diameter.

In some embodiments, the distal tip has a distal outer diameter and the expandable structure has a maximum width in the collapsed configuration less than or equal to the proximal outer diameter.

According to an aspect, an exemplary method of treating a lesion in a body lumen comprises: advancing an IVL catheter having a laterally expandable structure including a shock wave emitter assembly through the body lumen, wherein the laterally expandable structure is in a laterally collapsed configuration; positioning the emitter assembly adjacent the lesion; moving the emitter assembly closer to the lesion by laterally expanding the laterally expandable structure; introducing a solution through a fluid lumen of the laterally expandable structure to the emitter assembly; supplying energy to the emitter assembly from an energy source connected by an energy guide to the emitter assembly to generate one or more shock waves; and laterally compressing the expandable structure, where the catheter comprises a movable shaft and a catheter body having a plurality of lumens and the movable shaft is in a more proximal position in a first lumen of the plurality of lumens in the laterally expanded configuration than in the laterally collapsed configuration.

In some embodiments, laterally expanding the laterally expandable structure comprises moving a movable shaft connected to the expandable structure from a distal position to a proximal position.

In some embodiments, laterally expanding the laterally expandable structure forms at least one gap for blood to flow past the laterally expandable structure in the body lumen.

In some embodiments, introducing the solution comprises pulling vacuum on the fluid lumen at a proximal end of the fluid lumen and replacing the vacuum with a fluid source to fill with laterally expandable structure with the solution.

In some embodiments, introducing the solution fills an enclosure of the laterally expandable structure, wherein the enclosure is configured such that it does not inflate when filled with the solution.

According to an aspect, an exemplary method of treating a lesion in a body lumen comprises: advancing an IVL catheter having a laterally expandable structure including a shock wave emitter assembly through the body lumen, wherein the laterally expandable structure is in a laterally collapsed configuration; positioning the emitter assembly adjacent the lesion; moving the emitter assembly closer to the lesion by laterally expanding the laterally expandable structure such that an outer elongate member of the laterally expandable structure contacts the lesion; introducing a solution through a fluid lumen of the laterally expandable structure to the emitter assembly; supplying energy to the emitter assembly from an energy source connected by an energy guide to the emitter assembly to generate one or more shock waves; and laterally compressing the expandable structure.

In some embodiments, the outer elongate member comprises the fluid lumen.

In some embodiments, the outer elongate member is configured such that it does not inflate when filled with the solution.

In some embodiments, laterally expanding the laterally expandable structure such that an outer elongate member of the laterally expandable structure contacts the lesion enables blood to flow past the laterally expandable structure within the lumen.

BRIEF DESCRIPTION OF THE FIGURES

Illustrative aspects of the present disclosure are described in detail below with reference to the following figures. It is intended that the embodiments and figures disclosed herein are to be considered illustrative rather than restrictive.

FIG. 2A illustrates the expandable support structure in a collapsed state. FIG. 2B illustrates the expandable support structure in an expanded state.

FIG. 3A illustrates the expandable support structure in a collapsed state. FIG. 3B illustrates the expandable support structure in an expanded state.

FIG. 4A illustrates an expandable support structure including at least two emitters configured to move outward from the longitudinal axis of the catheter in opposing directions. FIG. 4B illustrates an expandable support structure including at least three emitters configured to move outward from the longitudinal axis of the catheter in three transverse directions. FIG. 4C illustrates an expandable support structure including at least four emitters configured to move outward from the longitudinal axis in at least two planes intersecting the longitudinal axis.

FIG. 5A illustrates the first stop positioned away from the second stop (e.g., when the expandable support structure of the catheter is in a collapsed state for insertion and/or advancement of the catheter). FIG. 5B illustrates the first stop abutting the second stop (e.g., when the expandable support structure of the catheter is in an expanded state). FIG. 5C illustrates the second stop positioned away from the first stop (e.g., when the expandable support structure of the catheter is in a collapsed state for removal of the catheter).

FIG. 6A illustrates an arrangement of a first enclosure and a second enclosure. FIG. 6B illustrates a quad-balloon arrangement having a first balloon, a second balloon, a third balloon, and a fourth balloon (two of the balloons are visible in the figure). FIG. 6C illustrates an arrangement having a central balloon and a plurality of peripheral balloons.

FIG. 7A illustrates an arrangement of a first enclosure and a second enclosure. FIG. 7B illustrates a quad-balloon arrangement having a first balloon, a second balloon, a third balloon, and a fourth balloon (two of the balloons are visible in the figure). FIG. 7C illustrates an arrangement having a central balloon and a plurality of peripheral balloons.

FIG. 14A illustrates a first configuration of the catheter, where the ribbon is substantially straight (e.g., substantially uncoiled). FIG. 14B illustrates a second embodiment of the catheter, where the ribbon is helically coiled and substantially about a central longitudinal axis of the enclosure.

FIG. 15A and FIG. 15B illustrate the shock wave generating regions at least partially housed within the angled ports. FIG. 15C and FIG. 15D illustrate the shock wave generating regions moved outwards from the angled ports such that the shock wave generating regions are farther away from a central axis of the catheter.

DETAILED DESCRIPTION

Figure 1:
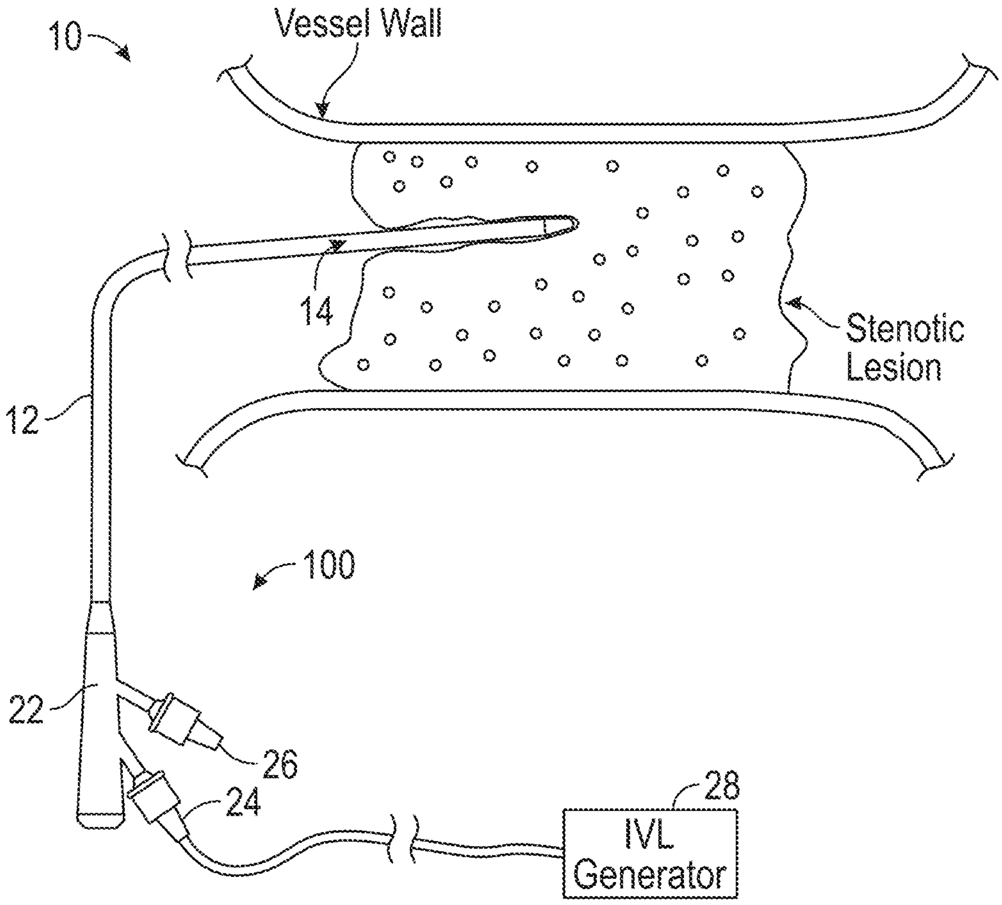
FIG. 1 illustrates an exemplary system comprising a shock wave catheter and a power source, with the catheter pictured treating a stenosis in a blood body lumen, according to one or more aspects of the present disclosure.

The following description is presented to enable a person of ordinary skill in the art to make and use the various embodiments and aspects thereof disclosed herein. Descriptions of specific catheters, systems, methods, and applications are provided only as examples. Various modifications to the examples described herein will be readily apparent to those of ordinary skill in the art, and the general principles described herein may be applied to other examples and applications without departing from the spirit and scope of the various embodiments and aspects thereof. Thus, the various embodiments and aspects thereof are not intended to be limited to the examples described herein and shown but are to be accorded the scope consistent with the claims.

Described herein are shock wave catheters incorporating at least one emitter inside an enclosure at the distal end of the catheter, such as an inflatable angioplasty balloon or a non-inflatable cap. The at least one emitter can be moved outward from a central longitudinal axis of the catheter to position the emitter(s) farther from the central longitudinal axis of the catheter and closer to the enclosure wall and, thus, closer to a body lumen containing a lesion that is targeted for treatment by the catheter. As used herein, the terms "outward," "radial," or "lateral" refers to a direction that is transverse (e.g., includes a component that is normal) to a catheter's central longitudinal axis. Accordingly, moving an emitter "outward", "radially", or "laterally" from the central longitudinal axis of a catheter indicates that the emitter is moving from a first position closer to the longitudinal axis to a second position farther from the longitudinal axis (and/or closer to a lesion in a body lumen) in a direction that is normal to the central longitudinal axis.

Advantageously, these catheters can be inserted and advanced through a body lumen in a relatively lower profile state, and the emitters can be moved outward after the catheter has been positioned in the body lumen requiring treatment. Accordingly, the outward movement of the emitters in situ does not prevent the catheter from being inserted into, advancing through, and treating relatively smaller regions of body lumens. When the catheter is positioned in a body lumen, such as a vessel or valve, moving the emitter closer to the lesion in the body lumen reduces the distance the shock waves have to travel between the emitter and the lesion compared to shock waves emitted from a more central location within the enclosure, thereby resulting in less reduction in the force of the shock waves when they reach the lesion, improving the speed and efficacy of treatments with a shock wave catheter. Such catheters may be particularly useful for the treatment of large body lumens, like large vessels and valves in vasculature, as well as eccentric and nodular calcium and other irregular lesions in body lumens.

The emitter(s) can be moved closer to the body lumen in a number of ways. For instance, in some examples, the emitters are movably connected to the elongated tube such that the emitters can be moved from a first configuration to a second configuration to position the emitters farther from the central longitudinal axis of the catheter. In some examples, the emitters are disposed on a laterally expandable support structure within the enclosure, and the support structure can be expanded outwardly from the longitudinal axis of the catheter within the enclosure to position one or more of the emitters mounted on the support structure closer to the body lumen. In another example, the catheter includes multiple adjacent enclosures, at least one of which is inflatable and at least one of which includes at least one emitter. Inflation of one or more of the inflatable enclosures moves the at least one emitter closer to the wall of the body lumen. In some examples, the multiple enclosures are not inflatable or are minimally inflatable to reduce the amount of blood flow blockage. In yet a further example, the catheter includes an enclosure having at least one emitter disposed on an inner surface of the enclosure, such that inflation of the enclosure within the body lumen causes the emitter to move away from the longitudinal axis of the catheter and toward the body lumen.

As used herein, the term "electrode" refers to an electrically conducting element (typically made of metal) that receives electrical current and subsequently releases the electrical current to another electrically conducting element. In the context of the present disclosure, electrodes are often positioned relative to each other, such as in an arrangement of an inner electrode and an outer electrode. Accordingly, as used herein, the term "electrode pair" refers to two electrodes that are positioned adjacent to each other such that application of a sufficiently high voltage to the electrode pair will cause an electrical current to transmit across the gap (also referred to as a "spark gap") between the two electrodes (e.g., from an inner electrode to an outer electrode, or vice versa, optionally with the electricity passing through a conductive fluid or gas therebetween). In some contexts, one or more electrode pairs may also be referred to as an electrode assembly. In the context of the present disclosure, the term "emitter" broadly refers to the region of an electrode assembly where the current transmits across an electrode pair, generating a shock wave. Emitters can be singular, paired, or otherwise arranged together. During a shock wave treatment, shock waves can be generated at all of the emitters, or at only a particular subset of the emitters. Emitters can be wired in series to generate shock waves together. Emitters can be on separate circuits or separate circuit branches to be operated separately. The term "emitter sheath" refers to a sheath of conductive material that may form one or more electrodes of one or more electrode pairs, thereby forming a location of one or more emitters. One or more of the emitters, emitter sheaths, emitter assemblies, and/or electrodes may be formed from a metal, such as stainless steel, copper, tungsten, platinum, palladium, molybdenum, cobalt, chromium, iridium, or an alloy or alloys thereof, such as cobalt-chromium, platinum-chromium, cobalt-chromium-platinum-palladium-iridium, or platinum-iridium, or a mixture of such materials.

As used herein, the term "shock wave generating region" refers to a structure on an catheter capable of generating shock waves. For example, a shock wave generating region can encompass an emitter or emitter sheath. In an electrohydraulic IVL catheter, a shock wave generating region can include one or more electrode pairs that emit shock waves in response to a current being transmitted across a spark gap. In other examples, high-energy lasers are used to generate shock waves by pulsing laser light inside an enclosure. In such an example, the catheter could include one or more optical fibers, and the output ends thereof are shock wave generating regions. Still other types of shock wave generating sources are possible, such as sources that are piezoelectric and/or electromagnetic based. For example, a shock wave generating region may include a piezoelectric transducer.

As provided herein, it should be appreciated that any disclosure of a numerical range describing dimensions or measurements such as thicknesses, length, weight, time, frequency, temperature, voltage, current, angle, etc. is inclusive of any numerical increment or gradient within the ranges set forth relative to the given dimension or measurement. Furthermore, numerical designators such as "first," "second," "third," "fourth," etc. are merely descriptive and do not indicate a relative order, location, or identity of elements or features described by the designators. For instance, a "first" shock wave may be immediately succeeded by a "third" shock wave, which is then succeeded by a "second" shock wave. As another example, a "third" emitter may be used to generate a "first" shock wave and vice versa. Accordingly, numerical designators of various elements and features are not intended to limit the disclosure and may be modified and interchanged.

FIG. 1 depicts an exemplary system 10 that includes a shock wave catheter 100 according to one or more examples. The shock wave catheter 100 includes an elongated tube 12 and at least one enclosure (e.g., an inflatable angioplasty balloon or a non-inflatable cap) enclosing one or more shock wave emitters (not shown) that emit shock waves inside the enclosure to treat a lesion in a body lumen, such as the stenotic lesion pictured in FIG. 1. In various examples, the lesion could be a calcified region of vasculature, a thrombus or an occlusion in vasculature, arteriosclerotic plaque, or a lesion in some other body lumen, such as a kidney stone in a ureter.

The elongated tube 12 extends generally along a central longitudinal axis of the catheter 100 between a handle 22 of the catheter 100 at its proximal end and a distal end 14 of the catheter. As described in more detail below, the distal end 14 includes the shock wave emitters and the enclosure(s) and is configured to be inserted into a body lumen of a patient, such as a blood vessel, a valve, a ureter, or some other body lumen. The elongated tube 12 may include various lumens and/or channels sized for carrying fluid, conductive wires, and other aspects of the catheter 100 between its proximal handle 22 and the distal end 14, such as a fluid lumen for carrying fluid introduced through a fluid port 26 and various conductive wires that enter through one or more wire ports 24. In some examples, the handle 22 is configured to receive a guidewire through a guidewire lumen in the elongated tube 12 to aid in insertion and positioning of the distal end 14 of the catheter 100. In such examples, a guidewire may be inserted within the interior of the elongated tube 12 in order to position the enclosure(s) at the catheter's distal end 14 proximate to a lesion in a body lumen. However, in some examples the elongated tube 12 does not include a guidewire lumen.

In some aspects, the enclosure(s) of the catheter 100 wraps circumferentially around a portion of the elongated tube 12 and may be sealed to a region of the elongated tube via, for example, a seal. In a deflated state, the enclosure(s) may be positioned closely proximate to the elongated tube 12 and optionally in a folded state, which improves the maneuverability of the catheter 100 during insertion and positioning. The enclosure(s) can be filled with conductive fluid, such as saline, such that the enclosure expands (i.e., inflates) to contact a body lumen (such as the walls of an artery proximal to a calcified lesion). When inflated, the enclosure(s) provides an annular channel around the elongated tube 12 and creates a space between the emitters of the assembly and the inner surface of the enclosure. In one or more examples, the conductive fluid may also contain an x-ray contrast fluid to permit fluoroscopic viewing of the catheter 100 by a surgeon during use.

The system 10 also includes a power source 28 (e.g., a high voltage pulse generator or a laser, shown in FIG. 1 as an intravascular lithotripsy "IVL Generator") configured to supply power to the shock wave emitters to generate shock waves during a treatment with the catheter 100. For electrohydraulic generation of acoustic shock waves, a conductive solution (e.g., saline) may be contained within an enclosure that surrounds the electrodes or can be flushed through a tube that surrounds the electrodes. A voltage pulse may be delivered from the power source 28 to the emitter(s), resulting in an electrical discharge across the electrodes. This discharge creates one or more rapidly expanding vapor bubbles that generate the acoustic shock waves. These shock waves propagate radially outward and modify calcified plaque within the blood vessels. For treatment of an occlusion in a blood vessel, the voltage pulse applied by the power source 28 is typically in the range of from about five hundred to three thousand volts (500 V-3,000 V). In some implementations, the voltage pulse applied by the voltage source can be up to about ten thousand volts (10,000 V) or higher than ten thousand volts (10,000 V). The pulse width of the applied voltage pulses ranges between two microseconds and six microseconds (2-6 μs). The repetition rate or frequency of the applied voltage pulses may be between about 1 Hz and 10 Hz. The total number of pulses applied by the power source 28 may be, for example, sixty (60) pulses, eighty (80) pulses, one hundred twenty (120) pulses, three hundred (300) pulses, or up to five hundred (500) pulses, or other increments of pulses within this range. Alternatively, or additionally, in some examples, the power source 28 may be configured to deliver a packet of micro-pulses having a sub-frequency between about 100 Hz-10 kHz. The preferred voltage, repetition rate, and number of pulses may vary depending on, e.g., the size of the lesion, the extent of calcification, the size of the blood vessel, the attributes of the patient, or the stage of treatment. For instance, a physician may start with low energy shock waves and increase the energy as needed during the procedure, or vice versa. The magnitude of the shock waves can be controlled by controlling the voltage, current, duration, and repetition rate of the pulsed voltage from the power source 28.

In an alternative implementation, for laser generation of acoustic shock waves, the power source 28 generates a laser pulse that is transmitted into and absorbed by a fluid within the catheter. This absorption process rapidly heats and vaporizes the fluid, thereby generating the rapidly expanding vapor bubble, as well as the acoustic shock waves that propagate outward and modify the calcified plaque. The acoustic shock wave intensity is higher if a fluid is chosen that exhibits strong absorption at the laser wavelength that is employed. Accordingly, although some shock wave devices described herein generate shock waves based on high voltage pulses applied to electrodes, it should be understood that a shock wave device may additionally or alternatively use laser pulses transmitted through optical fibers to generate shock waves and that the "emitters" and "shock wave generating regions" described herein may include output ends of optical fibers. These examples are not intended to be a comprehensive list of potential energy sources to create shock waves in shock wave catheters.

To operate the catheter 100, a physician optionally inserts a guidewire into a body lumen. The physician then positions the elongated tube 12 over the proximal end of the guidewire such that the guidewire extends through the elongated tube 12 and uses the guidewire to guide the elongated tube 12 into position proximate to a lesion in a body lumen, such as a lesion in a blood vessel or a valve. Once positioned, the enclosure(s) can be filled with a conductive fluid through the fill port(s) 26, optionally such that the enclosure(s) inflates to contact the wall of the body lumen. As described further below, at least one of the emitters inside the enclosure(s) can be moved outward relative to the catheter's longitudinal axis to decrease the distance between the emitter(s) and the lesion. The power source 28 is then used to deliver one or more high voltage pulses to the emitters to create one or more shock waves within the enclosure(s) and within the body lumen being treated. The shock waves propagate generally outwardly toward the inner surface of the enclosure(s), through the material of the enclosure(s), and into a lesion in a body lumen proximate to the enclosure where the shock wave energy breaks up hardened plaque.

In some examples, the magnitude of the shock waves can be controlled by controlling the magnitude of the pulsed voltage, the current, the duration, and the repetition rate of the voltage supplied by the power source 28. Furthermore, in examples where one or more emitters are wired on separate circuits or separate circuit branches to be operated separately, a user of the catheter 100 may selectively emit shock waves at only a particular subset of emitters of the catheter by applying a voltage to generate shock waves at only that subset of the emitters. The physician may start with low energy shock waves and increase the energy as needed to disrupt the lesion and crack calcified plaques. In some examples, a physician may first generate shock waves at a first subset of emitters (e.g., a distal subset of emitters) and may continue treatment by generating shock waves at a second subset of emitters (e.g., a central or proximal subset of emitters). Repeated shock waves can be delivered, and the catheter 100 can be repositioned or advanced further in the body lumen to continue treatment. When the shock wave treatment is completed, the enclosure(s) can be deflated and the distal end 14 of the catheter 100 removed from the body lumen.

FIGS. 2A-2B, FIGS. 3A-3B, and FIGS. 4A-4C illustrate views of the distal end of various examples of catheter 100 that include expandable support structures for positioning at least one emitter closer to a lesion in a body lumen. The exemplary catheters 200A-D of FIGS. 2A-2B, FIGS. 3A-3B, and FIGS. 4A-4C each include an elongated tube 202 and an enclosure 252 sealed to a region of the elongated tube, optionally near its distal end at a seal 253. The enclosure 252 includes an enclosure distal end 254 and an enclosure proximal end 256 opposite the enclosure distal end. Catheters 200A-D include an expandable support structure 210A-D, various examples of which are shown in FIGS. 2A-2B, FIGS. 3A-3B, and FIGS. 4A-4C. In some examples, the catheters 200A-D additionally include a distal end tube 203 that is aligned with the longitudinal axis of the elongated tube 202 and connects with the distal end of the support structure 210A-D (e.g., a portion of the distal end tube 203 is visible in FIGS. 2A-2B). The distal end tube 203 may anchor the expandible support structure along the central longitudinal axis and may, in some examples, include a stopping mechanism for controlling expansion of the support structure, such as the stopping mechanism shown in FIGS. 5A-5B. At least one emitter (e.g., a first emitter 222, a second emitter 224, and a third emitter 226) is supported by the expandable support structure 210A-D. In a collapsed state, the expandable support structure 210A-D may have a relatively low profile. The expandable support structure 210A-D may be in the collapsed state during insertion of the catheter 200A-D and positioning of the catheter 200A-D in the body lumen. When the catheter 200A-D is positioned in a body lumen near a lesion and the enclosure is inflated with conductive fluid, the expandable support structure 210A-D can be expanded to a diameter greater than the diameter of the support structure in a collapsed state. For instance, the expandable support structure 210A-D could be expandable to a diameter of at least five millimeters (5 mm), at least eight millimeters (8 mm), or at least one centimeter (1 cm) from a collapsed diameter of no more than about one millimeter (1 mm). In some examples, the expanded diameter of the support structure is about four millimeters (4 mm), about five millimeters (5 mm), about six millimeters (6 mm), about seven millimeters (7 mm), about eight millimeters (8 mm), about ten millimeters (10 mm), or about twelve millimeters (12 mm). In some examples, the expanded diameter of the support structure is less than the inflated diameter of the enclosure 252, such as in order to prevent contact between the inner surface of the enclosure and the emitters 222, 224, 226. In one or more embodiments, when the support structure is expanded within the enclosure, the support structure is no less than three-fourths of a millimeter (0.75 mm) away from a wall of the enclosure. In some examples, when the support structure is expanded, the support structure is at least three-fourths of a millimeter (0.75 mm) away from a wall of the enclosure, or at least one centimeter (1 cm) away from a wall of the enclosure. In other examples, one or more of the emitters are movably connected to the elongated tube such that, in a first configuration, the at least one emitter is in a first position and, in a second configuration, the at least one emitter is in a second position. The second position may be no less than three millimeters (3 mm) farther from the central longitudinal axis than the first position. In other examples, the second position is no less than six millimeters (6 mm) or no less than one centimeter (1 cm) farther from the central longitudinal axis than the first position.

Figure 2A:
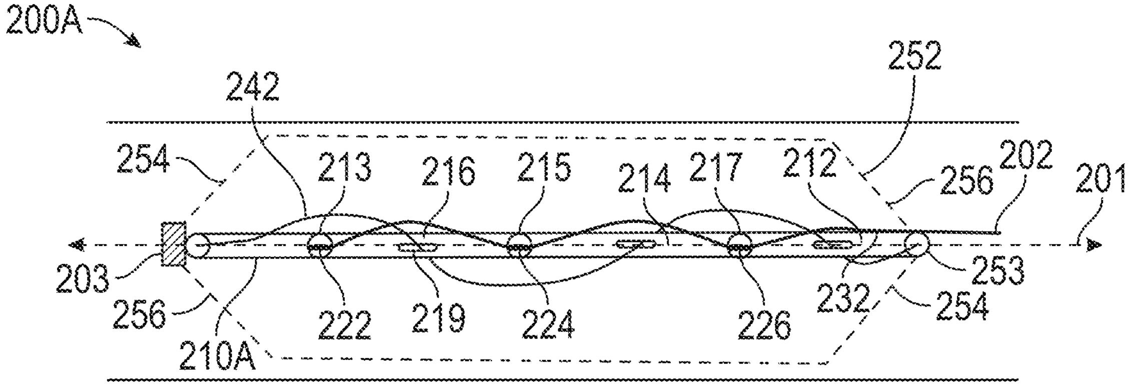
FIGS. 2A-2B illustrate the distal end of an exemplary shock wave catheter comprising a first expandable support structure, according to one or more aspects of the present disclosure.
Figure 2B:
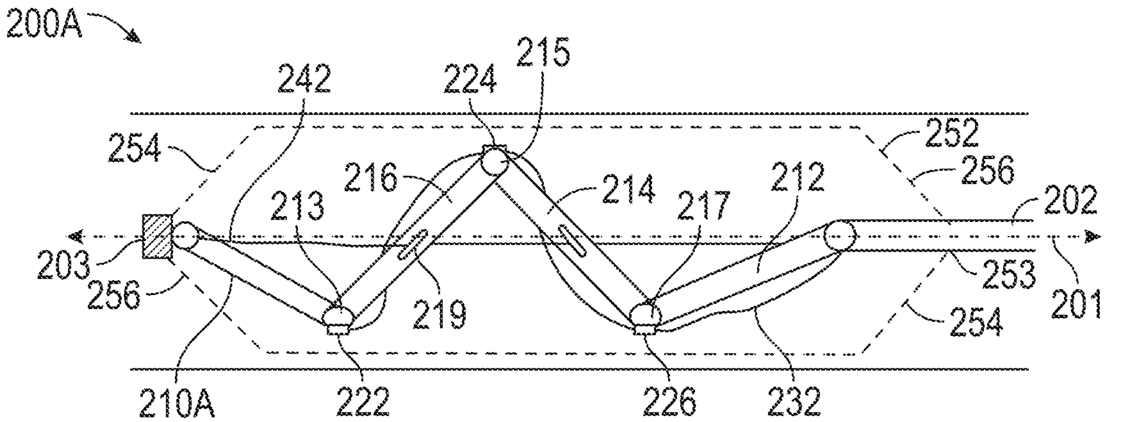

FIGS. 2A-2B illustrate the distal end of an exemplary catheter 200A that includes an example of an expandable support structure 210A. FIG. 2A illustrates the expandable support structure 210A in a collapsed state and FIG. 2B illustrates the expandable support structure 210A in an expanded state with the emitters 222, 224, 226 positioned farther from the central longitudinal axis and closer to the body lumen. The expandable support structure 210A includes a plurality of segments (e.g., a first segment 212, a second segment 214, a third segment 216, and a fourth segment 218) connected by respective joints (e.g., a first joint 213, a second joint 215, and a third joint 217) and at least one emitter disposed on the support structure.

When the support structure 210A is expanded, one or more of the respective joints 213, 215, 217 is configured to hinge, causing the joint and a portion of the adjacent segments to move outwardly relative to a longitudinal axis of the elongated tube. In a more particular example, the joints of the support structure may be configured to hinge in alternating directions such that the support structure expands in a zig zag or accordion shape, with successive segments of the support structure folding toward one another and pushing the joints outward from the central longitudinal axis. For instance, as seen in FIG. 2B, a first joint (e.g., 213) may move laterally in a first direction relative to the central longitudinal axis, while a second joint (e.g., 215) may move laterally in a second direction opposite the first direction. In such an example, a first emitter (e.g., 222) mounted proximate to first joint 213 may move laterally from the central longitudinal axis in the first direction, and a second emitter (e.g., 224) mounted proximate to a second joint 215 may move laterally from the central longitudinal axis in a second direction opposite the first direction.

The expandable support structure may be formed from a rigid material, such as a metal (e.g., stainless steel) or a rigid polymer. In some examples, at least a portion of the expandable support structure is formed from a compliant or semi-compliant material, such as a flexible polymer. For instance, each of the joints 213, 215, 217, a portion of the joints and/or a region proximate to the joints could be relatively more flexible than the segments (e.g., formed from a relatively more flexible material or otherwise modified to be more flexible), such that the support structure 210A is configured to bend at each of the joints when the structure is in an expanded state. In another example, each of the joints is a mechanical hinge connected to the adjacent segments of the support structure. In a particular example, one or more of the joints could be a living hinge, i.e., a thin flexible hinge made from the same material as the adjacent segments, and optionally a thinned region of the same material. In some examples, the segments 212, 214, 216, 218 may be formed from a relatively more rigid material than the joints.

In some examples, one or more of the segments 212, 214, 216, 218 includes a respective aperture 219 extending through the segment. The aperture 219 may be positioned approximately at the center of the segment such that the aperture aligns with the central longitudinal axis of the catheter 200A when the support structure 210A is in an expanded state. In one example, the expandable support structure 210A includes a series of apertures 219 on the plurality of segments, each aperture 219 positioned on a respective segment such that the central longitudinal axis of the catheter 200A (e.g., the central longitudinal axis of the elongated tube) extends through each of the apertures. In some examples, an elongate member 242, such as a wire, extends through one or more of the aperture(s) and, as described in further detail below, may be used to control the expansion of the support structure. In some examples, the elongate member 242 extends along the longitudinal axis.

In some examples, one or more emitters (e.g., emitter 222) are located (e.g., mounted) on the support structure 210A proximate or adjacent to one or more of the joints (e.g., disposed on one of the segments proximate to the joint, or disposed on or proximate to the joint itself). For instance, in the example of FIGS. 2A-2B, a first emitter 222 is located proximate to a first joint 213 of the support structure 210A, a second emitter 224 located proximate to a second joint 215 of the support structure 210A, and a third emitter 226 located proximate to a third joint 217 of the support structure 210A. In some examples, two or more emitters flank each of the respective joints of the support structure. In some examples, a first electrode of an emitter is located on a first segment of the support structure, and a second electrode of the emitter is located on a second segment of the support structure, such that a spark gap between the electrodes is near a joint of the support structure 210A. In some examples, the emitters are located on a region of the support structure that is farthest from the longitudinal axis and/or closest to the wall of the enclosure 252 when the support structure is in an expanded state. The emitters may be oriented such that shock waves generated from one or more of the emitters propagate outward from the central longitudinal axis of the catheter when the support structure 210A is in an expanded state.

The catheter 200A is illustrated with three emitters 222, 224, 226 located proximate to three joints 213, 215, 217 of the support structure 210A. However, this is provided for explanatory purposes only, and the catheter may include any number of emitters located within an enclosure. In some examples, for instance, additional emitters could be included in distal portion of the enclosure and oriented for forward-biased firing of shock waves.

Figure 3A:
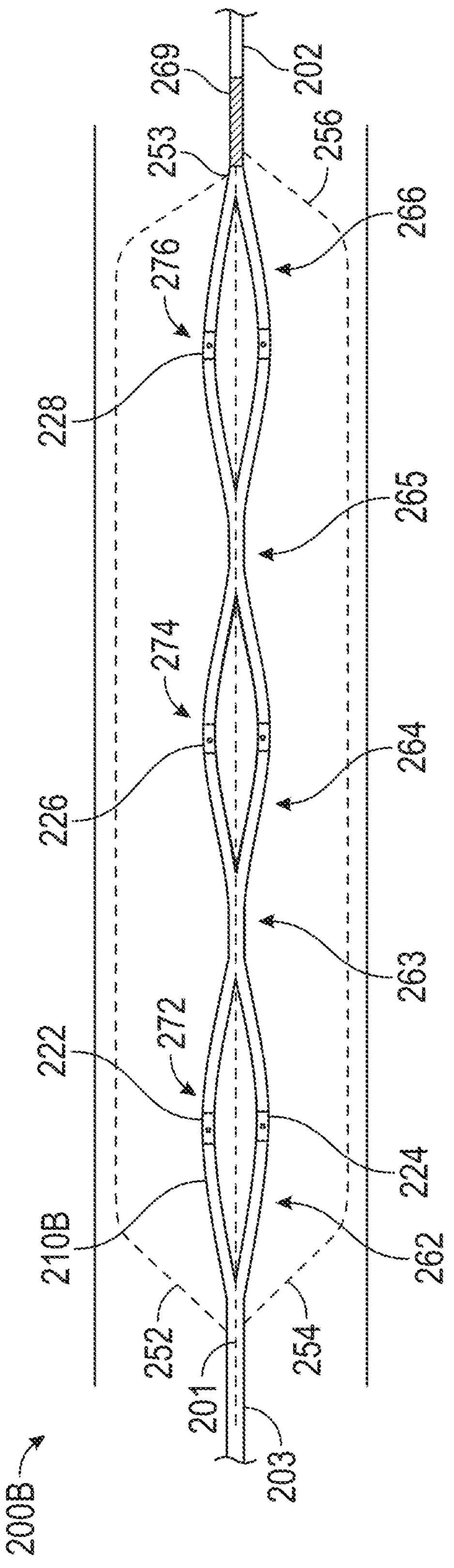
FIGS. 3A-3B illustrate the distal end of an exemplary shock wave catheter comprising a second expandable support structure, according to one or more aspects of the present disclosure.
Figure 3B:
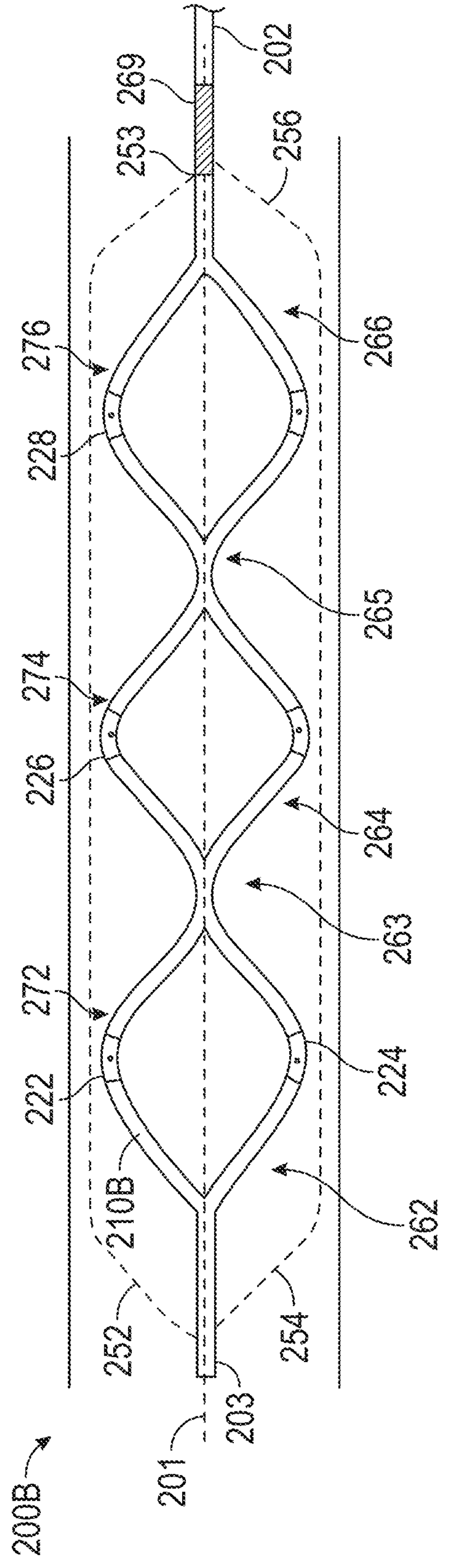

FIGS. 3A-3B illustrate the distal end of another exemplary catheter 200B that includes a second embodiment of an expandable support structure 210B. FIG. 3A illustrates the expandable support structure 210A-D in a collapsed state and FIG. 3B illustrates the expandable support structure 210A-D in an expanded state. The support structure 210B in catheter 200B expands laterally from the central longitudinal axis 201 of the catheter to move emitters (e.g., a first emitter 222, a second emitter 224, a third emitter 226, and a fourth emitter 228) disposed on the support structure laterally from the central longitudinal axis. In some embodiments, expanding the support structure 210B causes the emitters move three-dimensionally along one or more planes that intersect and are coplanar with the longitudinal axis.

The exemplary expandable support structure 210B includes a plurality of expanding regions (e.g., a first expanding region 262, a second expanding region 264, and a third expanding region 266), optionally connected by respective nodes (e.g., a first node 263, and a second node 265) between each of the respective expanding regions. However, an expandable support structure may include any number of expanding regions, such as a single expanding region, two expanding regions, three expanding regions, four expanding regions, or more than four expanding regions. Each of the expanding regions of the support structure may have one or more emitters disposed on the region. When the support structure 210B is in a collapsed state, each of the expanding regions and nodes may be substantially aligned with the central longitudinal axis of the catheter. When the support structure 210A-D expands, each of the nodes may move further together, causing the expanding regions to expand outwardly from the central longitudinal axis. In some examples, and as shown in FIG. 3B, each of the expanding regions 262, 264, 266 is configured to expand laterally in at least one transverse direction relative to the longitudinal axis. In some examples, each of the expanding regions is configured to expand laterally in a plurality of transverse directions relative to the central longitudinal axis.

In some examples, each of the expanding regions 262, 264, 266 includes a flexible joint (e.g., a first joint 272, a second joint 274, and a third joint 276) configured to hinge when the support structure 210B is in an expanded state. In some examples, one or more of the flexible joints is a living hinge, i.e., a thin flexible hinge made from the same material as the expanding region, and optionally a thinned region of the same material. In some examples, portions of the expanding regions 262, 264, 266 near the nodes 263, 265 are formed from a relatively more rigid material than portions of the expanding region near the joints. When the support structure 210B is expanded, each of the expanding regions 262, 264, 266 is configured to bend inwardly at a respective joint 272, 274, 276, causing the joint and at least one emitter located on the expandable support structure to move outwardly relative to a longitudinal axis of the elongated tube.

The support structure 210B may be formed of a flexible and resilient material that can be maneuvered through vasculature to the site of the shock wave treatment and can retain its shape after multiple expansions. For instance, the material of the support structure may be selected such that, after expanding the support structure, the support structure can return to substantially the same configuration in the collapsed state. In some examples, the material of the support structure can be repeatedly expanded and collapsed without deforming the shape of the material in the expanded or collapsed state. The expandable support structure may be formed from a compliant or semi-compliant material, such as a thin metal (e.g., stainless steel) or a compliant polymer. In some examples, at least a portion of the expandable support structure is formed from a flexible material, such as a flexible polymer.

In some examples, the material properties of the expandable support structure 210B bias the structure in either an expanded or collapsed state. For instance, the material of the expandable support structure may be biased such that in a natural or relaxed state, i.e., without external force applied to the support structure, the support structure is in either an expanded state or a collapsed state. Changing the state of the support structure (i.e., expanding or collapsing the support structure) may therefore include applying a force to the support structure. In some examples, collapsing or expanding the support structure includes applying an axial force on the support structure in either a proximal direction or a distal direction.

Optionally, the expandable support structure 210B includes one or more springs (e.g., 269) configured to bias the support structure in a collapsed or an expanded state. The spring(s) may exert an axial tension on the support structure to maintain the support structure in the collapsed or expanded state (e.g., by applying tension on one or more ends of the support structure in either a proximal or distal direction). In such examples, a user applies force against the spring to expand the support structure and move the emitters toward the wall of the balloon, or, alternatively, to compress the support structure into a longitudinal compressed state. In some examples, an elongate member 242 is operably coupled to a portion of the support structure may be used to apply an axial force on the support structure to control the expansion and compression of the support structure. In one or more examples, a spring is connected to a proximal end of the support structure to bias the support structure to a laterally collapsed state. In this configuration, a user applies force on the spring to change the configuration to a laterally expanded state. After treatment, the spring facilitates the return of the support structure to a collapsed state.

At least one emitter (e.g., a first emitter 222, a second emitter 224, a third emitter 226, and a fourth emitter 228) is disposed within the enclosure 252. One or more of the at least one emitter is supported by (i.e., located on and/or mounted on) the support structure 210B. Any number of emitters can be located on the support structure 210B and configured to move outwardly from the central longitudinal axis 201 when the support structure is expanded. The emitters 222, 224, 226, 228 may be located on the expanding regions 262, 264, 266 of the support structure and, optionally, proximate to the flexible joints 272, 274, 276. In some examples, the emitters 222, 224, 226, 228 are located on a region of the support structure that is farthest from the longitudinal axis and/or closest to the wall of the enclosure when the support structure 210B is in an expanded state.

In some examples, one or more emitters are located on adjacent expanding regions (e.g., expanding regions 262, 264) of the support structure and are configured to move outward in the same direction along a plane intersecting and coplanar with the central longitudinal axis, e.g., a first emitter 222 and a third emitter 226 expanding laterally in the same direction (depicted upwardly in FIGS. 2A, 2B, 3A, and 3B). In some examples, one or more emitters are located on the same expanding region (e.g., 262) and are configured to move laterally in opposing directions along a plane intersecting the central longitudinal axis (e.g., a first emitter 222 and a second emitter 224 expanding laterally in opposing directions, shown in the drawings as expanding in upward and downward directions, respectively).

In some examples, the emitters 222, 224, 226, 228 are located on the support structure 210A-D such that they move laterally from the central longitudinal axis 201 along multiple planes intersecting and coplanar with the longitudinal axis (e.g., to move a plurality of emitters outward from the central longitudinal axis in three dimensions). Advantageously, such a configuration would allow the catheter 200B to target lesions located around the circumference of a body lumen, or a larger circumferential area of the body lumen than could be targeted with a two-dimensionally expanding support structure. In some examples, the emitters are configured to move outwardly from the central longitudinal axis such that they are spaced evenly around the circumference of the enclosure and/or the body lumen. For instance, the emitters could be spaced approximately 30 degrees, 45 degrees, 60 degrees, 90 degrees, or 120 degrees apart around the circumference when the support structure 210B is in an expanded configuration. In such examples, the emitters may be configured to move along a plurality of planes that intersect with each other along the longitudinal axis, the respective planes oriented 30 degrees apart, 45 degrees apart, 60 degrees apart, 90 degrees apart, or 120 degrees apart relative to the central longitudinal axis of the catheter.

The catheter 200B in FIGS. 3A-3B is illustrated with six emitters located on a support structure having three expanding regions that move outward when the catheter is expanded, with one pair of emitters positioned on each of the expanding region. However, a catheter may have fewer than six emitters or greater than six emitters within the enclosure. For instance, in some examples, each expanding region 262, 264, 266 could include one emitter, three emitters, four emitters, six emitters, eight emitters, or greater than eight emitters. In some examples, the catheter includes one or more further emitter located near a distal tip of the expandable support structure.

Figure 4A:
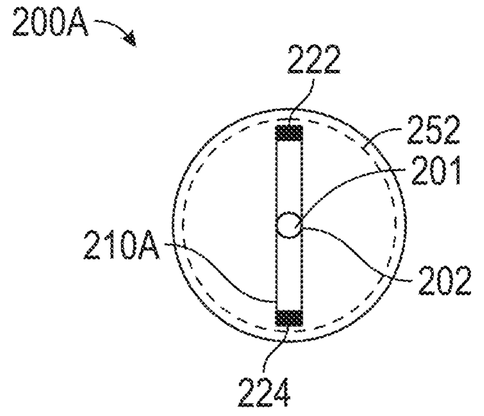
FIGS. 4A-4C illustrate cross-sectional views of the distal end of an exemplary shock wave catheter that includes an expandable support structure, according to one or more aspects of the present disclosure.
Figure 4B:
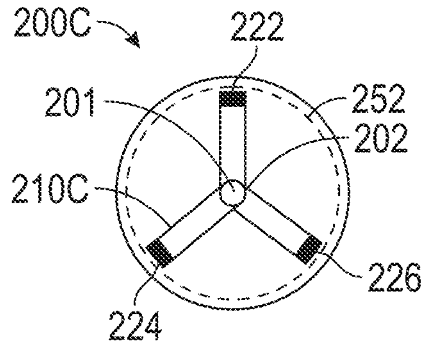
Figure 4C:
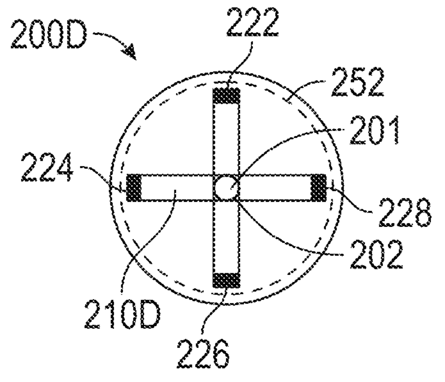

FIGS. 4A-4C illustrate various cross-sections of the distal end of exemplary catheters viewed along the central longitudinal axis 201 of the catheter, showing a variety of support structures 210A, 210C, 210D in an expanded state. FIG. 4A illustrates support structure 210A, for example the support structure of catheter 200A of FIG. 2A and 2B, which includes at least two emitters (e.g., a first emitter 222 and a second emitter 224), with the emitters spaced at 180 degrees apart around the circumference of an enclosure 252. FIG. 4B illustrates a support structure 210C of a catheter 200C that includes at least three emitters (e.g., a first emitter 222, a second emitter 224, and a third emitter 226), with the emitters spaced at 120 degrees around the circumference of the enclosure 252. FIG. 4C illustrates a support structure 210D of a catheter 200D, which includes at least four emitters (e.g., a first emitter 222, a second emitter 224, a third emitter 226, and a fourth emitter 228), with the emitters spaced 90 degrees apart around the circumference of the enclosure 252. However, as mentioned previously, a catheter can include any number of emitters, and the emitters may be configured to expand outward in any desired direction relative to the central longitudinal axis to position the emitters closer to the inner walls of the enclosure 252 and/or a lesion in a body lumen.

In the catheter 200A shown in FIG. 4A, expansion of the support structure 210A causes the emitters 222, 224 to move outwardly from the longitudinal axis in two opposing directions to position the emitters proximate to opposite sides of the wall of the enclosure 252. In some examples, the emitters move along a two-dimensional plane when the support structure is expanded (e.g., in two opposing directions along the same two-dimensional plane). In the exemplary catheter 200C of FIG. 4B, expansion of the support structure 210C causes three emitters 222, 224, and 226 to move outwardly from the central longitudinal axis 201 in three directions that are transverse relative to each other and the central longitudinal axis 201. In the exemplary catheter 200D of FIG. 4C, expansion of the support structure 210D causes four emitters 222, 224, 226, 228 to move outwardly from the longitudinal axis 201 in four directions. For instance, expansion of the support structure could move a first emitter 222 outward from the central longitudinal axis 201 along a first plane, and a second emitter 224 outward from the longitudinal axis along a second plane transverse to the first plane. In some examples, the first plane is perpendicular to the second plane, such that when the support structure 210A-D is expanded the first emitter 222 and second emitter 224 are positioned approximately 90 degrees apart relative to one another around the circumference of the enclosure 252 or a body lumen. However, in alternative examples, the planes may intersect at some other angle (e.g., a 30 degree angle, a 45 degree angle, a 60 degree angle, or 120 degree angle)

such that the first emitter 222 and second emitters are positioned approximately 30 degrees 45 degrees, 60 degrees, or 120 degrees apart relative to one another around the circumference of the enclosure or body lumen. In some examples, two or more of the emitters may move in the same or opposing directions along the same two-dimension plane that intersects the longitudinal axis 201. For instance, in a particular example, expansion of the support structure moves a first emitter 222 and a third emitter 226 in opposing directions along a first plane, and a second emitter 224 and a fourth emitter 228 in opposing directions along a second plane transverse to the first plane. In some examples, the first plane and the second plane are perpendicular. Additional or alternative emitter configurations are also anticipated.

In some examples, it may be favorable to position one or more of the emitters closer to a lesion by rotating the distal end of the catheter in a body lumen. As shown in FIGS. 4A-4C, in some examples the emitters are arranged such that expanding the support structure 210A-D moves the emitters closer to only a portion of the walls of the body lumen (e.g., only a particular side or two opposing sides of the lumen). In some examples, when in use, a physician may treat portions of the body lumen sequentially, such as by rotating the elongated tube 202 or elongate member 242 to cause the support structure 210A-D to rotate within the body lumen and position at least one emitter near a new portion of the walls of the body lumen. For instance, the physician may incrementally rotate the support structure 210A-D and emitters in a clockwise direction to treat the entire circumference of the body lumen during a shock wave treatment.

Power (e.g., a voltage) can be supplied to the emitters of any of catheters 200A-D by way of one or more conductive wires (e.g., insulated copper wires) that are electrically connected to at least one of the emitters inside the enclosure. However, as mentioned above, in other examples power may be supplied to the emitters by one or more optical fibers connected to at least one of the emitters. Returning to FIGS. 2A-2B, one or more conductive wires (e.g., a first wire 232 and a second wire 234) may extend along at least a portion of the elongated tube 202 and into the interior of the enclosure 252 to provide an electrical connection between the external power source and one or more of the emitters located on the support structure 210A-D. In some examples, the conductive wires 232, 234 may be folded within the enclosure when the enclosure is inserted and advanced through a body lumen.

In some examples, the conductive wires 232, 234 extend along at least a portion of the expandable support structure 210A-D (e.g., extend along the segments and/or the respective joints of the support structure of FIGS. 2A-2B, or along the expanding regions, joints, and/or nodes of the support structure of FIGS. 3A-3B). In some examples, the conductive wires 232, 234 are fixed to the expandable support structure at one or more points via, e.g., an adhesive. The conductive wires 232, 234 may optionally include some slack so that the wires do not provide physical resistance when expanding and collapsing the support structure 210A-D. The wire(s) 232, 234 may have slack when the support structure 210A-D is in a collapsed state and be relatively more taut when the support structure is in an expanded state. For instance, the wires 232, 234 could include additional length proximate to each of the joints of the support structure.

In other examples the conductive wire(s) 232, 234 extend freely within the enclosure 252 between one or more of the emitters and are not adhered or fixed to the support structure. In a further example, one or more of the conductive wires 232, 234 may be adhered to the inner surface of the enclosure 252. For instance, the conductive wires 232, 234 could extend along inner walls of the enclosure and optionally be coupled to the inner surface of the enclosure at one or more points along the inner surface via, e.g., an adhesive. In yet another example, at least a portion of the expandable support structure 210A-D could be conductive and configured to supply a voltage to one or more of the emitters. For instance, the support structure 210A-D could be formed from one or more conductive wires, or a conductive mesh covered by an insulating layer, and portions of the insulating layer can be removed from the support structure to provide one or more conductive portions that act as paired electrodes of an emitter.

In some examples, emitters are connected in series, such that a voltage pulse from the power source generates shock waves at all of the emitters as current flows across the spark gaps between respective electrodes of the emitters connected in series. The emitters may be connected in series in a particular order that is favorable for shock wave treatments. For instance, in some examples a voltage pulse from the voltage source causes current to flow through emitters in a more distal region of the enclosure first to generate shock waves to treat more distal portions of a lesion in a body lumen, before causing current to flow through emitters in a more proximal region of the enclosure to generate shock waves to treat more proximal regions of the body lumen.

In another example, one or more of the emitters may be wired on a separate circuit or a separate circuit branch, such that voltage pulses can be selectively applied to only a desired subset of emitters to generate shock waves at the desired subset. For instance, in one example one or more distal emitters could be wired together (i.e., wired in series) and in a separate circuit or circuit branch from another subset of emitters, such that shock waves can be selectively generated in a more distal portion of the balloon. In another example, emitters that move in a same direction or along a same plane relative to the longitudinal axis 201 may be wired together in a circuit or circuit branch, such that shock waves can be selectively generated on a certain side of the balloon, i.e., in order to treat a nonconcentric lesion located on a particular side of the body lumen. The emitters may be wired in a separate circuit or circuit branch from one or more further emitters configured to move outward in a different direction or along a different plane.

In some examples, the catheter includes an elongate member 242 that can be actuated by a user of the catheter to expand and collapse the support structure, for instance, any of the support structures shown in FIGS. 2A-2B, FIGS. 3A-3B, and FIGS. 4A-4C and described herein. After positioning the catheter 200A-D in the body lumen and inflating the enclosure 252, a user of the catheter can move the elongate member 242 in a proximal or distal direction to expand the support structure 210A-D to an expanded diameter and position the emitters closer to the lesion in a body lumen. After completing a shock wave treatment, the user can move the elongate member 242 in either the proximal or distal direction to collapse the support structure 210A-D and the catheter 200A-D can be removed from the body lumen.

An exemplary elongate member 242 is shown in FIGS. 2A-2B, however, an elongate member may be used to expand any of the support structures shown in FIGS. 2A-2B, 3A-3B, and 4A-4C and described herein. The elongate member 242 extends along the longitudinal axis 201 of the elongated tube of the catheter and optionally through at least a portion of the enclosure 252 and/or the support structure 210. In some examples, such as the catheter 200A shown in FIGS. 2A-2B, the support structure 210A includes one or more apertures 219, and the elongate member 242 extends through one or more of the apertures. The elongate member 242 may extend approximately in line with the longitudinal axis 201 of the catheter, such that movement of the elongate member in a proximal or distal direction by a user of the catheter does not produce a moment arm with respect to the longitudinal axis 201.

The elongate member 242 could be any suitable elongated component that extends along the length of the catheter 200A-D between the support structure 210A-D near the catheter's distal end and a proximal end of the catheter external to the body lumen, where the elongate member can be actuated by a user of the catheter. For instance, in some examples the elongate member 242 includes a flexible tube or a shaft and moving the flexible tube or shaft in a proximal or distal direction causes the support structure to expand or contract. The flexible tube or shaft may surround at least a portion of the elongated tube, such that movement of the flexible tube or shaft in a proximal or distal direction relative to the elongated tube causes expansion of the support structure. In a particular embodiment, the elongate member 242 includes an inner shaft and an outer shaft concentric with and at least partially surrounding the inner shaft. In such an example, movement of the outer shaft in a proximal or distal direction relative to the inner shaft causes the support structure 210A-D to expand or contract. In yet a further example, and as shown in FIGS. 2A-2B, the elongate member 242 could include a wire, and pulling the wire in a proximal direction causes expansion of the support structure 210A-D.

In some examples the expanded diameter of the support structure 210A-D can be controlled by moving the elongate member 242 by variable amounts in the proximal direction or the distal direction. For instance, moving the elongate member 242 by a first amount may expand the support structure 210A-D to a first expanded diameter, and moving the elongate member by a second amount may expand the diameter to a second expanded diameter. In such examples, visual indicators may be provided on the elongate member 242 or another portion of the catheter 200A-D to aid a user in expanding the support structure 210A-D to a desired member by moving the elongate member in accordance with the visual indicators. In some examples, for instance, the elongate member 242 includes one or more markings that indicate to a user an amount of movement of the elongate member associated with one or more expanded diameters of the support structure 210.

Advantageously, controlling the expanded diameter of the support structure 210A-D may allow the catheter 200A-D to access and/or treat regions of a body lumen that have relatively larger or smaller diameters. For instance, the catheter 200A-D can be advanced through relatively narrower vasculature before being positioned proximate to a relatively larger vessel or valve, and the support structure 210A-D can then be expanded to a desired size to treat the vessel or valve. In certain cases, a single shock wave treatment includes the treatment of body lumens having different diameters or having lesions of different morphology. For example, adjusting the diameter of the support structure may be favorable for treating eccentric or nodular calcified lesions or more fully occluded regions of vasculature. In such circumstances, the expanded diameter of the support structure may be controlled during a shock wave treatment (i.e., when the catheter is positioned with a body lumen) to control the position of the emitters closer to a lesion in the body lumen. Providing a support structure with a controllable diameter may also advantageously make the support structure compatible with catheters having enclosures (e.g., angioplasty balloons) of a variety of different diameters. Additional advantages are also anticipated.

In examples where the expanded diameter of the support structure 210A-D is controllable or adjustable, the support structure may nevertheless have a maximum expanded diameter. Overexpansion of the support structure may risk rupturing the enclosure or damaging a wall of a body lumen when the catheter is positioned in situ. To mitigate the risk of overexpansion, in some examples expanding the support structure to a particular expanded diameter causes the support structure to reversibly lock in the expanded state. For instance, in the exemplary catheter 200B of FIGS. 3A-3B, one or more of the segments could include overlay arms that prevent overexpansion of the support structure 210. A user of the catheter 200B can then, e.g., push a button or actuate the elongate member 242 in a proximal or distal direction to unlock the expandable support structure 210B and collapse the support structure before removing it from the body lumen.

Figure 5A:
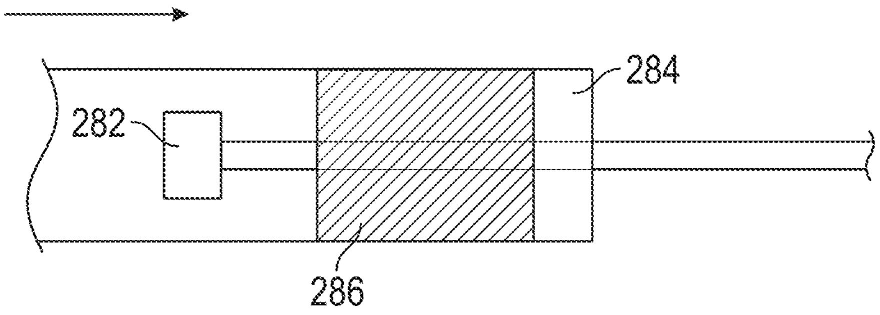
FIGS. 5A-5C illustrate a distal end of an exemplary shock wave catheter including a first stop and a second stop, according to one or more aspects of the present disclosure.
Figure 5B:
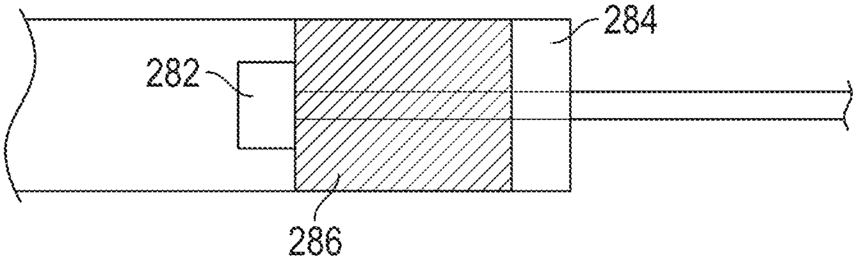
Figure 5C:
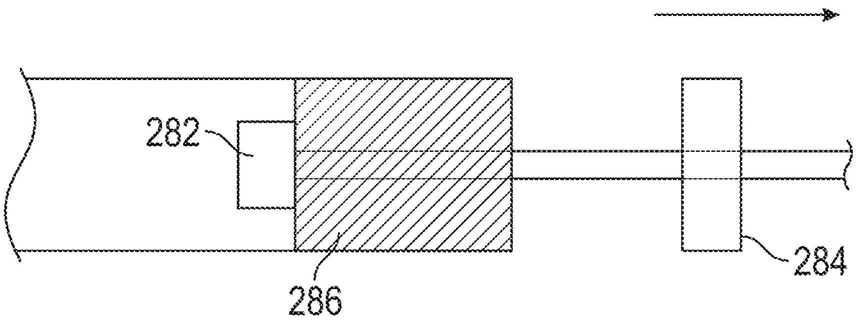

In some examples, the catheter includes a first stop and a second stop and expanding the support structure comprises moving the first stop relative to the second stop. FIGS. 5A-5C illustrate one exemplary configuration of a first stop 282 and a second stop 284 for controlling the expansion and collapsing of the support structure of a catheter. For instance, moving the first stop in a direction toward the second stop could cause the support structure to expand outward relative to the longitudinal axis of the catheter, and moving the first stop in a direction away from the second stop could cause the support structure to collapse closer to the longitudinal axis. The first and second stops 282, 284 may be configured to move axially along a longitudinal axis of the catheter and may be controllable via the axial movement of the elongate member (e.g., the elongate member 242 shown in FIGS. 2A-2B.

In some examples, the first stop 282 and the second stop 284 are spaced apart in a collapsed state of the support structure 210A-D and abutting in an expanded state of the support structure. However, in other examples and as shown in FIGS. 5A-5C, the first stop 282 and the second stop 284 are separated by a spacing element 286, such that one or more of the first stop 282 and the second stop 284 are spaced apart from the spacing element when the support structure is in a collapsed state, and both the first stop 282 and the second stop 284 abut the spacing element 286 when the support structure is in an expanded state. FIG. 5A shows the first stop 282 spaced apart from the spacing element 286 and the second stop 284 abutting the spacing element 286 while the support structure is in a collapsed state. Expanding the support structure 210A-D could therefore include moving the first stop 282 to abut the spacing element 286 and/or moving the first stop 282 closer to the second stop 284. When the first stop 282 is abutting the spacing element 286, as seen in FIG. 5B, the support structure 210A-D is fully expanded. However, note that either the first stop 282 or the second stop 284 could be moved relative to the other stop and the spacing element 286 (and in either a proximal or a distal direction) to cause the support structure 210A-D to expand or contract. As mentioned above, the extent of expansion of the support structure 210A-D (i.e., the expanded diameter of the support structure) may be controlled by moving the first stop 282 and the second stop 284 a relatively greater or lesser amount relative to one another. In some examples, to collapse the support structure, 210A-

D, the second stop 284 is moved farther from the first stop 282 and/or the spacing element 286.

In such examples, the elongate member 242 is operably coupled to at least one of the first stop 282 and the second stop 284, such that movement of the elongate member 242 moves the first stop relative to the second stop and causes the support structure to expand and/or collapse. For instance, in examples where the elongate member 242 is a wire, the wire may extend between and be operably coupled to at least one of the first stop 282 and the second stop 284. Movement of the wire (e.g., pulling the wire) in a proximal direction could cause expansion of the support structure, e.g., by moving a first stop 282 operably coupled to the wire closer to a second stop 284 or a spacing element 286 that remains stationary on the catheter. In another example, the elongate member 242 could be a flexible tube or a shaft that is operably coupled to at least one of the first stop and the second stop such that moving the flexible tube or shaft in a proximal or distal direction causes the first stop 282 to move relative to the second stop 284 and the support structure 210A-D to expand. In another example, a first shaft is operably coupled to the first stop 282 and a second shaft at least partially surrounding the first shaft is operably coupled to the second stop 284, such that moving the first shaft relative to the second shaft causes the first stop to move relative to the second stop and the support structure to expand.

In some examples, one or more of the first stop 282 and second stop 284 are included in a portion of the support structure 210. For instance, the first stop 282 could be a first joint of the support structure, and a second stop 284 could be a second joint of the support structure 210, such that the support structure can be expanded by pulling a first joint of the support structure closer to a second joint of the structure. Alternatively, the first stop 282 and the second stop 284 could be included in a portion of the catheter located proximal to or distal to the enclosure and the expandable support structure. For instance, the first stop 282 and the second stop 284 may be included in portion of the elongated tube, or in another location of the catheter (e.g., a handle).

In some examples, a shock wave catheter includes multiple enclosures at its distal end, and inflation of the various enclosures can be used to position a desired emitter or grouping of emitters closer to a body lumen. FIGS. 6A-6C and FIGS. 7A-7C illustrate the distal end of various exemplary shock wave balloon catheters 300A-C having various multi-balloon arrangements for positioning at least one emitter closer to a lesion in a body lumen. The catheters 300A-C are examples of catheter 100 shown in FIG. 1.

When the catheter 300A-C is advanced through a body lumen and positioned proximate to a lesion in a body lumen, one or more of the enclosures can be inflated with conductive fluid such that at least one of the enclosures contacts a body lumen. The relative expansion of the enclosures can be used to modulate the distance between the emitter(s) and the body lumen and to position at least one emitter proximate to a lesion in the body lumen. After the enclosures have been inflated, one or more shock waves can be generated at the emitter(s) to treat the lesion. When the shock wave treatment has been completed, each of the enclosures can be deflated and the distal end of the catheter 300A-C removed from the body lumen.

Figure 6B:
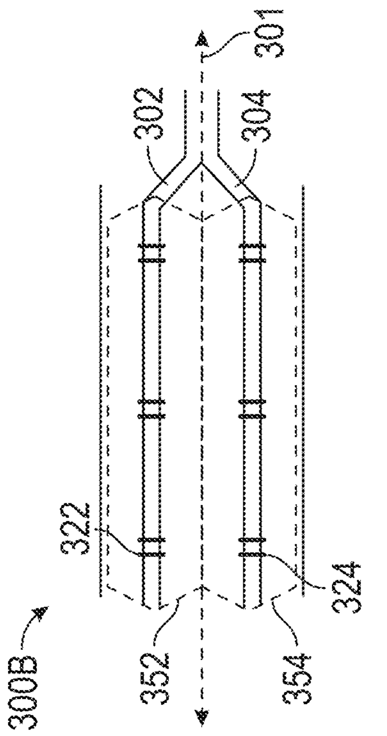
FIGS. 6A-6C illustrate cross-sectional views of the distal end of various exemplary shock wave catheters that includes two or more enclosures, according to one or more aspects of the present disclosure.
Figure 6A:
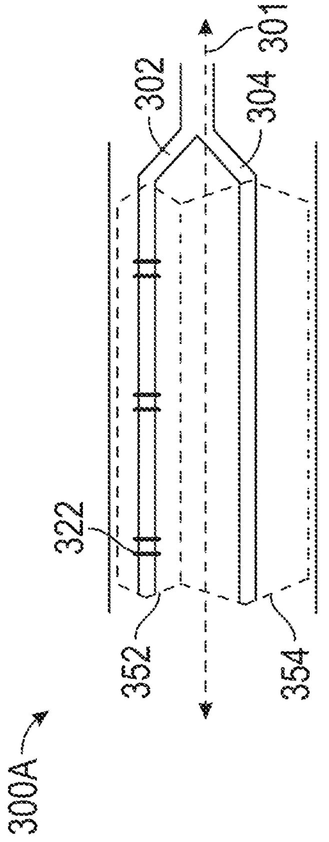
Figure 6C:
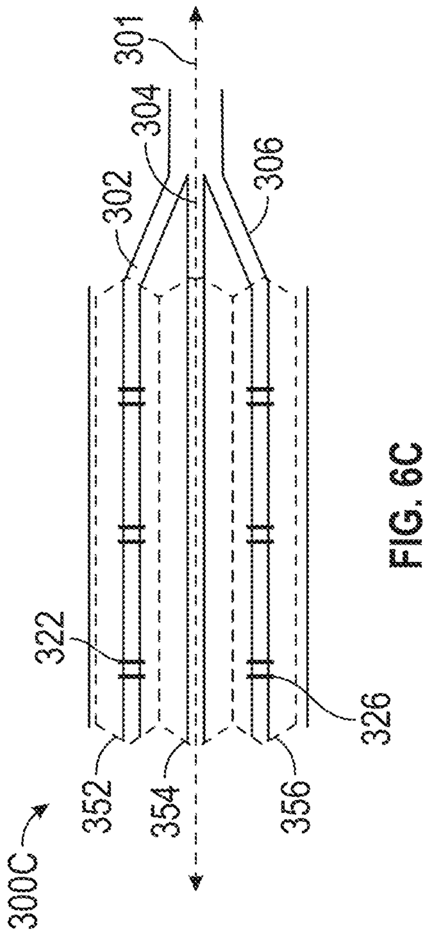
Figure 7A:
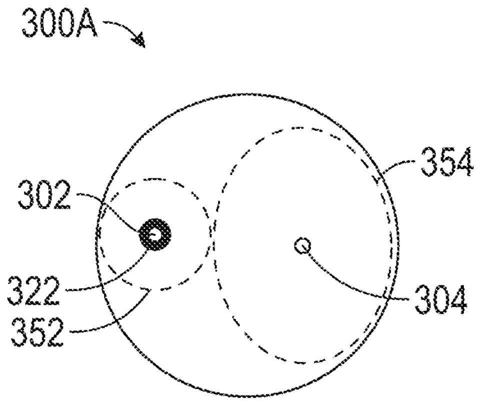
FIGS. 7A-7C illustrate cross-sectional views of the distal end of various exemplary shock wave catheter that includes two or more enclosures, according to one or more aspects of the present disclosure.
Figure 7B:
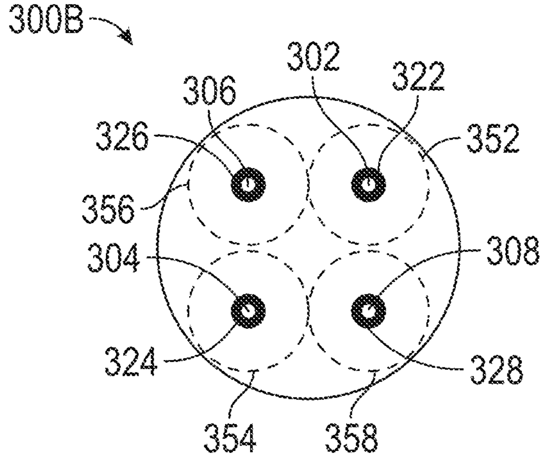
Figure 7C:
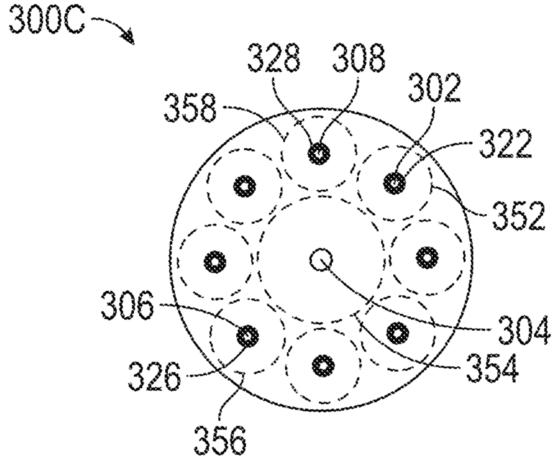

FIGS. 6A-6C illustrate side cross-sectional views of various exemplary multi-balloon shock wave catheters 300A-C, and FIGS. 7A-7C illustrate axial or longitudinal cross-sectional views of the exemplary catheters 300A-C. The catheters 300A-C include at least one elongated tube and multiple enclosures, e.g., a first enclosure 352 and at least one further enclosure, optionally with one or more of the enclosures sealed to a region of a first elongated tube 302 or a further elongated tube (e.g., a second elongated tube 304 or a third elongated tube 306). In some examples, the first elongated tube 302 defines a central longitudinal axis 301 of the catheter 300. However, in other examples the first elongated tube 302 is offset from the longitudinal axis 301 of the catheter. As described below, in some examples a catheter 300A-C includes two or more elongated tubes (e.g., a second elongated tube 304, a third elongated tube 306 and/or a fourth elongated tube 308), with the plurality of elongated tubes providing, e.g., fluid inlets, conductive wires, and other connections to each of the multiple enclosures. In such examples, one or more of the tubes may align with the longitudinal axis 301 of the catheter. In a distal region of the catheter 300, one or more of the elongated tubes 302, 304, 306, 308 may be offset from the longitudinal axis 301 and extend into an enclosure that is offset from the axis. In a further example, and as shown in FIGS. 6A-6B, an elongated tube of the catheter may fork at its distal end to form one or more further elongated tubes (e.g., a first elongated tube 302, a second elongated tube 304, a third elongated tube 306, and a fourth elongated tube 308) that extend into one or more enclosures provided at the catheter's distal end.

A first enclosure 352 surrounds at least one emitter 222 disposed within the enclosure and is fillable with conductive fluid to form an annular channel around the elongated tube where the at least one emitter can generate shock waves within the conductive fluid. Optionally, the first enclosure 352 is sealed to a region of the first elongated tube 302. The first enclosure 352 (and any further enclosures, such as a second 354, third 356, and/or fourth 358 enclosure), as described above, could be an angioplasty balloon and could be configured to inflate to contact the walls of the body lumen. However, in other examples, the material of the first and/or further enclosures could be thicker than a conventional angioplasty balloon or configured to expand a relatively lesser amount than a conventional angioplasty balloon.

At least one emitter 322 is configured to generate shock waves inside the first enclosure 352 when power is supplied to the at least one emitter. Each of the emitters may include at least one electrode pair, with the electrodes of each pair spaced apart from one another to form a spark gap between the electrodes across which shock waves can be generated. However, as described previously, an emitter could also include an optical fiber configured to transmit energy from a laser source to generate shock waves. Optionally, the at last one emitter is located to a region of the first elongated tube 302 and may be adhesively attached to the tube by way of an adhesive, such as a glue or some other adhesive material. In one or more examples, the at least one emitter is oriented to generate shock waves outwardly from a longitudinal axis 301 of the catheter in a direction toward the inner surface of the enclosure and the lesion in the body lumen.

While the catheters 300A-C shown in FIGS. 6A-6C and 7A-7C include at least three pairs of emitters located on respective elongated tubes (e.g., emitters arranged as a proximal pair, a central pair, and a distal emitter pair) such a catheter could include any number of emitters disposed within an enclosure and optionally located on an elongated tube. In one or more examples, the emitters include more than three or less than three emitters, or more than six or less than six emitters. However, even greater numbers of emitters are also anticipated (e.g., eight emitters or ten emitters). Further, as mentioned above, a catheter could include one or more further elongated tubes (e.g., a second elongated tube 304, a third elongated tube 306, and/or a fourth elongated tube 308) extending into one or more further enclosures, with at least one further emitter disposed inside the one or more further enclosures and located on the one or more further elongated tubes.

In various examples, an exemplary multi-balloon shock wave catheter 300A-C could include one or more further enclosures, such as a second enclosure 354, a third enclosure 356 and/or a fourth enclosure 358. For example, FIGS. 6A-6C and FIGS. 7A-7C illustrate the distal end of exemplary shock wave catheters including a first enclosure 352 and at least one further enclosure (e.g., a second enclosure 354, a third enclosure 356, and/or a fourth enclosure 358). The multiple enclosures of the catheter can be arranged such that when the catheter 300A-C is positioned in a body lumen, the first enclosure 352 and any further enclosures extend laterally to each other and abutting within the body lumen. Each of the enclosures 352, 354, 356, 358 are fillable with a conductive fluid, such that the enclosures expand to provide an annular channel between an inner surface of the enclosures and emitters included within the enclosures. When the first enclosure 352 and further enclosures are inflated within the body lumen, at least a portion of the first enclosure (i.e., a first emitter-containing enclosure) contacts a wall of the body lumen. The inflation of the further enclosures within the body lumen applies a force against the first enclosure 352 that pushes the first enclosure (and the at least one emitter 322 within the first enclosure) toward a wall of the body lumen. Accordingly, the relative inflation of the first enclosure 352 and the further enclosure(s) (e.g., a second enclosure 354, third enclosure 356, fourth enclosure 358 and/or further enclosure) can be used to modulate the distance between emitters within the enclosures and a lesion within the body lumen.

The catheters 300A-C can be configured such that when the enclosures are inflated, at least one of the enclosures contacts the body lumen and/or an occluded region of the body lumen. In some examples, the enclosures may be configured to expand such that, when the enclosures are inflated, a channel is provided between two or more of the enclosures to maintain a certain amount of fluid flow through the body lumen (e.g., to maintain a level of blood flow through vascular in which the catheter has been positioned). Advantageously, maintaining an amount of fluid flow through the body lumen may allow for longer-duration shock wave treatments without risking, e.g., ischemia. For instance, when the enclosures are inflated, the flow rate of fluid through the channel could be approximately 50% of the rate of fluid flow through the body lumen without the catheter 600 placed in the body lumen (i.e., the "normal flow rate"). In one or more examples, the flow rate of fluid through the channel may be less than 50% of the normal flow rate, such as 10%, 15%, or 20% of the normal flow rate. In one or more examples, the flow rate of fluid through the channel may be more than 50% of the normal flow rate, such as 70%, 80%, or 90% of the normal flow rate.

The volumes of the various enclosures of the catheter 300A-C may be separate from one another (i.e., not in fluid connection), such that the enclosures can be inflated and deflated independently by, e.g., by flowing conductive fluid into one or more of the enclosures by way of a fluid lumen extending into the enclosure(s). However, in other examples, one or more channels or orifices may permit fluid to flow between the enclosures, such that the volumes of the enclosures are fluidly connected, and the enclosures can be inflated together by flowing conductive fluid into a single enclosure. In one or more related examples, a multi-balloon catheter 300A-C may instead incorporate a single enclosure that is sealed to the elongated tube and includes multiple lobes, e.g., a two-lobed, a tri-lobe, or a four-lobe configuration. In such an example, inflation of the lobes of the enclosure may position the emitter(s) within the enclosure closer to a lesion in the lumen. Optionally, emitters are included in two or more portions of the single enclosure, e.g., located on two or more tubes extending in two or more portions of a single enclosure, or located at two axially spaced positions along a single elongated tube.

The first enclosure 352 and the further enclosures (e.g., a second enclosure 354, a third enclosure 356, a fourth enclosure 358, or a further enclosure) may be independently fillable with conductive fluid, such that the extent of inflation of each of the enclosures is independently controllable to position a desired emitter(s) closer to the lesion in the body lumen. For instance, to position an emitter in the first enclosure 352 closer to the emitter, a second 354 or further enclosure could be inflated with a relatively greater amount of conductive fluid to expand and push the first enclosure 352 and the emitter(s) 322 contained therein closer to the body lumen.

To permit independent inflation of each of the enclosures with conductive fluid, in some examples the elongated tube(s) of the catheters 300A-C provide a plurality of channels for carrying conductive fluid (i.e., one or more fluid lumens), each channel of the plurality for filling a different enclosure with conductive fluid. In such examples, each of the enclosures may be sealed to a region of an elongated tube in fluid connection with at least one of the channels. For instance, in some examples, an elongated tube of the catheter includes a first channel for introducing conductive fluid into a first enclosure and a second channel for introducing conductive fluid into a second enclosure. However, any number of channels can be provided in an elongated tube for filling any number of enclosures at the distal end of the catheter.

Additionally or alternatively, an exemplary catheter 300A-C could include two or more elongated tubes (e.g., an elongated tube 302 and at least one further elongated tube, such as a second elongated tube 304, a third elongated tube 306 and/or a fourth elongated tube 308), with each of the plurality of enclosures sealed to a different elongated tube that provides an independent fluid lumen for introducing conductive fluid to inflate each of the respective enclosures. For instance, a catheter 300A-C could include a first elongated tube 302 and a second elongated tube 304 offset from the longitudinal axis of the catheter. The first elongated tube 302 could be sealed to a first enclosure 352 and configured to introduce fluid into the first enclosure, while the second elongated tube 304 is sealed to a second enclosure 354 and is configured to introduce fluid into the second enclosure. In some examples, the first and/or further elongated tubes extend outwardly from the central longitudinal axis of the catheter near the distal end of the catheter 300A-C before extending into one or more enclosures offset from the central longitudinal axis. In examples including a central enclosure and one or more peripheral enclosures, a central elongated tube may extend into the central closure, with one or more peripheral elongated tubes extend into one or more of the peripheral enclosures. In examples without a central enclosure, an elongated tube of the catheter may fork into a plurality of elongated tubes near the distal end of the catheter and before extending into the enclosures. In some examples, of the forked distal region forming the plurality of elongated tubes shares one or more aspects of the proximal region of the elongated tube (i.e., such that one or more of the lumens or channels of the elongated tube continues into the forked region) and extends those aspects into the various enclosures at the distal end.

In some examples, at least one emitter is included in one or more of the further enclosures of the catheter. For instance, the first enclosure 352 may surround a first emitter 322 of the at least one emitter, while a second enclosure 354 surrounds a second emitter 324 of the at least one emitter. A third enclosure 356 may surround a third emitter 326 of the at least one emitter, and a fourth enclosure 358 or further enclosure may surround a fourth emitter 328 or further emitter of the at least one emitter. Such a configuration advantageously allows the multi-balloon shock wave catheter to generate shock waves in more than one of the enclosures, permitting treatment of lesions located in various portions of the circumference of a body lumen. Like the first emitter 322 of the first enclosure 352, the second emitter 324, third emitter 326, fourth emitter 328, and/or further emitters can be located on an elongated tube and moved closer to a lesion in a body lumen by controlling the relative inflation of the first enclosure 352, second enclosure 354, third enclosure 356, fourth enclosure 358, and/or any further enclosures. Similarly, each of the first, second, third, fourth, and further emitters could include a single emitter, or a plurality of emitters disposed in one or more of the first, second, third, fourth, and/or further enclosure.

In some examples, at least one emitter is disposed on one or more of the elongated tubes that extend into a further (e.g., a second, third, fourth, or further) enclosure of the catheter. For instance, a first emitter 322 of the at least one emitter could be located on a first elongated tube 302 extending inside the first enclosure 352, and a second emitter 324 of the at least one emitter could be located on the second elongated tube 304 extending inside the second enclosure 354. A third emitter 326 of the at least one emitter could be mounted to a third elongated tube 306 extending inside a third enclosure 356, and a fourth emitter 328 of the at least one emitter could be mounted to a fourth elongated tube 308 extending inside the fourth enclosure 358. Additional configurations are also anticipated for positioning one or more emitters in multiple enclosures of a catheter.

FIGS. 6A-6C illustrate the distal ends of various exemplary multi-balloon shock wave catheters having two, four, and a plurality of enclosures, respectively. FIGS. 7A-7C provide cross-sections of the distal ends to show the configuration of the enclosure of the respective catheters.

FIGS. 6A and 7A illustrate the distal end of a first exemplary shock wave 300A catheter positioned in a body lumen. The exemplary catheter includes a first enclosure 352 and a second enclosure 354. The first enclosure 352 is sealed to a first elongated tube 302 and surrounds at least one emitter 322. The first elongated tube 302 extends into the first enclosure 352, with at least one emitter 322 disposed on the first elongated tube and configured to generate shock waves inside the first enclosure. In some examples, the first elongated tube 302 includes a fluid lumen for inflating the first enclosure 352 with conductive fluid. The second enclosure 354 does not surround any emitters. In some examples, the second enclosure 354 is sealed to a second elongated tube 304 that includes an independent fluid lumen for inflating the second enclosure 354 with conductive fluid.

When the distal end of the catheter 300A is advanced through a body lumen and positioned near a lesion in the body lumen, the first enclosure 352 and the second enclosure 354 can be inflated with conductive fluid to expand the enclosures to contact a portion of the body lumen. As seen in FIG. 6A, when the catheter 300A is positioned in a body lumen, the second enclosure 354 extends lateral to and abutting the first enclosure 352, such that inflation of the second enclosure applies a force against the first enclosure to push the first enclosure toward the wall of the body lumen. In the catheter shown in FIG. 6A, expansion of the second enclosure 354 while the catheter 300A is disposed within the body lumen moves the at least one emitter 322 in the first enclosure 352 farther from the central longitudinal axis 301 and closer to one side of the body lumen than before expansion.

FIG. 7A provides a cross-sectional view of the first exemplary shock wave catheter 300A shown in FIG. 6A. As seen in FIG. 7A, expansion of the second enclosure 354 within the body lumen exerts a force on the first enclosure 352 to move the first enclosure (and the elongated tube 302 and emitters 322 included within) away from the longitudinal axis of the catheter 300 and toward a wall of the body lumen. Accordingly, relatively greater expansion of the second enclosure 354 (and/or relatively lesser expansion of the first enclosure 352) may cause the at least one emitter 322 to be positioned farther from the central longitudinal axis and closer to the body lumen, while relatively greater expansion of the first enclosure 352 (and/or relative lesser expansion of the second enclosure 354) may cause the at least one emitter 322 to be positioned farther from the body lumen. Shock waves can be generated at the at least one emitter 322 in the first enclosure 352 to selectively treat a region of the body lumen that is closest to the first enclosure.

FIGS. 6B and 7B illustrate the distal end of a second exemplary shock wave catheter 300B positioned in a body lumen. The exemplary catheter 300B includes a first enclosure 352, a second enclosure 354, a third enclosure 356, and a fourth enclosure 358. Each of the first, second, third, and fourth enclosures are sealed to a respective elongated tube and surrounds at least one emitter configured to generate shock waves in the enclosure. More specifically, the first enclosure 352 is sealed to a region of a first elongated tube 302 and surrounds a first emitter 322, the second enclosure is sealed to a region of a second elongated tube 304 and surrounds a second emitter 324, the third enclosure 356 is sealed to a region of a third elongated tube 306 and surrounds a third emitter 326, and the fourth enclosure 358 is sealed to a region of a fourth elongated tube 308 and surrounds a fourth emitter 328.

The first elongated tube 302 extends into the first enclosure 352, with a first emitter 322 mounted on the elongated tube and configured to generate shock waves inside the first enclosure. The second elongated tube 304 extends into the second enclosure 354, with a second emitter 324 mounted on the second elongated tube and configured to generate shock waves inside the first enclosure. The third elongated tube 306 extends into the third enclosure 356, with a third emitter 326 mounted on the third elongated tube and configured to generate shock waves inside the third enclosure. The fourth elongated tube 308 extends into the fourth enclosure 358, with a fourth emitter 328 mounted on the fourth elongated tube and configured to generate shock waves inside the fourth enclosure. Each of the first, second, third, and fourth elongated tubes optionally includes a respective first, second, third, or fourth fluid lumen for independently inflating the respective first, second, third, and fourth enclosures with conductive fluid.

When the distal end of the catheter 300B is advanced through a body lumen and positioned near a lesion in the body lumen, the first enclosure 352, second enclosure 354, third enclosure 356, and fourth enclosure 358 can be inflated with conductive fluid to expand the enclosures to contact a portion of the body lumen. As seen in FIG. 7B, when the catheter 300B is positioned in a body lumen, the first, second, third, and fourth enclosures extend laterally within the body lumen laterally and abutting at least one adjacent enclosure, such that inflation of one of the enclosures applies a force against the adjacent enclosures to push the adjacent enclosures toward the wall of the body lumen. In the catheter 300B shown in FIG. 7B, expansion of any one of the enclosures while the catheter is disposed within the body lumen will move at least one emitter disposed in the other enclosures closer to the lesion.

FIG. 7B provides a cross-sectional view of the second exemplary shock wave catheter 300C shown in FIG. 6B. As seen in FIG. 7B, expansion of any of the first enclosure 352, second enclosure 354, third enclosure 356, or fourth enclosure 358 within the body lumen will exert a force on the other enclosures to move the enclosures (and the elongated tubes and emitters included within the respective enclosures) away from the central longitudinal axis of the catheter 300C and toward a wall of the body lumen. For instance, inflating the second enclosure 354 with conductive fluid to expand the second enclosure will cause the first enclosure 352, third enclosure 356, and fourth enclosure 358 (and the elongated tubes and emitters associated with each respective enclosure) to move away from the longitudinal axis of the catheter 300C and toward a wall of the body lumen. Accordingly, relatively greater expansion of one or more of the enclosures (and/or relatively lesser expansion of certain other enclosures) may cause at least one emitter included in the lesser-inflated enclosures to be positioned closer to the body lumen. After the enclosures have been inflated a desired amount to position one or more of the emitters closer to the lesion in the body lumen, shock waves can be generated at the emitters to selectively treat a region of the body lumen that is closest to the emitters.

FIGS. 6C and 7C illustrate the distal end of a third exemplary shock wave catheter 300 positioned in a body lumen. The exemplary catheter 300C includes a first enclosure 352 that is configured as a central enclosure, and at least one further enclosure that is configured as a peripheral enclosure. In some examples, the catheter 300C includes a single peripheral enclosure. However, as shown in FIG. 6C, the catheter 300C may include a plurality of peripheral enclosures disposed adjacent and peripheral to the central enclosure. In various embodiments, a catheter 300C could include four, five, six, seven, eight, or more than eight peripheral enclosures adjacent to and abutting a central enclosure of the catheter when the catheter is positioned in a body lumen and the enclosures are inflated. Each of the peripheral enclosures is sealed to an elongated tube and surrounds at least one emitter configured to generate shock waves in the respective enclosure of the plurality of peripheral enclosures. Each elongated tube extends into a respective enclosure of the plurality of peripheral enclosures and optionally includes a fluid lumen for independently inflating the respective enclosure of the plurality with conductive fluid. As seen in FIG. 6C, in some examples the central enclosure does not include an emitter.

When the distal end of the catheter 300C is advanced through a body lumen and positioned near a lesion in the body lumen, the central and peripheral enclosures can be inflated with conductive fluid to expand the enclosures and place the peripheral enclosures in contact with a portion of the body lumen. As seen in FIG. 6C, when the catheter 300C is positioned in a body lumen, the peripheral enclosures extend lateral to an abutting the central enclosure, such that inflation of the central enclosure applies a force against the peripheral enclosures to push the peripheral enclosures toward the wall of the body lumen. In the catheter 300C shown in FIG. 7C, expansion of the central enclosure while the catheter is disposed within the body lumen will move emitters disposed in all the peripheral enclosures closer to the lesion in a body lumen. Relatively greater inflation of any of the peripheral enclosures may move emitters disposed in the other lesser-inflated peripheral enclosures closer to the lesion in the body lumen.

FIG. 7C provides a cross-sectional view of the third exemplary shock wave catheter 300C shown in FIG. 6C. As seen in FIG. 7C, expansion of the central enclosure will exert an outward force on each of the peripheral enclosures to move the enclosures (and the elongated tubes and emitters included associated with each of the respective enclosures) away from the longitudinal axis of the catheter 300C and toward a wall of the body lumen. The relative inflation of the peripheral enclosures may also be used to modulate the distance between the various emitters and the wall of the body lumen. For instance, inflating the peripheral enclosures closest to one side of the body lumen may cause the peripheral enclosures closest to the opposite side of the body lumen (and the elongated tubes and emitters associated with the enclosures) to move closer to the opposite side of the body lumen. Accordingly, relatively greater expansion of one or more of the peripheral enclosures on one side of the body lumen (and/or relatively lesser expansion of peripheral enclosures on an opposite side of the body lumen) may cause at least one emitter included in the lesser-inflated enclosures to be positioned closer to the body lumen. After the enclosures have been inflated a desired amount to position one or more of the emitters closer to the lesion in the body lumen, shock waves can be generated at the emitters to selectively treat a region of the body lumen that is closest to the emitters.

As shown in FIGS. 6A-6C and 7A-7C, each emitter is enclosed within an enclosure, and optionally at least three pairs of emitters are located on an elongated tube within the enclosure. However, this is provided for explanatory purposes only, and a catheter may include a single emitter within one or more of the enclosures, two emitters within one or more of the enclosures, four emitters within one or more of the enclosures, six emitters within one or more of the enclosures, or greater than six emitters within one or more of the enclosures. In other examples, a catheter could include different numbers of emitters within different enclosures (e.g., with one pair of emitters in a first enclosure and two pairs of emitters in a second enclosure). In some examples, each peripheral enclosure may include one or more emitters, as illustrated in FIG. 7C. In other examples, emitters may be provided in only select peripheral enclosures, such as in alternating peripheral enclosures, or in peripheral enclosures along one circumferential side of the catheter such that sonic output from the emitters is concentrated on one side. In some examples, power is supplied to the emitters in each enclosure by way of one or more conductive wires (e.g., insulated copper wires) or optical fibers that are electrically or optically connected to at least one of the emitters inside each of the emitter-containing enclosures. The conductive wires or optical fibers may extend along at least a portion of an elongated tube. For instance, the conductive wires or optical fibers may extend through wire lumens included within the elongated tube(s).

In some examples, one or more the emitters are connected in series, such that power supplied by the power source generates shock waves at each of the emitters connected in series, e.g., as current flows across the spark gaps between respective electrodes of the emitters connected in series. For instance, emitters contained within a single enclosure of the catheter could be connected in series, such that all of the emitters in a particular enclosure can be fired together by applying a voltage pulse across the emitters. The emitters may be connected in series in a particular order that is favorable for shock wave treatments. For instance, in some examples a voltage pulse from the voltage source causes current to flow through emitters in a more distal region of the enclosure first to treat more distal portions of a lesion in a body lumen before flowing through emitters in a more proximal region of the enclosure to treat more proximal regions of the lesion in the body lumen.

In another example, one or more of the emitters may be wired on a separate circuit or a separate circuit branch, such that power can be selectively supplied to only a desired subset of emitters to generate shock waves at the desired subset. For instance, in one example the emitters contained in each of the respective enclosures may be wired in a separate circuit or circuit branch from the emitters contained in different enclosures, such that shock waves can be selectively generated within a particular enclosure of the catheter, e.g., to selectively treat regions of the body lumen closest to either the first, second, third, fourth or further enclosure. During a shock wave treatment, a user may first generate shock waves in a first enclosure to treat a region of the body lumen closest to the first enclosure, and then may continue by generating shock waves in a second, third, fourth, or further enclosure to treat additional regions of the body lumen. Additional or alternative wirings of the emitters are also anticipated.

In some examples, it may be favorable to position one or more of the emitters closer to a lesion in a body lumen by rotating the distal end of the catheter 300 in situ. As shown in, e.g., FIG. 7A, in some examples the emitters are arranged such that expansion of the various enclosures moves the emitters closer to only a portion of the walls of the body lumen (e.g., only a particular side of the lumen). In such examples, when in use, a physician may treat portions of the body lumen sequentially, such as by rotating the elongated tube to cause the enclosures to rotate within the body lumen to position at least one emitter closer to a new portion of the walls of the body lumen. For instance, the physician may incrementally rotate the elongated tube in a clockwise direction to treat the entire circumference of the body lumen.

Figure 8:
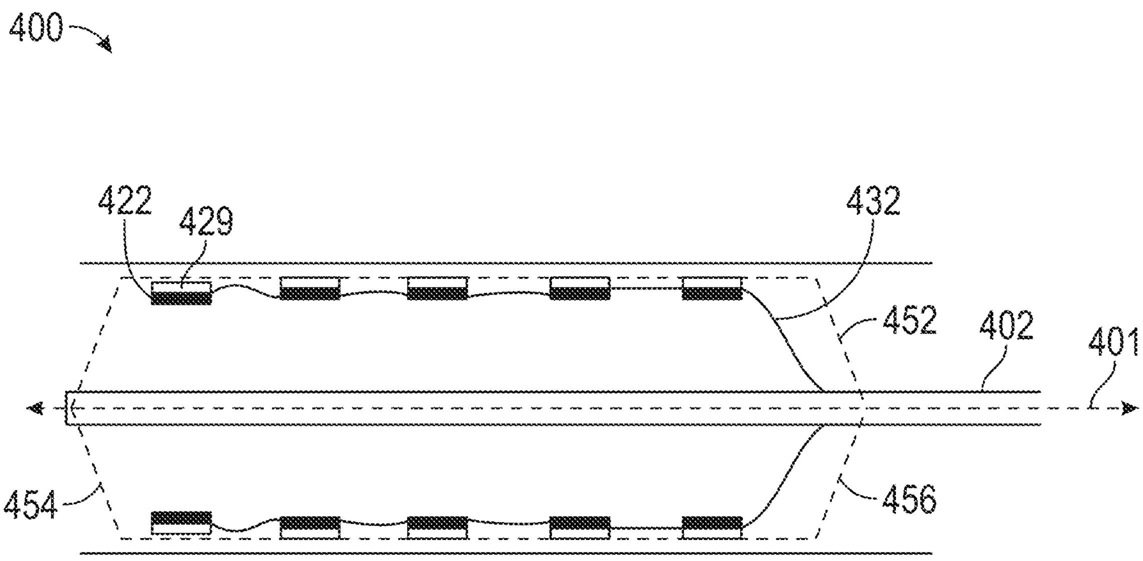
FIG. 8 illustrates the distal end of an exemplary shock wave catheter including at least one emitter disposed on an inner surface of the enclosure, according to one or more aspects of the present disclosure.

FIG. 8 illustrates an example of a shock wave catheter 400 that includes one of more emitters 422 disposed on an inner surface of an enclosure 452 near the catheter's distal tip, such that expansion of the enclosure while the catheter is disposed within the body lumen moves the at least one emitter farther from the central axis 401 and closer to a wall of the body lumen. The catheter 400 is an example of catheter 100 of FIG. 1. When the catheter 400 is advanced through a body lumen and positioned proximate to a lesion in a body lumen, the enclosure 452 can be inflated with conductive fluid to contact the body lumen, positioning the at least one emitter 422 proximate to a lesion in the body lumen. After the enclosure 452 has been inflated, one or more shock waves can be generated at the at least one emitter 422 to treat the lesion. When the shock wave treatment has been completed, the enclosure 452 can be deflated and the distal end of the catheter 400 removed from the body lumen.

The exemplary catheter 400 includes an elongated tube 402 defining a central longitudinal axis 401 of the catheter. An enclosure 452 having a distal end 454 and a proximal end 456 is sealed to a region of the elongated tube 402 surrounding the at least one emitter 422 and is fillable with conductive fluid to form an annular channel around the elongated tube where the at least one emitter can generate shock waves within the conductive fluid. When inflated, the enclosure 452 expands to fill the space within the body lumen and contact a wall of the body lumen that contains a lesion. The enclosure 452, as described above, could be an angioplasty balloon configured to inflate to a diameter. In some examples, the material of the enclosure is thicker than a conventional angioplasty balloon and/or configured to inflate a relatively lesser amount.

The enclosure 452 surrounds at least one emitter 422 that is disposed on the inner surface of the enclosure and is configured to generate shock waves inside the enclosure when a voltage is applied to the at least one emitter. Optionally, the at last one emitter 422 is adhesively attached to the inner surface of the enclosure 452 by way of an adhesive, such as a glue or some other adhesive material. Such a catheter 400 could include any number of emitters disposed on the inner surface of an inflatable enclosure. In one or more examples, the emitters 422 include more than two or less than two emitters, or more than six or less than six emitters. However, even greater numbers of emitters are also anticipated. For instance, as seen in FIG. 8, the at least one emitter 422 includes a plurality of emitters (e.g., ten emitters). As described above, each of the emitters may include at least one electrode pair, with the electrodes of each pair spaced apart from one another to form a spark gap between the electrodes. However, in alternative examples each of the emitters may be formed by a distal tip of an optical fiber.

As shown in FIG. 8, the emitters 422 are disposed on an inner surface of the enclosure 452. In some examples, the emitters 422 are arranged approximately evenly across the surface of the enclosure, for instance, the emitters could be disposed on the inner surface of the enclosure 452 in a spiral pattern or a grid pattern. However, the emitters 422 may be arranged in any desired pattern on the inner surface of the enclosure 452. In other examples, the emitters 422 may be arranged with a greater or lesser number of emitters on a particular side of the enclosure 452, i.e., to selectively target a certain area of a body lumen. In another example, a greater number of emitters are positioned toward the distal end of the enclosure 452 to facilitate treatment of lesions and other lesions that may prevent advancement of the full width of the enclosure through the body lumen and are more effectively treated by shock waves through a distal end of the enclosure. Additional arrangements of the emitters are also anticipated.

When generating shock waves from the emitters 422, shock waves can propagate generally outwardly (i.e., outwardly with respect to a central longitudinal axis of the catheter 400). In one or more examples, the at least one emitter 422 is oriented to generate shock waves outwardly from a longitudinal axis of the catheter 400 in a direction toward the inner surface of the enclosure 452 and the lesion in the body lumen. In another example, and to minimize the risk of rupturing the enclosure 452 during the generation of shock waves, the emitters 422 could be arranged to propagate shock waves in a direction that is approximately perpendicular to an inner wall of the enclosure 452 (e.g., with one or more forward-firing emitters), or toward the longitudinal axis of the catheter 400. Alternatively, or in addition, the emitters 422 may be oriented to generate shock waves in a variety of directions outwardly from the elongated tube 402, e.g., with one or more forward-firing emitters, one or more outwardly firing emitters and/or one or more emitters firing perpendicular to the inner wall of the enclosure 452. In some examples, a relatively lower power is applied to emitters 422 on the surface of the enclosure 452 in order to produce relatively lower magnitude shock waves that are less likely to rupture the material of the enclosure.

In some examples, a shock wave generating region of one or more of the emitters 422 (e.g., a spark gap between a pair of electrodes of an emitter) is maintained a distance away from the surface of the enclosure 452. As mentioned above, positioning the emitter(s) 422 close to the enclosure 452 wall may risk rupturing the enclosure when shock waves are fired from the emitters 422 in close proximity to the material of the enclosure. Accordingly, in some examples, a spark gap of at least one of the emitters is at least one-tenth millimeter (0.1 mm) away from the inner surface of the enclosure, at least fifteen-hundredths of a millimeter (0.15 mm) away from the inner surface of the enclosure, at least one-fifth millimeter (0.2 mm) away from the inner surface of the enclosure, at least one-quarter millimeter (0.25 mm) away from the inner surface of the enclosure, or at least one-half millimeter (0.5 mm) away from the inner surface of the enclosure.

To further mitigate the risk of rupturing the enclosure 452 wall, in some examples one or more of the emitters 422 are spaced from the inner wall of the balloon by way of one or more spacers 429. Beneficially, the spacers 429 may maintain a spark gap of the emitters 422 away from the enclosure wall by a distance that prevents the shock waves from rupturing the enclosure 452 at voltages typically applied across the emitters. In various examples, the spacers 429 may be configured to maintain the spark gap of the emitters at least one-tenth millimeter (0.1 mm) away from the inner surface of the enclosure, at least fifteen hundredths of a millimeter (0.15 mm) away from the inner surface of the enclosure, at least one-fifth millimeter (0.2 mm) away from the inner surface of the enclosure, at least one-quarter millimeter (0.25 mm) away from the inner surface of the enclosure, or at least one-half millimeter (0.5 mm) away from the inner surface of the enclosure. For example, a spacer 429 may have a height of at least one-tenth millimeter (0.1 mm), at least one-fifth millimeter (0.2 mm), at least one-quarter millimeter (0.25 mm), or at least one-half millimeter (0.5 mm). In some examples, the spacers may be cylindrically shaped. The spacers 429 may be disposed between the emitters 422 and the enclosure 452 wall and are optionally attached to the emitters and/or balloon by way of an adhesive. The spacers 429 may be configured to orient the emitters 422 in a desired direction relative to the central longitudinal axis 401 of the catheter 400 and/or the enclosure wall (e.g., to position the emitters such that they fire toward the inner surface of the balloon and toward a lesion in a body lumen).

The emitter(s) 422 of catheter 400 can be connected to a power source (e.g., a pulsed voltage source) such as the power source 28 to supply power to the emitter(s) 422 within the enclosure 452 to generate shock waves. In some examples, power is supplied to the emitters 422 by way of one or more conductive wires (e.g., insulated copper wires) that extend between the power source and the at least one emitter disposed on the inner surface of the enclosure. For instance, in some examples a first wire 432 and a second wire 434 extend along at least a portion of the elongated tube 402 to provide an electrical connection to the various emitters 422 mounted on the inner surface of the enclosure 452. In some examples, one or more of the wires 432, 434 extend through a wire lumen inside the elongated tube 402, or in channels or ridges that extend along the exterior of the elongated tube. In some examples, the wires 432, 434 may extend past the distal tip of the elongated tube and into the enclosure and are in electrical connection with at least one of the emitters. In some examples, the wires 432, 434 extend along at least a portion of the inner surface of the enclosure 452 (e.g., extend along the inner surface between each of the electrodes disposed on the inner surface). In some examples, the wires 432, 434 are fixed or adhered to the surface of the enclosure 452 at one or more points. The conductive wires 432, 434 may optionally include some slack in the portion of the wires inside the enclosure 452 so that the wires can bend and conform during inflation of the enclosure without providing physical resistance that impedes the inflation of the enclosure. When the enclosure 452 is in a deflated state, e.g., during insertion and advancement of the catheter 400, the wires 432, 434 may be folded within the enclosure 452. However, in other examples, and as seen in FIG. 8, the conductive wires 432, 434 extend freely within the enclosure 452 between one or more of the emitters 422 and are not adhered or fixed to the inner surface of the enclosure. In other examples, laser energy is used to generate the shock waves, and power may be supplied to the emitters 422 through optical fibers similarly configured as the wires 432, 434.

In some examples, the emitters 422 are connected in series, such that power supplied by the power source (e.g., a voltage pulse) generates shock waves at each of the emitters in the enclosure 452 as current flows across each spark gap between electrodes of the emitters. The emitters 422 may be connected in an order that is more favorable for shock wave treatments (e.g., with current flowing through the more distal emitters first and generating shock waves in more distal portions of the enclosure in order to treat more distal portions of a lesion in a body lumen.)

In another example, one or more of the emitters 422 may be wired on a separate circuit or circuit branch, such that voltage pulses can be selectively applied to only a desired subset of emitters. For instance, a distal grouping of emitters, a central grouping of emitter, and/or a proximal grouping of emitters could be wired in separate circuits or branches (with emitters within each grouping wired in series and configured to fire together), such that shock waves can be selectively generated at either the respective distal, central, and proximal grouping of emitters. In another example, emitters that are adhered to a various portions or sides of the enclosure could be wired in separate circuits or branches, such that shock waves can be selectively generated on a certain side of the enclosure, e.g., in order to treat a nonconcentric lesion located on a particular side of the body lumen. Additional or alternative wirings of the emitters are also anticipated.

The one or more enclosures of any of the above catheters, when inflated, may individually or collectively have an expanded diameter than is approximately equal to the diameter of a body lumen (i.e., the diameter of the body lumen, or a smaller diameter representing the diameter when partially occluded with a lesion). In various embodiments, the enclosure(s), in an expanded state, could have an inflated diameter of at least four millimeters (4 mm), at least five millimeters (5 mm), at least eight millimeters (8 mm), at least ten millimeters (10 mm), or greater than twenty millimeters (20 mm). In more particular examples, the enclosure(s) has an inflated diameter between nine millimeters (9 mm) and twelve millimeters (12 mm), or between twenty millimeters (20 mm) and twenty-five millimeters (25 mm). However, an exemplary catheter can include one or more enclosures configured to expand to any inflated diameter. In some examples, a catheter includes two or more enclosures, each enclosure having an inflated diameter, e.g., with a central enclosure having a greater diameter than one or more peripheral enclosures, or a first enclosure having a diameter greater than a second enclosure.

The enclosure(s) may be formed from a material having elastomeric properties such that the enclosure can be repeatedly inflated and deflated without damaging or deforming the material of the balloon. For instance, the enclosure(s) can be formed from a polymeric material. In some examples, the enclosure(s) include one or more inflatable angioplasty balloon. However, in other examples the enclosure(s) are formed from a relatively more rigid material or have a relatively greater wall thickness such that the enclosure inflates a relatively lesser amount than a conventional angioplasty balloon. In another aspect, the enclosure(s) could be formed from a material that is thicker than the material of a conventional angioplasty balloon. In some examples, the enclosure(s) is configured such that when it is inflated, it contacts the body lumen and/or an occluded region of the body lumen. However, in other examples, e.g., multi-balloon examples, the enclosure(s) may be inflated to a relatively smaller diameter (i.e., inflated to less than a fully inflated state), such that the combined inflation of multiple enclosures causes more than one enclosure to contact the surface of the body lumen and/or the lesion. In other examples of multi-enclosure catheters, one or more of the enclosures may be made of a different material and/or have a different wall thickness than the other enclosure(s) to enable the enclosures to expand to different sizes.

In some examples, the enclosure(s) are configured to accept inflation pressures of up to approximately four atmospheres (4 atm) (i.e., is formed of a compliant material that permits the enclosure to inflate to four atmospheres (4 atm) without rupturing or deforming the material of the balloon). In one or more examples, the enclosure(s) may be compliant enough to accept inflation pressures of more than four atmospheres (4 atm), such as inflation pressures up to six atmosphere (6 atm) or up to ten atmospheres (10 atm).

The enclosure(s) may be configured to assume a circular shape (as viewed from a cross sectional perspective) while inflated. However, in other examples, the enclosure(s) may be configured to assume an elliptical shape, or any other suitable shape. In examples including multiple enclosures (see, e.g., FIGS. 6A-6C and 7A-7C), the shape of a first enclosure may be compressed by the inflation of a second or further enclosure proximate to and/or abutting the first enclosure. Similarly, the position of a first enclosure within a body lumen may be moved (e.g., forced in an outward direction from the central longitudinal axis of the catheter) by inflating a second or further enclosure proximate to and/or abutting the first enclosure.

The enclosure(s) surround an emitter assembly including at least one emitter configured to generate shock waves inside the enclosure to treat a lesion in a body lumen. As described in further detail with reference to FIGS. 2A-2B, 3A-3B, 4A-4B, 5A-5C, 6A-6C, 7A-7C, and 8, at least one emitter is configured to move outward relative to the longitudinal axis of the elongated tube 12 to a position closer to the inner surface of the balloon and/or a lesion in the body lumen. In some examples, the emitter(s) are configured to expand outwardly at least one millimeter (1 mm), at least two millimeters (2 mm), at least three millimeter (3 mm), at least four millimeters (4 mm), or at least five millimeters (5 mm) from the central longitudinal axis of the catheter 100 (i.e., a central longitudinal axis of an elongated tube 12 of the catheter). However, in other examples, the emitter(s) are configured to expand even farther, for instance, at least one centimeter (1 cm) from the catheter's central longitudinal axis.

Figure 9:
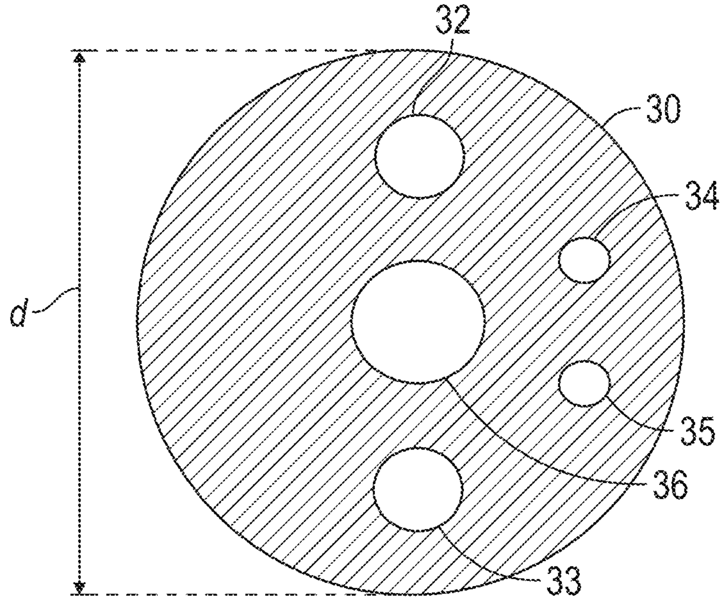
FIG. 9 illustrates a cross-sectional view of an elongated tube of an exemplary catheter, according to one or more aspects of the present disclosure.

A cross-section of an exemplary elongated tube 30 is illustrated in FIG. 9. The elongated tube 30 includes at least one fluid lumen 32 for introducing conductive fluid into an enclosure at the distal end of the catheter. In some examples, and as shown in FIG. 9, an elongated tube 30 may include at least a second fluid lumen 33 for introducing conductive fluid into a second or further enclosure at the distal end of the catheter. The elongated tube 30 also includes one or more wire lumens, channels, or external grooves for carrying conductive wires or optical fibers that supply power from an external power source, e.g., a voltage pulse from the intravascular lithotripsy (IVL) generator 28 shown in FIG. 1, to one or more emitters within the enclosure at the distal end of the catheter. For instance, the elongated tube 30 includes a first wire lumen 34 for carrying a first wire and a second wire lumen 35 for carrying a second wire (or, in alternative embodiments, a first optical fiber and a second optical fiber). Additionally, or alternatively, the elongated tube 30 may include one or more channels or exterior grooves on an external edge of the elongated tube, and one or more wires (or optical fibers) extend within the channels between the external power source and the emitters. In some aspects, an elongate member extends through a central lumen 36 of the elongated tube 30, which optionally extends along the longitudinal axis of the elongated tube 30, and the elongate member is used to actuate an expandable support structure to position one or more emitters closer to a lesion (e.g., by moving the elongate member in a proximal or distal direction relative to the elongated tube). The elongated tube 30 also optionally includes a guidewire lumen for receiving a guidewire to facilitate insertion and advancement of the catheter through a body lumen. The elongated tube has a diameter d which may be, for example, less than one millimeter (1 mm), between one millimeter (1 mm) and two millimeters (2 mm), between two millimeters (2 mm) and three millimeters (3 mm), between three millimeters (3 mm) and four millimeters (4 mm), or greater than four millimeters (4 mm).

The elongated tube 30 of FIG. 9 may be used as the elongated tube of any of the catheters shown in FIGS. 2A-2B, 3A-3B, 4A-4B, 5A-5C, 6A-6C, 7A-7C, and 8. The particular channels, lumens, and other aspects of the elongated tube may vary when applied to the particular exemplary catheters described herein. For instance, an elongated tube used in the catheters of FIGS. 2A-2B, 3A-3B, 4A-4B, 5A-5C, 6A-6C, 7A-7C, and 8 may include greater or fewer channels and lumens than the elongated tube. For instance, some exemplary catheters may lack a guidewire lumen, or may lack wire lumens or fluid lumens. Any of the channels and lumens of the elongated tube may alternatively be disposed external to the elongated tube (e.g., in a side tube or a channel in the exterior surface of the elongated tube). Further, certain channels or lumens may be combined to serve two purposes, e.g., a lumen configured to receive both a guide wire and an elongate member, or a lumen configured to carry a wire and flow conductive fluid into the enclosure.

In multi-balloon embodiments of the catheter (e.g., the exemplary catheters shown in FIGS. 6A-6C and 7A-7C), the elongated tube may include a number of fluid lumens equal to the number of enclosures of the catheter, with each of the fluid lumens entering into and configured for inflating a respective enclosure of the catheter. Additionally, or alternatively, some exemplary catheters may include two or more elongated tubes (e.g., a first elongated tube and a second elongated tube, or an elongated tube and a side tube), each tube extending into a different enclosure of the catheters. In such examples, the features of the elongated tube may be divided or replicated among the various elongated tubes and/or side tubes to provide parallel fluid lumens, wire lumens, and other features to the various enclosures. In yet further examples, an elongated tube of the catheter may fork near the distal end of the catheter and extend into two or more enclosures at the catheter's distal end. In such examples, the distal end of the elongated tube may be configured as two or more elongated tubes. Accordingly, the elongated tube of FIG. 9 is provided merely as an example, and other elongated tubes described herein may incorporate more, fewer, or different features than the elongated tube.

In some embodiments, a shock wave catheter includes a shock wave emitter assembly having, on an adjustable support structure, more than one emitter located such that a longitudinal spacing (i.e., spacing along a longitudinal axis of the catheter) or circumferential spacing (i.e., spacing about a central longitudinal axis of the catheter) is tunable by adjusting the support structure (e.g., by collapsing or expanding the support structure) to optimize the interference pattern of the shock waves generated by the more than one emitter. For example, the longitudinal spacing of two adjacent emitters may be adjusted to be less than about four millimeters (4 mm) to allow shock waves generated from the two emitters to substantially constructively interfere and exert more force on an occlusion than would be possible from non-interfering waves from the same emitters. This same catheter may also be used to treat another occlusion requiring less force by tuning the longitudinal spacing to reduce the amount of constructive interference. Intravascular lithotripsy with interfering shock waves is described in detail in U.S. patent application Ser. No. 17/967,544, the entire contents of which is incorporated herein by reference.

Figure 10:
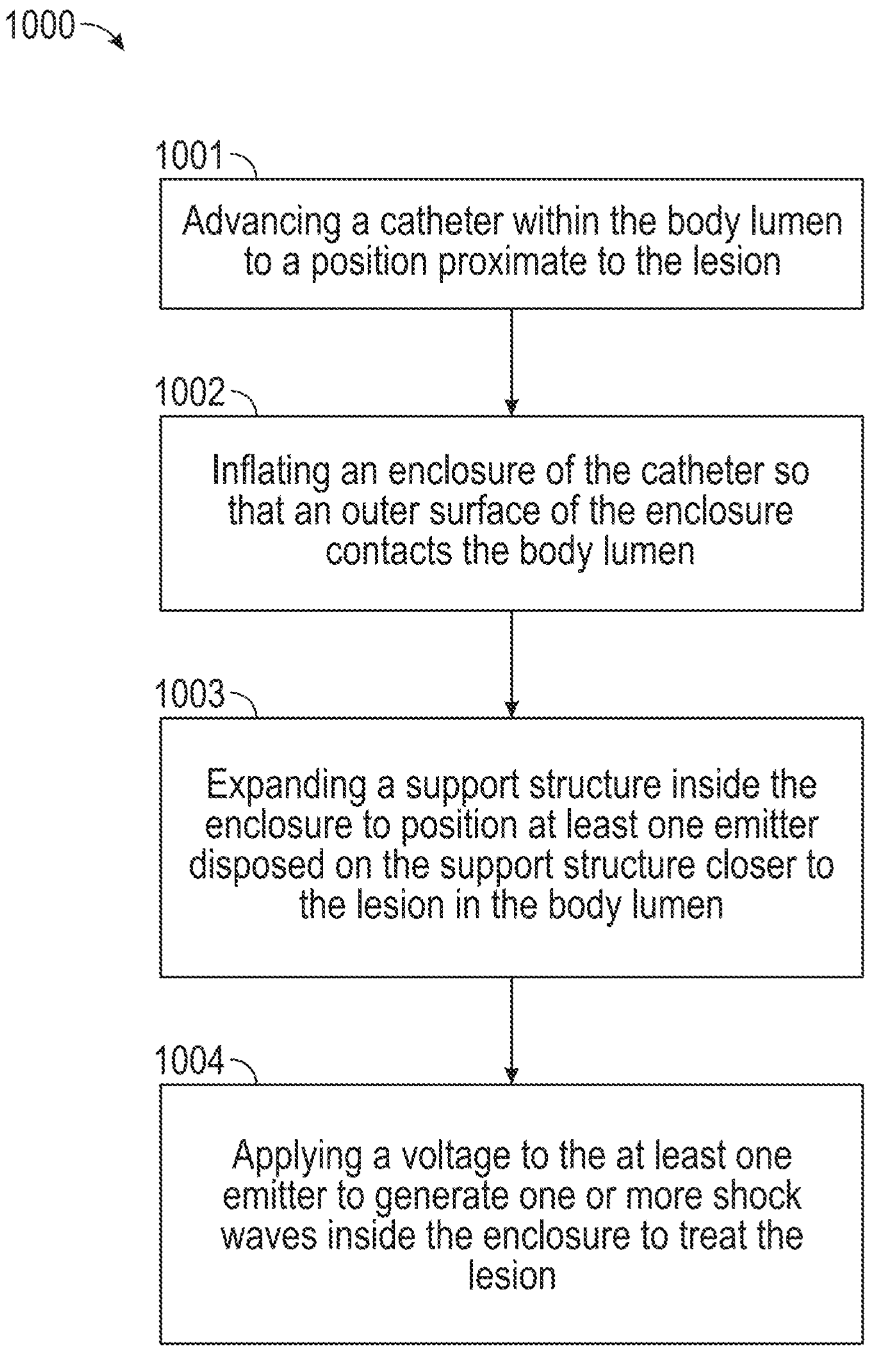
FIG. 10 illustrates a flow chart of an exemplary method of treating a lesion in a body lumen with a shock wave catheter having an expandable support structure, according to one or more aspects of the present disclosure.

FIG. 10 illustrates one exemplary method 1000 of treating a lesion in a body lumen. The method can be used with a catheter including an expandable support structure, such as either of the catheters shown in FIGS. 2A-2B, FIGS. 3A-3B, and FIGS. 4A-4C, described above.

At step 1001, the method 1000 includes advancing a catheter within the body lumen to a position proximate to the lesion. In some examples, wherein the enclosure is in a folded state when the catheter is advanced through the body lumen. In some examples, the diameter of the support structure is less than one millimeter (1 mm), less than two millimeters (2 mm), less than three millimeters (3 mm), less than four millimeters (4 mm), or less than five millimeters (5 mm) when the catheter is advanced through the body lumen. In some examples, the diameter of the support structure is between one millimeter (1 mm) and two millimeters (2 mm), between two millimeters (2 mm) and four millimeters (4 mm), or between four millimeters (4 mm) and six millimeters (6 mm) when the catheter is advanced through the body lumen. At step 1002, the method 1000 includes inflating an enclosure of the catheter so that an outer surface of the enclosure contacts the body lumen.

At step 1003, the method 1000 includes expanding a support structure inside the enclosure to position at least one emitter disposed on the support structure farther from the central longitudinal axis of the catheter and/or closer to the body lumen. In some examples, expanding the support structure comprises expanding the support structure to a diameter between eight millimeters (8 mm) and twelve millimeters (12 mm). In some examples, expanding the support structure comprises expanding the support structure to a diameter greater than one centimeter (1 cm). In some examples, expanding the support structure moves a first emitter outward from a longitudinal axis of the catheter in a first direction and moves a second emitter outward from the longitudinal axis in a second direction. In some examples, the first direction is opposite the second direction. In some examples, the support structure comprises a first stop and a second stop that are spaced apart in a collapsed state of the support structure and abutting in an expanded state of the support structure, and wherein expanding the support structure comprises moving the second stop toward the first stop. In some examples, expanding the support structure comprises moving an elongate member in a proximal direction or a distal direction, wherein the elongate member extends between and is operably coupled to at least one of the first stop and the second stop. In some examples expanding the support structure comprises pulling a wire operably coupled to at least one of the first stop and the second stop. In some examples, the elongate member comprises a first tube and a second tube surrounding at least a portion of the first tube, and wherein movement of the second tube relative to the first tube causes expansion of the support structure.

At step 1004, the method 1000 includes supplying power to the at least one emitter (e.g., by applying a voltage across an electrode pair of the at least one emitter) to generate one or more shock waves inside the enclosure to treat the lesion. In some examples, the method further includes rotating the support structure to position the at least one emitter closer to the lesion in the body lumen.

Figure 11:
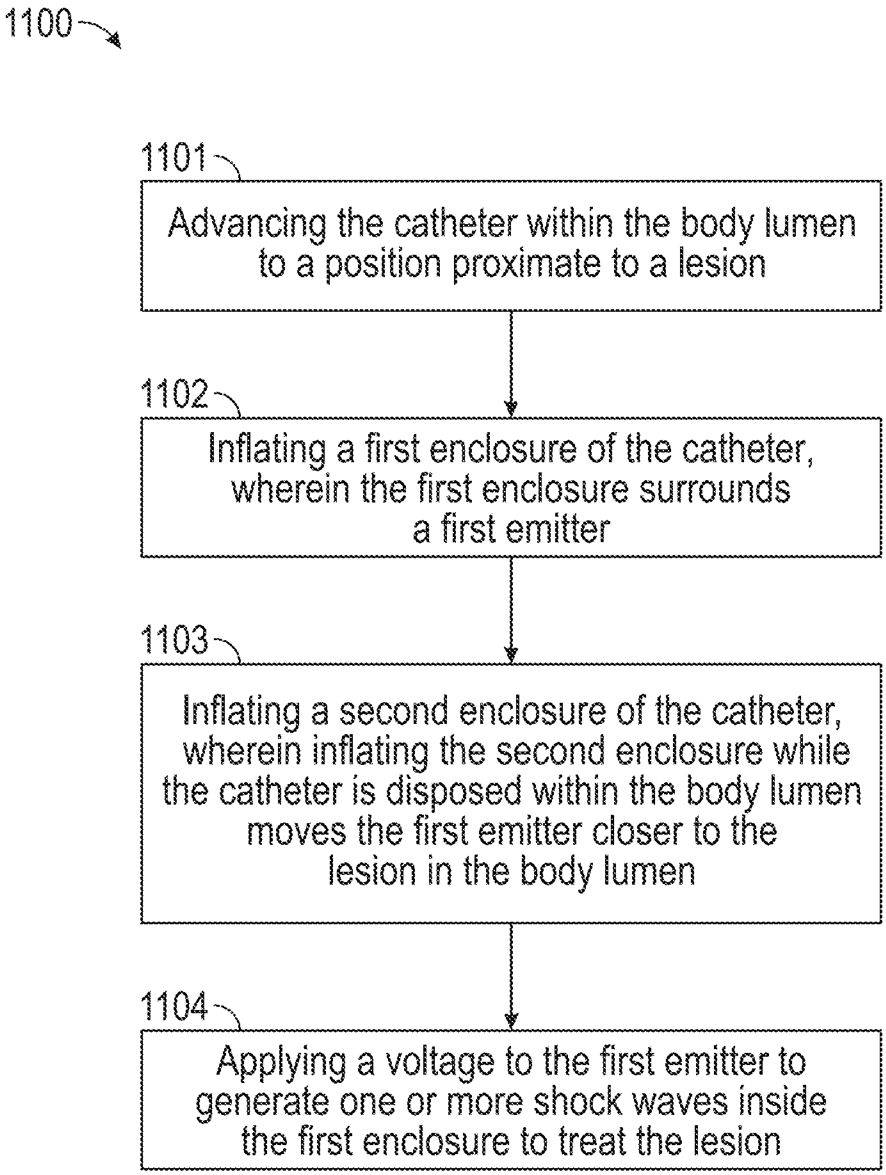
FIG. 11 illustrates a flow chart of an exemplary method of treating a lesion in a body lumen with a shock wave catheter having two or more enclosures, according to one or more aspects of the present disclosure.

FIG. 11 illustrates another exemplary method 1100 of treating an occlusion in a body lumen. The method can be applied to a catheter including multiple enclosures, such as any of the multi-balloon catheters shown in FIGS. 6A-6C and FIGS. 7A-7C, described above. At step 1101, the method 1100 includes advancing the catheter within the body lumen to a position proximate to the lesion. In some examples, the first enclosure and the second enclosure are in a folded state when the catheter is advanced through the body lumen. At step 1102, the method 1100 includes inflating a first enclosure of the catheter, wherein the first enclosure surrounds a first emitter.

At step 1103, the method 1100 includes inflating a second enclosure of the catheter, wherein inflating the second enclosure while the catheter is disposed within the body lumen moves the first emitter closer to the lesion in the body lumen. In some examples, inflating the first enclosure and the second enclosure comprises filling the enclosures with a conductive fluid. In some examples, inflating the first enclosure comprises filling the first enclosure with conductive fluid via a first fluid lumen, and wherein inflating second enclosure comprises filling the second enclosure with conductive fluid via a second fluid lumen.

At step 1104, the method 1100 includes applying a voltage to the first emitter to generate one or more shock waves inside the first enclosure to treat the lesion. In some examples, the second enclosure surrounds a second emitter, and the method further comprises applying a voltage to the second emitter to generate one or more shock waves inside the second enclosure. In some examples, the method includes inflating a third enclosure of the catheter, wherein inflating the third enclosure while the catheter is disposed within the body lumen moves the first emitter closer to the lesion in the body lumen. In some examples, the third enclosure surrounds a third emitter, and wherein the method further comprises applying a voltage to the third emitter to generate one or more shock waves inside the third enclosure.

In some examples, the method further includes rotating the first enclosure and the second enclosure around a longitudinal axis of the catheter to move the first emitter closer to the lesion in the body lumen.

Figure 12:
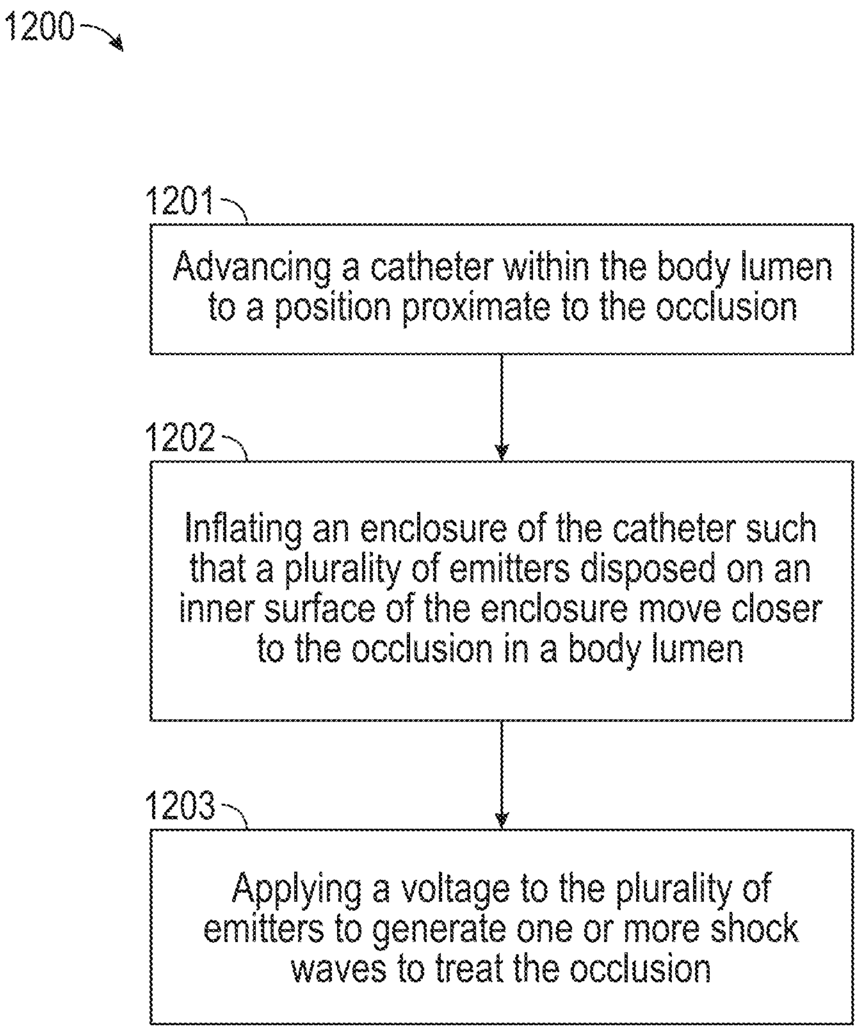
FIG. 12 illustrates a flow chart of an exemplary method of treating a lesion in a body lumen with a shock wave catheter having at least one emitter disposed on an inner surface of an enclosure, according to one or more aspects of the present disclosure.

FIG. 12 illustrates yet another exemplary method 1200 of using a shock wave catheter. The method 1200 can be applied to a catheter having emitters disposed on an inner surface of an enclosure of the catheter, such as the catheter shown in FIG. 8, described above. At step 1201, the method 1200 includes advancing a catheter within the body lumen to a position proximate to the lesion. At step 1202, the method 1200 includes inflating an enclosure of the catheter such that a plurality of emitters disposed on an inner surface of the enclosure move closer to the lesion in the body lumen. At step 1203, the method 1200 includes supplying power (e.g., applying a voltage) to the plurality of emitters to generate one or more shock waves to treat the lesion.

Figure 13:
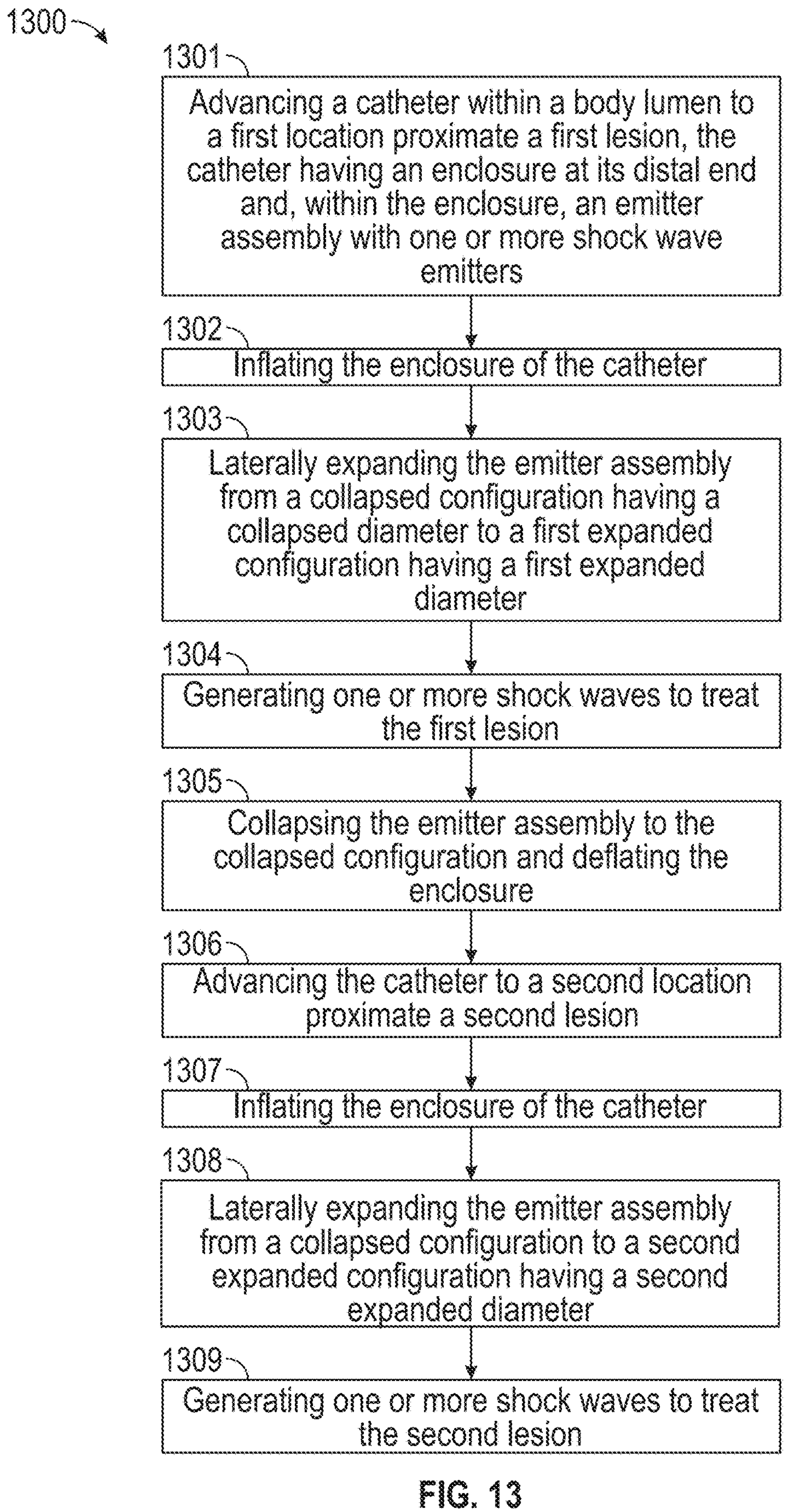
FIG. 13 illustrates a flow chart of an exemplary method of using a shock wave catheter.

FIG. 13 illustrates another exemplary method 1300 of using a shock wave catheter. In this method, a single catheter having an emitter assembly with one or more emitters (for example, any of the catheters described above) is used to treat multiple lesions in a patient's body. Step 1301 includes advancing a catheter within the body lumen to a first location proximate to a first lesion. The catheter has an enclosure at a distal end and, within the enclosure, an expandable emitter assembly having, in a collapsed configuration, a collapsed diameter. The one or more emitters of the emitter assembly may be located on a laterally expandable support structure, within a plurality of enclosures, or affixed to an inner wall of the enclosure as described above. Step 1302 includes inflating the enclosure at the distal end of the catheter. Step 1303 includes laterally expanding the support structure such that the support structure has an expanded first diameter. Step 1304 includes generating one or more shock waves to treat the first lesion. Step 1305 includes collapsing the emitter assembly and deflating the enclosure. Step 1306 includes advancing the catheter within the body lumen to a second location proximate to a second lesion. Step 1307 comprises inflating the enclosure at the distal end of the catheter. Step 1308 comprises laterally expanding the support structure such that the emitter assembly has a second expanded diameter different from the first diameter. Step 1309 comprises generating one or more shock waves to treat the second lesion.

In an alternative implementation of the method 1300, one of the steps 1303 and 1308 is an optional step such that the support structure is not expanded before generating shock waves at steps 1304 and 1309. This method may be implemented to accommodate a relatively smaller sized vessel at the first or the second location.

Figure 14A:
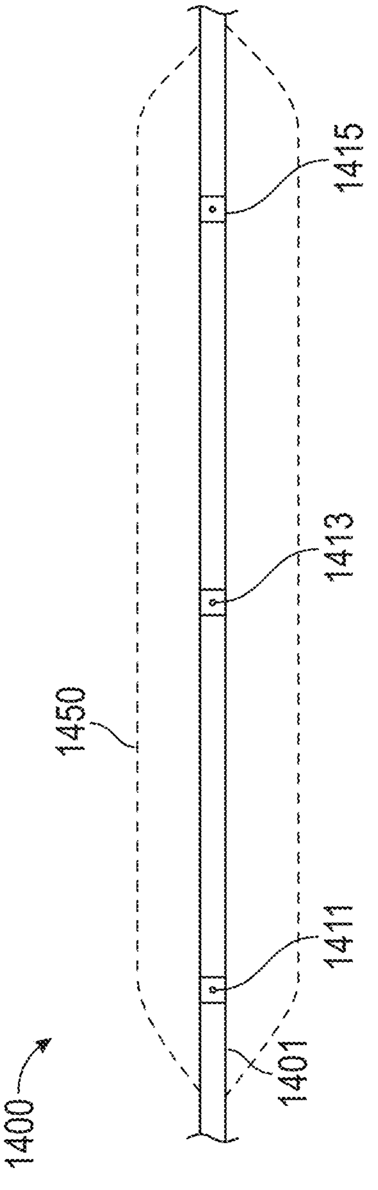
FIGS. 14A-14B illustrate an exemplary shock wave catheter having a flexible ribbon at its distal end.
Figure 14B:
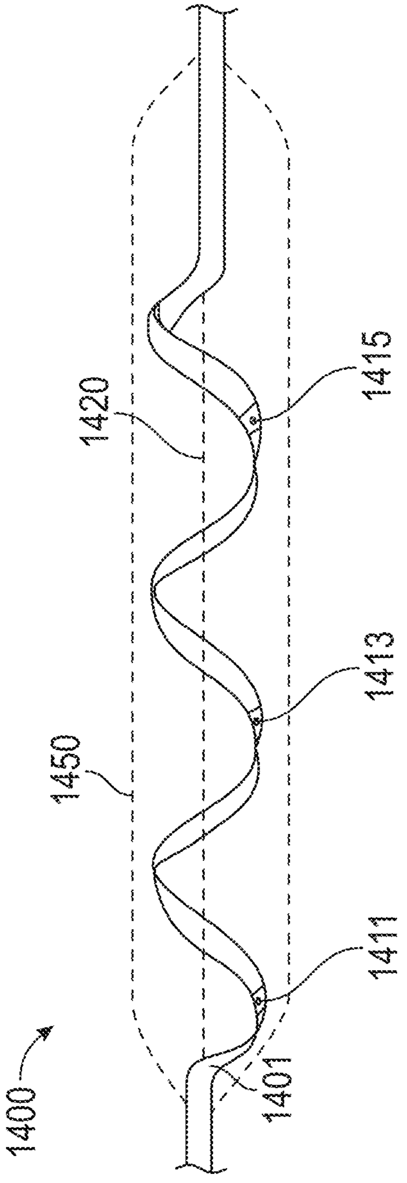

FIGS. 14A and 14B illustrate another exemplary shock wave catheter 1400 having at its distal region a flexible ribbon 1401 surrounded by an enclosure 1450 that is fillable with a fluid. In one or more embodiments, the enclosure 1450 is an angioplasty balloon. In various embodiments, at least one shock wave emitting region (e.g., regions 1411, 1413, 1415) is mounted on the ribbon and configured (e.g., by electrical wires or optical fibers) to generate shock waves when supplied with power (e.g., by a voltage application or a laser). In other words, the ribbon may be a support structure for the at least one shock wave emitting region. In one or more embodiments, the at least one shock wave emitting region includes an electrode pair as described above. In some embodiments, the at least one shock wave emitting region includes one or more light emitting regions (e.g., uncladded regions) of an optical fiber or an optical fiber bundle. The ribbon 1401 may be connected at its proximal to an elongate tube similar to the elongate tubes described above.

FIG. 14A illustrates a first configuration of the catheter 1400, wherein the ribbon 1401 is substantially straight (e.g., substantially uncoiled), which allows for a lower profile when the catheter is being navigated to a target lesion. FIG. 14B illustrates a second embodiment of the catheter 1400, wherein the ribbon 1401 is helically coiled and substantially about a central longitudinal axis 1420 of the enclosure 1450. In this second configuration, one or more of the shock wave emitting regions 1411, 1413, 1415 are laterally farther from the central longitudinal axis 1420 than in the uncoiled configuration. In one or more embodiments, the enclosure is filled to a pressure of about two atmospheres (2 atm) to about six atmospheres (6 atm) in the second configuration. In one or more embodiments, the enclosure is filled to a pressure of about one atmospheres (1 atm) to about four atmospheres (4 atm) in the second configuration. In one or more embodiments, the enclosure is filled to a pressure of about one atmospheres (1 atm) to about six atmospheres (6 atm) in the second configuration In one or more embodiments, at least one of the shock wave emitting regions is no less than one millimeter (1 mm) away from the central longitudinal axis in the second configuration. In one or more embodiments, at least one of the shock wave emitting regions is about three millimeters (3 mm) to about six millimeters (6 mm) away from the central longitudinal axis (e.g., the longitudinal axis of a balloon of the catheter) in the second configuration. In one or more embodiments, at least one of the shock wave emitting regions is closer to a wall of the enclosure than the central longitudinal axis in the second configuration. In one embodiment, the at least one shock wave generating region is no less than one millimeter (1 mm) away from the enclosure wall in the second configuration. In some embodiments, the at least one emitter is less than one millimeter (1 mm) away from the wall of the enclosure in the second configuration.

According to one embodiment, the position(s) of the one or more shock wave generating regions is adjusted by rotating the ribbon about the central longitudinal axis. This may be accomplished by rotating the ribbon or a elongated tube attached to the tube at a more proximate location of the catheter. For instance, the support structure may be connected to a rotatable proximal handle. Rotation of the proximal handle may change the ribbon from the first configuration to the second configuration.

In some embodiments, the ribbon 1401 may be formed of a shape-memory material (e.g., nitinol) or an elastic material (e.g., an elastic polymer) that, when enclosure 1450 is not filled with fluid, is substantially unwound such that the at least one shock wave generating regions are proximate a central axis of the enclosure 1450. When enclosure 1450 is filled with fluid, the ribbon 1401 may be configured to become more coiled such that the at least one shock wave generating regions moves laterally away from the central axis of enclosure 1450. In embodiments where the ribbon 1401 is made of a shape-memory material, the ribbon may automatically become coiled in response to an environmental stimulus (e.g., a change in temperature, pH, pressure) when the distal region is positioned at a treatment site and the enclosure is filled with fluid. In some embodiments, the ribbon 1401 may elastically become coiled to move the at least one shock wave generating regions laterally outward in response to the enclosure 1450 expanding (when filled with fluid).

Figure 15B:
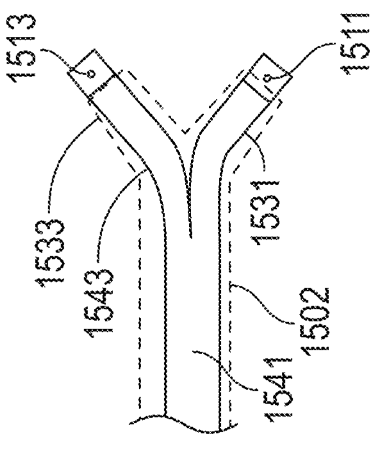
FIGS. 15A-15D illustrate the distal region of another exemplary shock wave catheter having one or more movable shock wave emitting regions, such as angled ports for housing emitters.
Figure 15D:
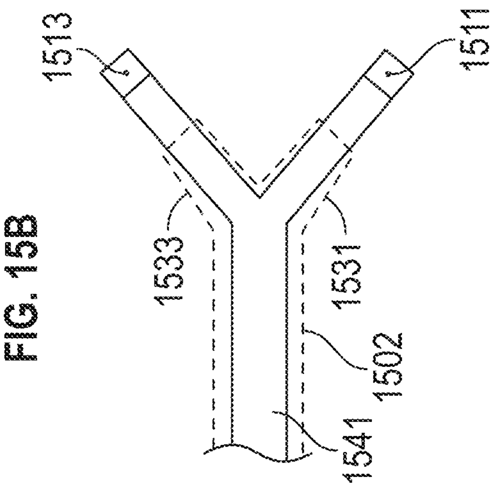
Figure 15A:
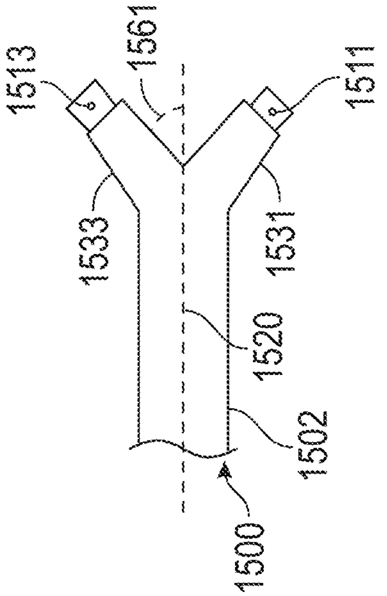

FIGS. 15A-15D illustrate the distal region of another exemplary shock wave catheter 1500 having one or more movable shock wave emitting regions 1511, 1513. Catheter 1500 includes one or more angled ports (e.g., ports 1531, 1533) that branch off from outer tube 1502. Each port is associated with a shock wave generating region (e.g., shock wave generating regions 1511, 1513). As shown in FIGS. 15A and 15B, the shock wave generating regions may be at least partially housed within the angled ports, which allows for a narrower profile when the catheter is being navigated to a target lesion. In one or more embodiments, the at least one shock wave generating region is connected to a hinge region 1543, which may be formed of an elastic material, which improves navigability and can further reduce the catheter's profile. Each of the shock wave generating regions 1511, 1513 branch from an inner elongate member 1541.

Figure 15C:
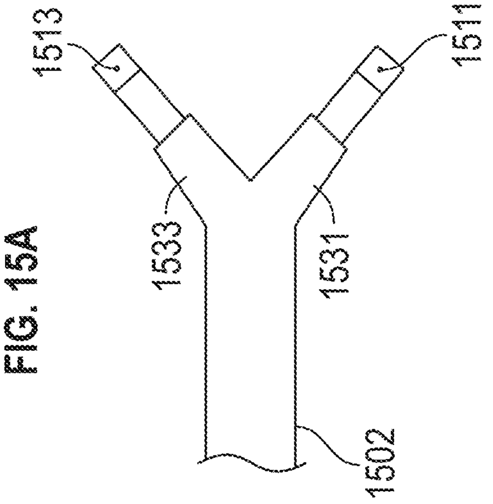

As shown in FIGS. 15C and 15D, at the site of treatment, an enclosure (e.g., an angioplasty balloon) may be inflated and the shock wave generating regions 1511, 1513 (e.g., shock wave generating emitters) (housed within the enclosure) are moved outwards from the angled ports such that the shock wave generating regions 1511, 1513 are farther away from a central axis 1520 of the catheter 1500. For instance, a first shock wave generating emitter may be located along and configured to extend along a first emitter axis through a first emitter port, and a second shock wave generating emitter may be located along and configured to extend along a second emitter axis through a second emitter port. In some embodiments, the first and/or second emitter axis are not parallel to the central longitudinal axis. a first configuration the shock wave generating regions may be located within an emitter port, and in a second configuration (e.g., an extended configuration), the shock wave generating regions may be located at least half a millimeter (0.5 mm) outside of the emitter ports. The angled ports 1531 and 1533 guide the movement of the shock wave generating regions outwards along an emitter axis that is non-parallel to the central longitudinal axis. This outward movement of the shock wave generating region may be approximately equal to a port angle 1561, which may be no less than ten degrees. In one or more embodiments, the port angle 1561 is about fifteen degrees to about eighty-five degrees. In one or more embodiments, the port angle 1561 is about forty-five degrees to about sixty degrees. In one or more embodiments, at least one of the shock wave emitting regions is about three millimeters (3 mm) to about six millimeters (6 mm) away from the central longitudinal axis in the extended configuration. In one or more embodiments, at least one of the shock wave emitting regions is closer to a wall of the enclosure than the central longitudinal axis in the extended configuration. In one embodiment, the at least one shock wave generating region is no less than one millimeter (1 mm) away from the enclosure wall in the extended configuration.

In some embodiments, a shock wave catheter includes at least one shock wave generating emitter movably connected to the elongated tube. In some embodiments, at least one shock wave generating emitter movably connected to the elongated tube such that, in a first configuration, the at least one emitter is in a first position and, in a second configuration, the at least one emitter is in a second position farther from the central longitudinal axis than in the first position. In some embodiments, the at least one emitter in the second position is no less than three millimeters (3 mm) farther from the central longitudinal axis than the first position. In other embodiments, the at least one emitter in the second position is no less than six millimeters (6 mm) farther from the central longitudinal axis in the second position, or no less than ten millimeters (10 mm) farther from the central longitudinal axis in the second position.

Figure 16:
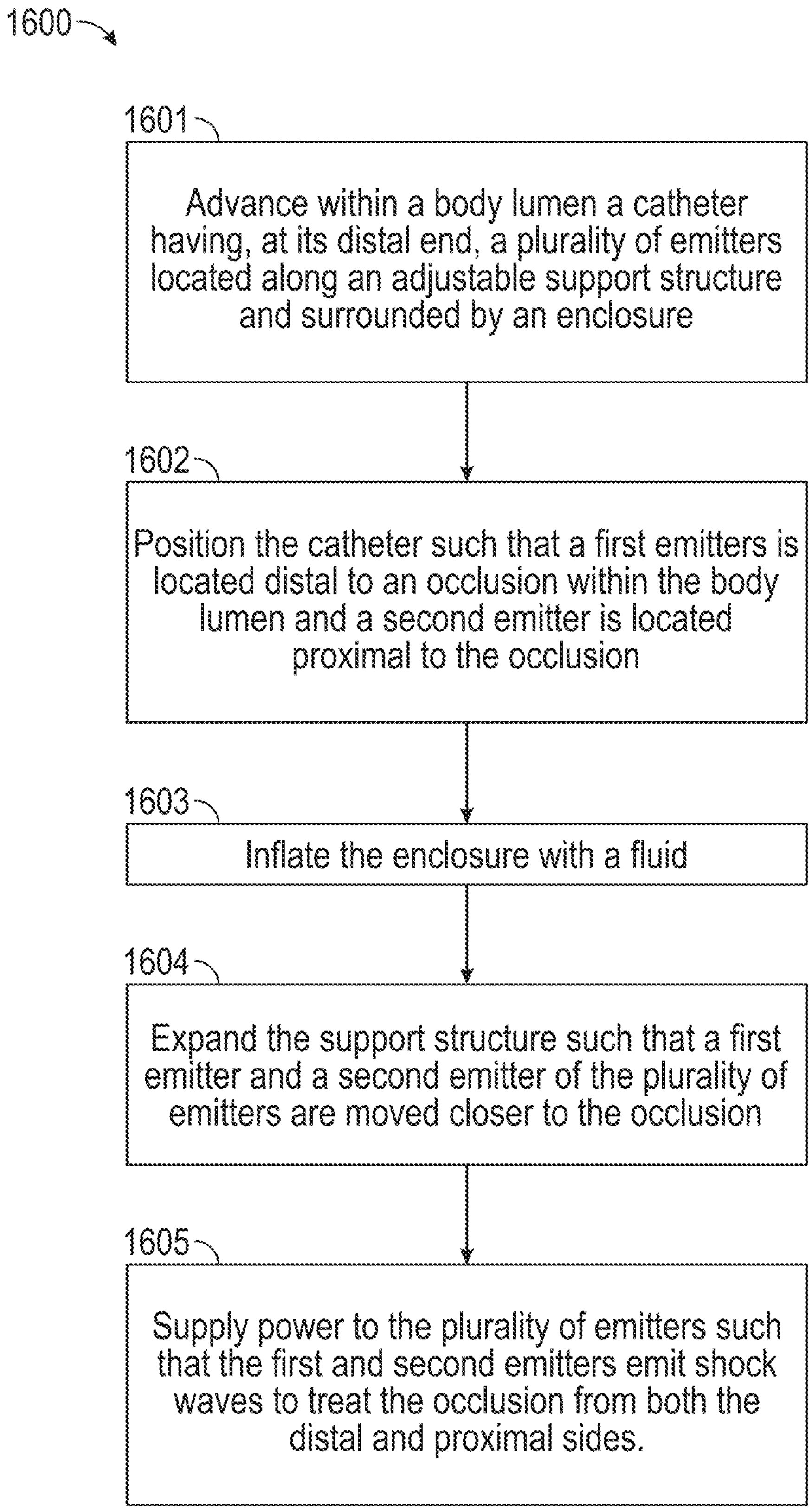
FIG. 16 illustrates a flowchart of an exemplary method of using a shock wave catheter having outwardly movable shock wave generating regions to treat an occlusion.

FIG. 16 illustrates an exemplary method of using a shock wave catheter having outwardly movable shock wave generating regions to treat an occlusion, such as any of the catheters described above, for example catheters 200B and 300A-C shown in respective FIGS. 3A-3B and FIGS. 6A-6C. At step 1601, a catheter is advanced within a body lumen. The catheter includes, at its distal end, a plurality of shock wave generating regions (e.g., emitters) located along an70djusttable support structure and surrounded by an enclosure. At step 1602, the catheter is positioned such that a first emitter is located distal to the occlusion (i.e., positioned between the occlusion and the distal end of the catheter) and a second emitter is located proximal to the occlusion (i.e., positioned between the occlusion and a proximal end of the catheter). At step 1603, the enclosure is filled and pressurized (e.g., to a pressure of about 2 atm-6 atm or up to about 4 atm). At step 1604, the support structure is expanded such that first and second emitters of the plurality of emitters are positioned laterally away from the elongated tube of the catheter and closer to the occlusion. In some embodiments, expanding the support structure also moves the first and second emitters longitudinally closer to the occlusion (and each other). At step 1605, power is supplied to the plurality of emitters such that the first and second emitters emit shock waves to treat the occlusion from both the distal and proximal sides of the occlusion. In some embodiments, the first and second shock wave generating emitters are supplied with power such that shock waves are generated from the first and second emitters at substantially the same time. In some embodiments, each of the first and second shock wave generating emitters comprise a pair of electrodes and supplying power to the emitters includes applying a voltage across each electrode pair. Method 1600 may be particularly useful for treating eccentric lesions. Method 1600 may be implemented, e.g., by the embodiments shown in FIGS. 3A and 3B and FIGS. 6A, 6B, and 6C and described above.

Figure 17:
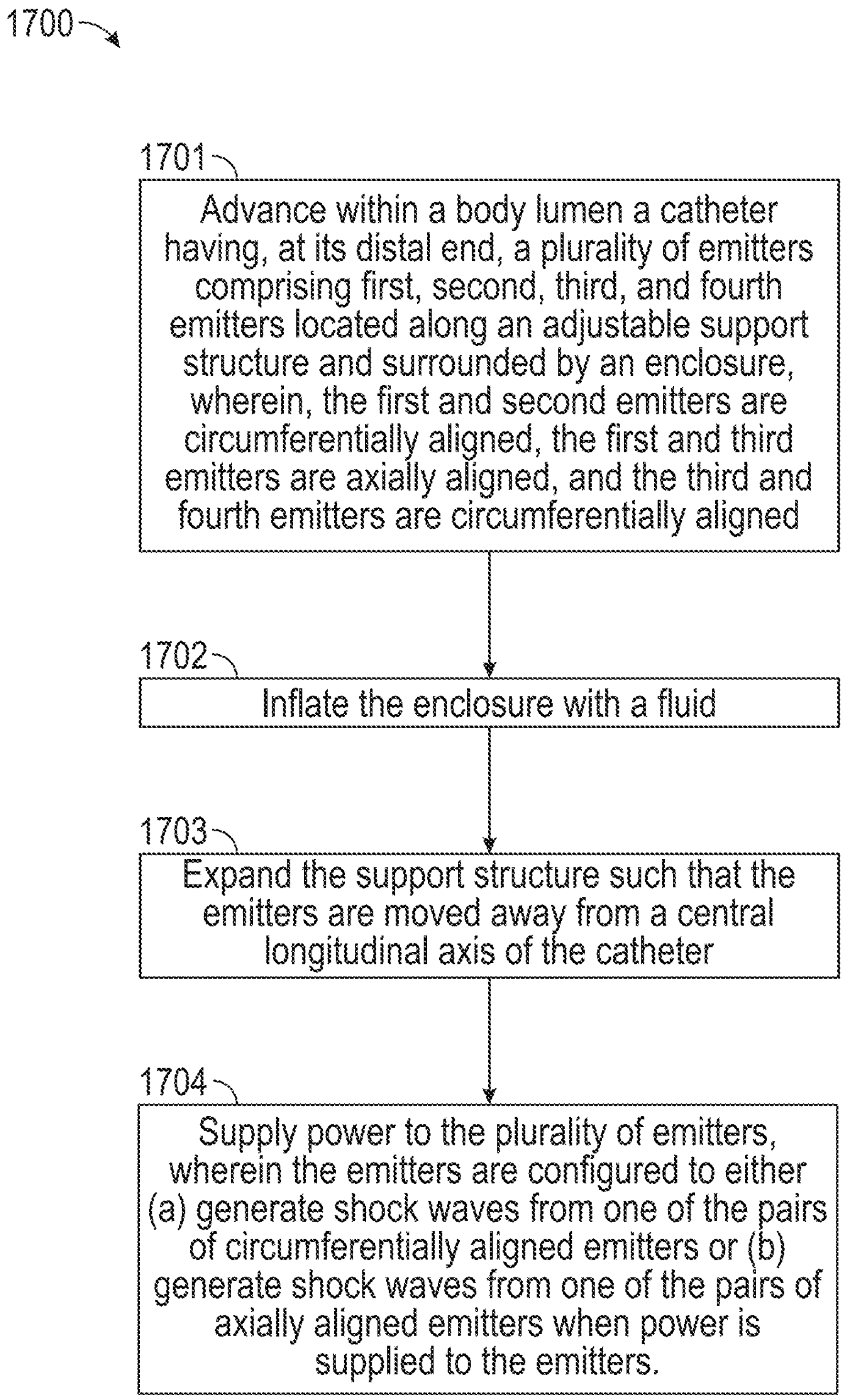
FIG. 17 illustrates a flowchart of another exemplary method of using a shock wave catheter having outwardly movable shock wave generating regions to treat an occlusion.

FIG. 17 illustrates another exemplary method of using a shock wave catheter having outwardly movable shock wave generating regions to treat an occlusion, such as any of the catheters described above, for example catheters 200B and 300A-C shown in respective FIGS. 3A-3B and FIGS. 6A-6C. At step 1701, a catheter having, at its distal end, a plurality of shock wave generating regions comprising first, second, third, and fourth shock wave generating regions is advanced within a body lumen. The catheter may bac advanced such that the first emitter is located distal to the lesion and the second emitter is located proximal to the lesion. The shock wave generating regions may be located on an adjustable support structure and surrounded by an enclosure (e.g., an angioplasty balloon). The support structure may be configured to expand laterally relative to a central longitudinal axis of the elongated tube to move the first, second, third, and fourth emitters farther from the central longitudinal axis. The first and second shock wave generating regions are circumferentially aligned and axially spaced apart. The first and third shock wave generating regions are axially aligned. The third emitter is circumferentially offset form the second emitter. The third and fourth shock wave generating regions are circumferentially aligned. The fourth shock wave emitter is axially aligned with the second emitter. At step 1702, the enclosure is filled with a fluid (e.g., to a pressure of about 2 atm-6 atm or about 4 atm). In some embodiments, the enclosure is inflated with a fluid, such as a conductive fluid. At step 1703, the support structure is expanded such that the shock wave generating regions are moved laterally away from a central longitudinal axis of the catheter. In some embodiments, moving the first and second emitters laterally away from the elongated tube moves the first and second emitters closer to each other (e.g., to promote constructive interference between shock waves generated at the emitters in order to increase the shock wave energy delivered to a lesion). At step 1704, power is supplied to the plurality of shock wave generating regions. The shock wave generating regions are configured to either (a) generate shock waves from one of the pairs of circumferentially aligned shock wave generating regions or (b) generate shock waves from one of the pairs of axially aligned shock wave generating regions when power is supplied. It may be advantageous to sync the pulsing of circumferentially aligned shock wave generating regions to treat eccentric lesions (i.e., from distal and proximal sides of the lesion). It may be advantageous to sync the pulsing of axially aligned shock wave generating regions to treat relatively large vessels (e.g., carotid artery). In some examples, supplying power to the emitter assembly includes supplying power to the first and second emitters to cause the first and second emitters to generate shock waves at substantially the same time.

Figure 18A:
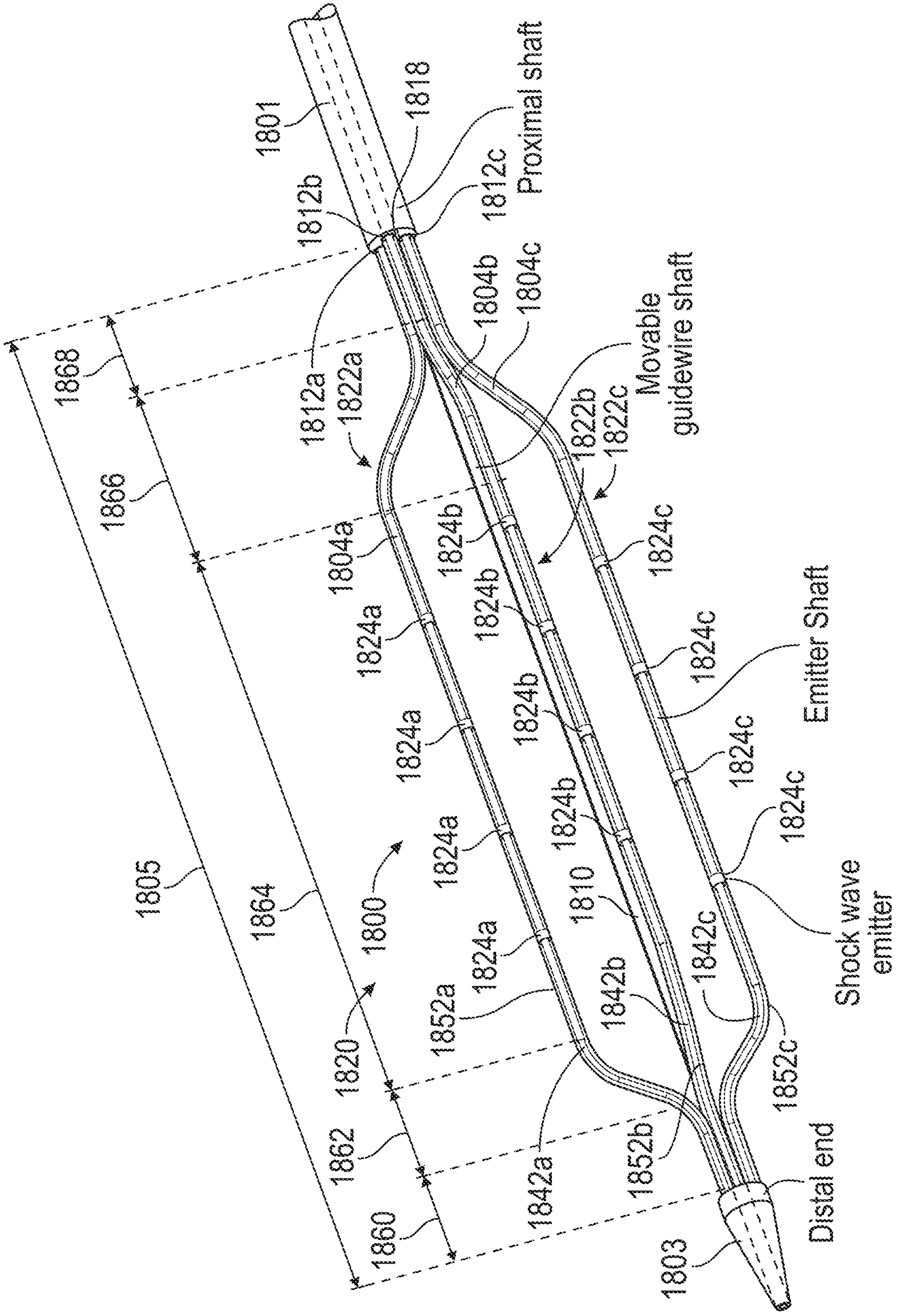
FIG. 18A illustrates an exemplary shock wave catheter having a laterally expandable structure in an expanded configuration according to some examples.
Figure 18B:
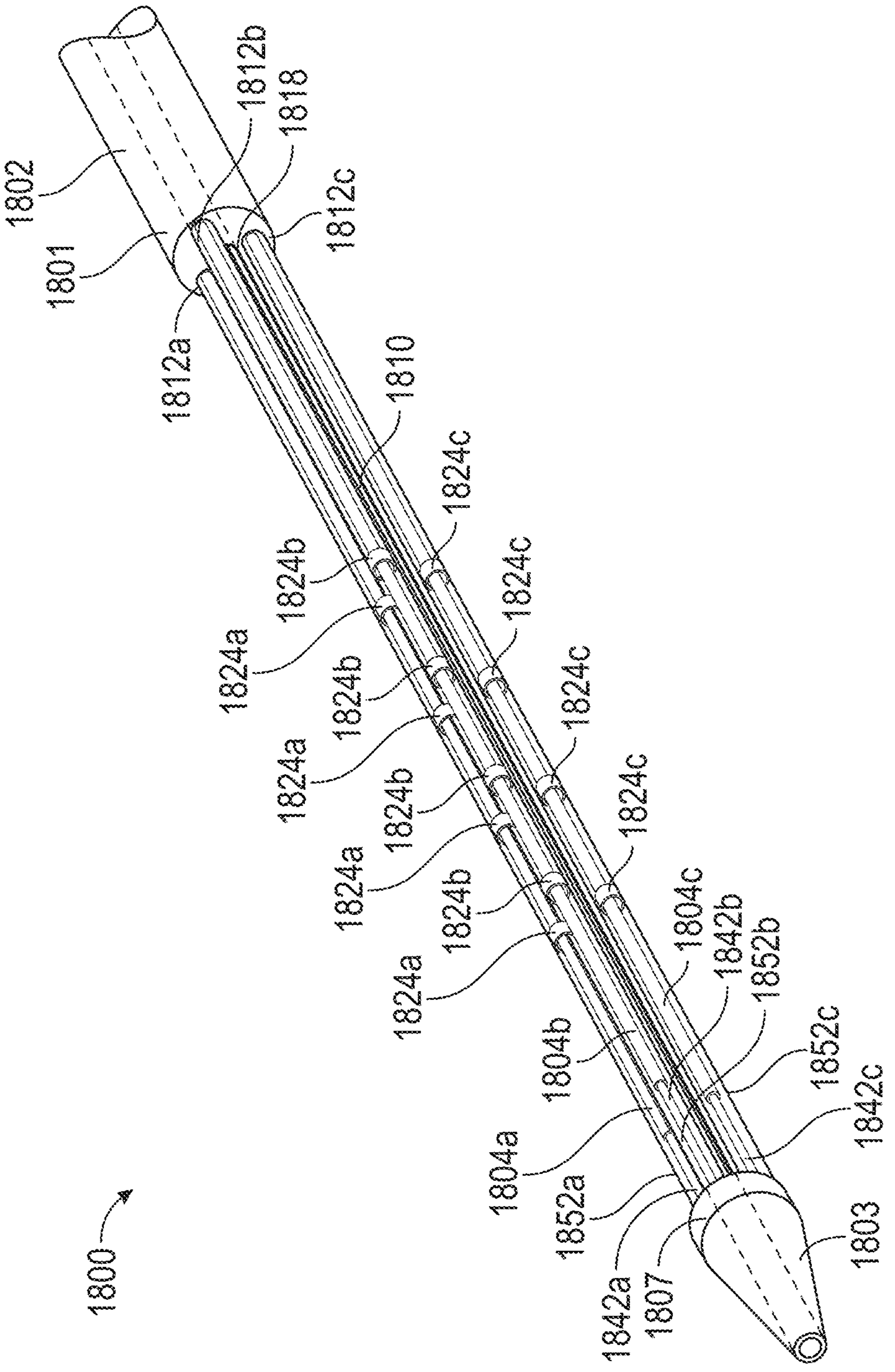
FIG. 18B illustrates the exemplary shock wave catheter of FIG. 18A in a collapsed configuration according to some examples.

FIGS. 18A and 18B illustrate an exemplary catheter 1800 having laterally movable shock wave emitters configured to enable a user to vary the distance between a shock wave emitter and a lesion. Catheter 1800 is further configured to enable fluid (e.g., blood) to flow around the catheter 1800 during shock wave treatment. Catheter 1800 includes a catheter body 1801 and a laterally (e.g., radially) expandable structure 1820 positioned at a distal emitter region 1805 of the catheter 1800. FIG. 18A illustrates the expandable structure 1820 in an expanded configuration, and FIG. 18B illustrates the expandable structure 1820 in a collapsed position. During treatment, the catheter 1800 may be advanced through a body lumen to a lesion within the body lumen. The expandable structure 1820 may be expanded to an expanded configuration such that a plurality of shock wave emitter assemblies 1824*a*-1824*c* positioned on a plurality of expandable emitter supports 1822*a*-1822*c* are positioned closer to a lesion relative to when the expandable structure 1820 is in a collapsed configuration. A gap (e.g., channel) may be maintained between each of the respective expandable emitter supports 1822*a*-1822*c* in the expanded configuration such that fluid can flow around the catheter 1800 and past emitter supports 1822*a*-1822*c*. While FIGS. 18A and 18B depict an example of an expandable structure 1820 having three emitter supports 1822*a*-1822*c*, it should be understood that the expandable structure 1820 could include any number of emitter supports 1822*a*-1822*c*.

The expandable structure 1820 may be movable between the expanded configuration shown in FIG. 18A and the collapsed configuration shown in FIG. 18B using a movable shaft 1810 connected to the expandable structure 1820. In some examples, moving the movable shaft 1810 proximally relative to the expandable structure 1820, toward a proximal portion of the catheter, may cause the expandable structure 1820 to expand laterally and moving the movable shaft 1810 distally relative to the expandable structure 1820, toward a distal portion of the catheter, may cause the expandable structure 1820 to compress laterally, as shown in FIG. 18B. Thus, in a laterally collapsed configuration of the expandable structure 1820, the movable shaft 1810, may be in a proximal position. In a laterally expanded configuration of the expandable structure, the movable shaft may be in a distal position. It should be understood that other structures to allow lateral expansion or compression of the expandable structure 1820 are possible. For example, bending regions of the expandable structure may be formed of a shape memory material such as nitinol and configured to bend when exposed in a body lumen to an external stimulus such as a temperature change, pH change, etc. Additionally, while the emitter supports 1822*a*-1822*c* are shown in FIGS. 18A and 18B as extending into separate lumens 1812*a*-1812*c*, in some examples, the expandable emitter supports 1822*a*-1822*c* may extend together through a single lumen of the catheter body 1801.

In some examples, the catheter body 1801 may have a central lumen 1818 extending along the catheter body 1801. The movable shaft 1810 may extend proximally from a distal end member 1803 positioned distally of the distal emitter region 1805 through the catheter body 1801 to the proximal portion of the catheter 1800 via central lumen 1818. The movable shaft 1810, at the distal emitter region, may define a central longitudinal axis and the distance of the emitter supports 1822*a*-1822*c* from the central axis may be adjustable to move the shock wave emitter assemblies 1824*a*-1824*c* closer to a site of a lesion. For instance, the movable shaft 1810 may be movable (e.g., longitudinally slidable distally and proximally) within the central lumen 1818 relative to the expandable emitter supports 1822*a*-1822*c*. The movable shaft 1810 may be connected to the distal end member 1803 such that proximal or distal movement of the movable shaft 1810 results in corresponding proximal or distal movement of the distal end member 1803. The expandable emitter supports 1822*a*-1822*c* may extend from the distal emitter region 1805 distally to the distal end member 1803 and proximally through the catheter body 1801 to a proximal portion of the catheter (e.g., to a hub or handle) via the plurality of lumens 1812*a*-1812*c*. The expandable emitter supports 1822*a*-1822*c* may be fixedly connected to both the distal end member 1803 and to the plurality of lumens 1812*a*-1812*c* of the catheter body 1801. Applying an axial force to the movable shaft 1810 may cause the expandable structure 1820 to collapse and expand with the movement of the movable shaft 1810 and distal end member 1803 because of the connection between the expandable emitter supports 1822*a*-1822*c* with the distal end member 1803 and the plurality of lumens 1812*a*-1812*c* of the catheter body 1801.

In some examples, the expandable emitter supports 1822*a*-1822*c* may each include an outer elongate member 1852*a*-1852*c* and an inner elongate member 1804*a*-1804*c*. The outer elongate members 1852*a*-1852*c* may be enclosures that enclose the one or more shock wave emitter assemblies 1824*a*-1824*c* positioned on the expandable emitter supports 1822*a*-1822*c*. In some examples, the outer elongate members 1852*a*-1852*c* may be flexible (but not inflatable) tubes configured to bend when the expanded structure 1820 is positioned in the expanded configuration. In some examples, the outer elongate members 1852*a*-1852*c* may be inflatable balloons. The expandable structure 1820 and emitter supports 1822*a*-1822*c* may be configured to be expanded such that the outer elongate members 1852*a*-1852*c* are in contact with an inner wall of a body lumen and/or lesion within the lumen.

In some examples, when in the expanded configuration, a portion of the emitter supports 1822*a*-1822*c* are positioned such that a gap is formed between each of the outer elongate members 1852*a*-1852*c*, allowing blood to flow through the expandable structure 1820 and enabling longer treatment procedures than would be possible with a conventional angioplasty balloon that fully occludes the vessel being treated. In some examples, the expandable structure 1820 may be biased toward the collapsed position shown in FIG. 18B. The catheter 1800 may be advanced within a body lumen while the expandable structure 1820 is in a collapsed state. Once the catheter is positioned such that the shock wave emitter assemblies 1824*a*-1824*c* are in a desired location (e.g., adjacent to a lesion), expandable support structure 1820 can be expanded to move the shock wave emitter assemblies 1824*a*-1824*c* relatively closer to the lesion.

The one or more shock wave emitter assemblies 1824*a*-1824*c* may be positioned on each of the inner elongate members 1804*a*-1804*c*. The inner elongate members may be elongate shafts (e.g., tubes). In some examples, each of the inner elongate members 1804*a*-1804*c* may include a lumen extending along the length of the respective inner elongate members 1804*a*-1804*c*. In some examples, a respective core elongate member 1842*a*-1842*c* may be positioned within the lumen of each of the inner elongate members 1804*a*-1804*c*. The core elongate members 1842*a*-1842*c* may comprise a shape memory material (e.g., Nitinol) and may extend from distal end member 1803 to the catheter body 1801.

In some examples, the outer elongate members 1852*a*-1852*c* may include a thermoplastic polyurethane having a Shore A hardness 80-100. The inner elongate members 1804*a*-1804*c* may include a high density polyethylene having a density greater than 0.9 g/cc. The core elongate members 1842*a*-1842*c* may include a thermoplastic elastomer and/or a polyether block amide.

In some examples, the expandable emitter supports 1822*a*-1822*c* each include a proximal region 1868 that extends distally from the catheter body 1801 to a first transition region 1866. The transition region 1866 may extend distally from the proximal region 1868 to a central region 1864, which may in turn extend distally to a second transition region 1862. The second transition region 1862 may extend distally from the central region 1864 to a distal region 1860 that extends from the transition region 1862 to the distal end member 1803. The central region 1864 may be configured such that it remains parallel to the central longitudinal axis defined by movable shaft 1810 in both the collapsed configuration (shown in FIG. 18B) and the expanded configuration (shown in FIG. 18A).

In some examples, the first and second transition regions 1866 and 1862 include bending or hinging regions that enable the expandable emitter supports 1822*a*-1822*c* to expand outwardly away from the central longitudinal axis. The bending or hinging regions may be configured to bend in response to the movable shaft 1810 being pushed proximally or distally. In some examples, the bending or hinging regions include a plurality of hinges (e.g., living hinges). In some examples, transition region 1866 includes a first bending region at a proximal end portion of the transition region 1866 and a second bending region at a distal end portion of the transition region 1866. In some examples, transition region 1862 includes a first bending region at a proximal end portion of the transition region 1862 and a second bending region at a distal end portion of the transition region 1862. When in the expanded configuration, first and second bending regions (of both the first transition region 1866 and second transition region 1862) may form arcuate shapes facing in opposing directions and connected by a central portion of the respective transition regions. Thus, in some examples, the transition regions 1866 and 1862 may form "s" or "zigzag" shapes in the expanded configuration. In some examples, the outer elongate members 1852*a*-1852*c* may be relatively thinner at the respective bending regions compared to the central regions. The relatively thinner portion of the outer elongate members 1852*a*-1852*c* at the bending regions may enable the expandable support structure to transition between the collapsed and expanded configurations more easily relative to a structure having a constant thickness. The bending regions may include a material having superelastic properties, such as nickel titanium (nitinol). The bending regions may be treated (e.g., by heat-treatment) to conform to a bent configuration in response to application of a longitudinal force and to return to a substantially straight configuration when the longitudinal force is removed. In some examples, one or more of the expandable emitter supports 1822*a*-1822*c* may instead form a continuous arcuate shape when in the expanded configuration. In such examples, the one or more expandable emitter supports 1822*a*-1822*c* may not include discrete bending or hinging regions.

The outer elongate members 1852*a*-1852*c* may each be fluidically connected to a fluid source and configured to be filled with a conductive fluid. The outer elongate members 1852*a*-1852*c* may be configured such that, when filled with a conductive fluid, the outer elongate members 1852*a*-1852*c* do not inflate, or inflate only minimally, such that the size of the gap between each of the outer elongate members 1852*a*-1852*c* remains relatively constant in the expanded configuration whether the outer elongate members 1852*a*-1852*c* are filled or not filled. In some examples, when filled with a conductive fluid, an outer diameter of the outer elongate members 1852*a*-1852*c* may expand by at most 1 millimeter (1 mm) when filled and pressurized to a working pressure of up to 4 atmospheres (4 atm).

In some examples, an outer diameter of the outer elongate members 1852*a*-1852*c* is constant along the entire length of the outer elongate members 1852*a*-1852*c*. In some examples, an outer diameter of the outer elongate members 1852*a*-1852*c* is constant along the length of the outer elongate members 1852*a*-1852*c* within the distal emitter region 1805. In some examples, each emitter support 1822*a*-1822*c*, at the distal emitter region 1805, may include an outer diameter of between 0.03 inches and 0.06 inches (e.g., 0.048 inches). In some examples, each outer elongate member may have a wall thickness of between 0.001 inches and 0.005 inches (e.g., 0.002 inches). As shown in the collapsed configuration depicted in FIG. 18B, the catheter body may have a proximal outer diameter 1802 that is equal to or larger than the maximum width of the expandable structure 1820 when the expandable structure 1820 is in the collapsed configuration. The distal end member 1803 may include a distal outer diameter 1807. The expandable structure 1820 may have a maximum width in the collapsed configuration less than or equal to the proximal outer diameter 1807. When in the expanded configuration, however, the expandable structure 1820 may have a maximum width that exceeds both proximal diameter 1802 and distal diameter 1803. At the distal emitter region 1805, the catheter 1800 may have a maximum expanded diameter in a laterally expanded configuration and a collapsed diameter in a laterally collapsed configuration. The maximum expanded diameter may be greater than the collapsed diameter by 0.2 inch to 1.0 inch (e.g., 0.7 inch).

Figure 19:
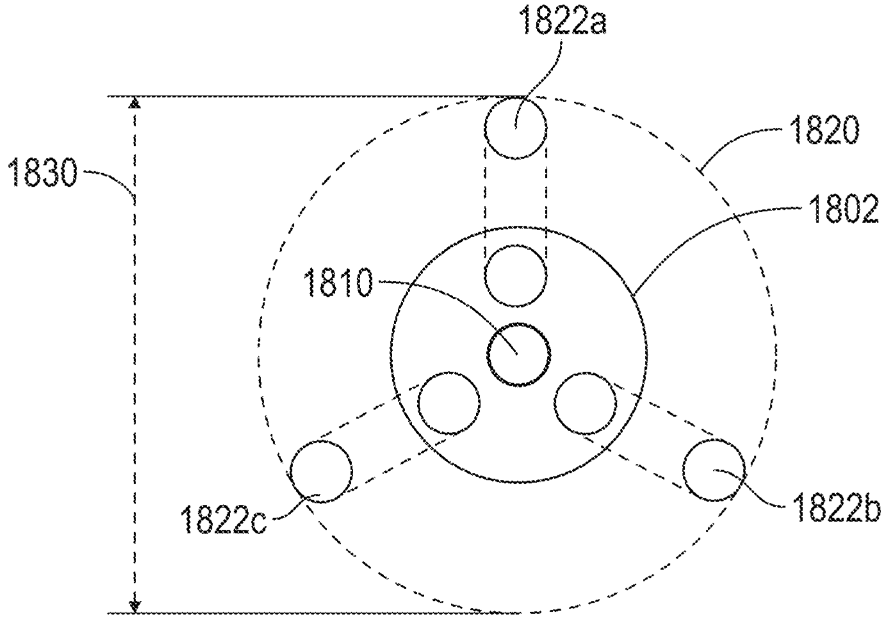
FIG. 19 illustrates a front cross-section view of the catheter of FIGS. 18A-18B in an expanded configuration according to some examples.

FIG. 19 illustrates a cross-sectional front view of the distal emitter region 1805 of catheter 1800 depicted in FIGS. 18A and 18B in an expanded configuration. In the expanded configuration depicted in FIG. 19, the catheter 1800 has an expanded maximum width w labeled 1830. The catheter 1800 has an expanded footprint FP, labeled 1820, in the expanded configuration that can be determined according to the following equation: $FP=\pi(w/2)^2$. The proximal diameter 1802 of the catheter 1800 described above may have a cross-sectional area equal to less than 50% of the expanded footprint FP. In some examples, the expanded configuration is sized to treat iliac artery disease and/or structural heart disease.

Returning to FIGS. 18A and 18B, the shock wave emitter assemblies 1824*a*-1824*c* may include at least one shock wave emitter that includes at least one electrode pair. The shock wave emitter assemblies 1824*a*-1824*c* a shock wave emitter that includes a distal end of an optical fiber. In the case of electrohydraulically generated shock waves, each emitter includes an electrode pair having a first electrode and a second electrode separated by a spark gap, where each electrode of the electrode pair is electrically connected (e.g., by wires that extend along a length of the catheter body) to a power source. Electrode pairs along an emitter shaft may be connected in series to each other. For embodiments including multiple emitter supports (e.g., 1822*a*-1822*c*), the electrode pairs along each emitter support 1822, 1822*b*, and 1822*c* may be connected in series to a single channel of the power generator. In some examples, electrode pairs along emitter supports 1822, 1822*b*, and 1822*c* may be connected to different channels of the power generator. In other embodiments, electrode pairs of different emitter supports 1822, 1822*b*, and 1822*c* may be connected in parallel from each other. In the case of light energy generated shock waves, an optical fiber extends from a light source (e.g., a laser) to the distal emitter region 1805 and light energy pulses generate shock waves at a distal end of the optical fiber.

Figure 20:
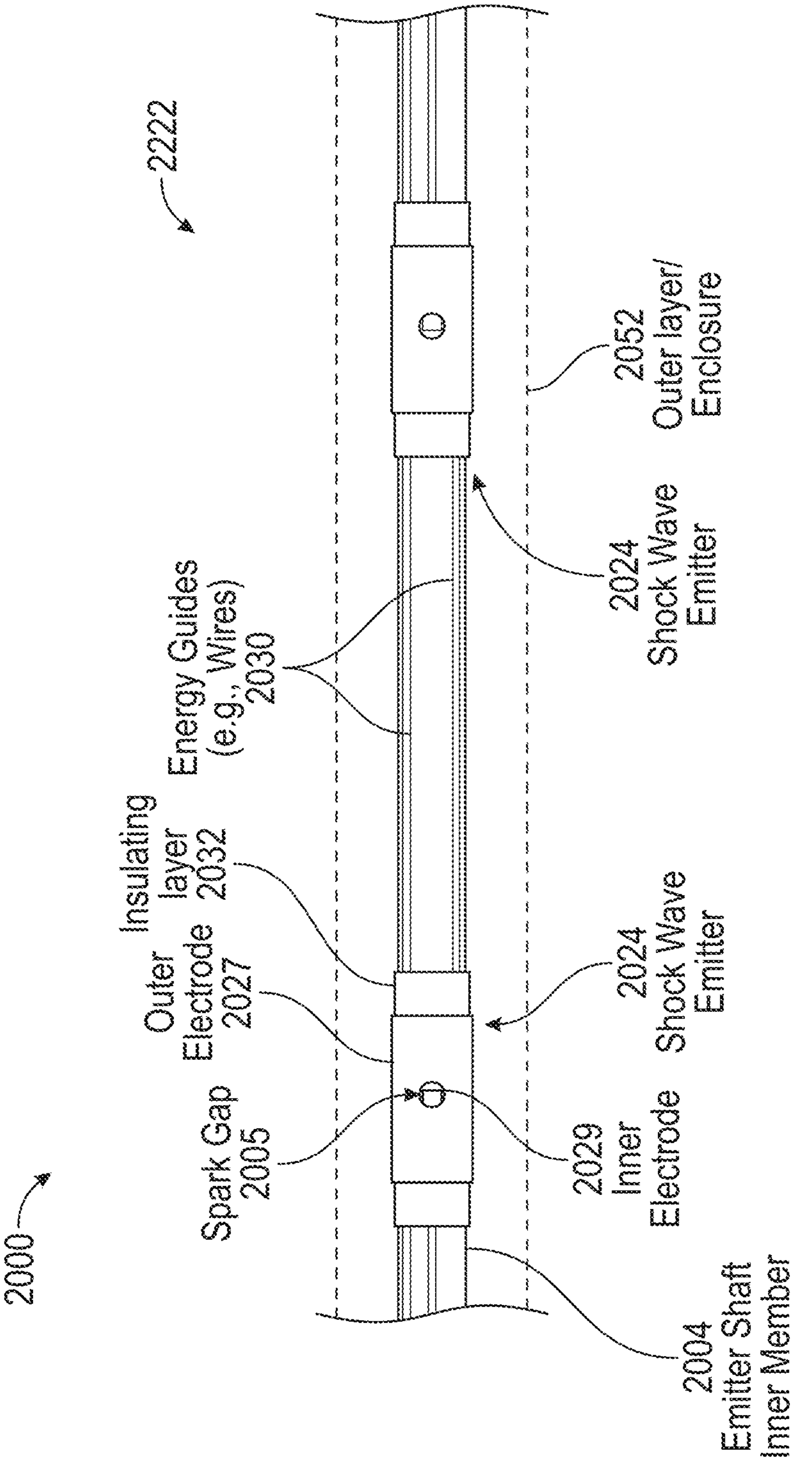
FIG. 20 illustrates a detailed view of exemplary shock wave emitter assemblies according to some examples.

FIG. 20 illustrates a detail view of shock wave emitter assemblies 2024 that may be used as any of the shock wave emitter assemblies 1824*a*-1824*c* of FIGS. 18A and 18B positioned on an emitter support 2022 of a catheter 2000 that may be used as any of the emitter supports 1822*a*-1822*c* of FIGS. 18A and 18B. As shown, multiple shock wave emitter assemblies 2024 may be positioned on emitter support 2022. Each emitter assembly may include an outer electrode 2027 and an inner electrode 2029 separated by a spark gap 2005. The outer electrode 2027 of each emitter assembly 2024 may be a conductive cylinder positioned on an elongate inner member of 2004 of emitter support 2022. In some examples, an insulating layer 2032 may be positioned between the respective outer electrodes 2027 and the inner elongate member 2004. In some examples, the inner electrode 2029 of each emitter assembly 2024 may be an exposed conductive portion of an energy guide 2030. In some examples, one or more of the energy guides 2030 may be wires that extend along at least a portion of inner elongate member 2004. One or more of the energy guides 2030 may extend from an energy source connected to a proximal portion of the catheter 2000 to the shock wave emitter assembly 2024.

An outer elongate member 2052 may enclose the shock wave emitter assemblies 2024. The outer elongate member 2052 may be an elongate cylindrical tube configured to be filled with a conductive fluid prior to and/or following shock wave generation. Unlike the balloon enclosures described above, the outer elongate member 2052 does not inflate to conform the diameter of a body lumen in which the catheter is inserted. An outer diameter of outer elongate member 2052 remains constant, or expands only minimally, when filled with a conductive fluid. The shock wave emitter assemblies 2024 may be positioned relatively closure to a lesion in a body lumen compared to conventions shock wave catheter configurations that utilize an inflatable balloon enclosure.

In some examples, the emitter assemblies 2024 are connected in series, such that power supplied by the power source (e.g., a voltage pulse) generates shock waves at each of the emitter assemblies 2024 as current flows across each spark gap 2005 between inner electrode 2029 and outer electrode 2027 of the respective emitter assembly 2024. In some examples, one or more of the emitter assemblies 2024 may be wired on a separate circuit or circuit branch, such that voltage pulses can be selectively applied to only a desired subset of emitters.

Various components and layers of the shock wave catheter may include polymeric materials. The polymeric materials may include one or more of thermoplastic polyurethanes (TPU), polyimides (PI), polytetrafluoroethanes (PTFE), polyether block amides (PEBA), and polyamides. Components that are configured to slide longitudinally against each other (e.g., the movable shaft 1810) may include materials that are relatively more lubricious, such as PTFE or a composite material including PTFE (e.g., a PI and PTFE composite material).

Figure 21:
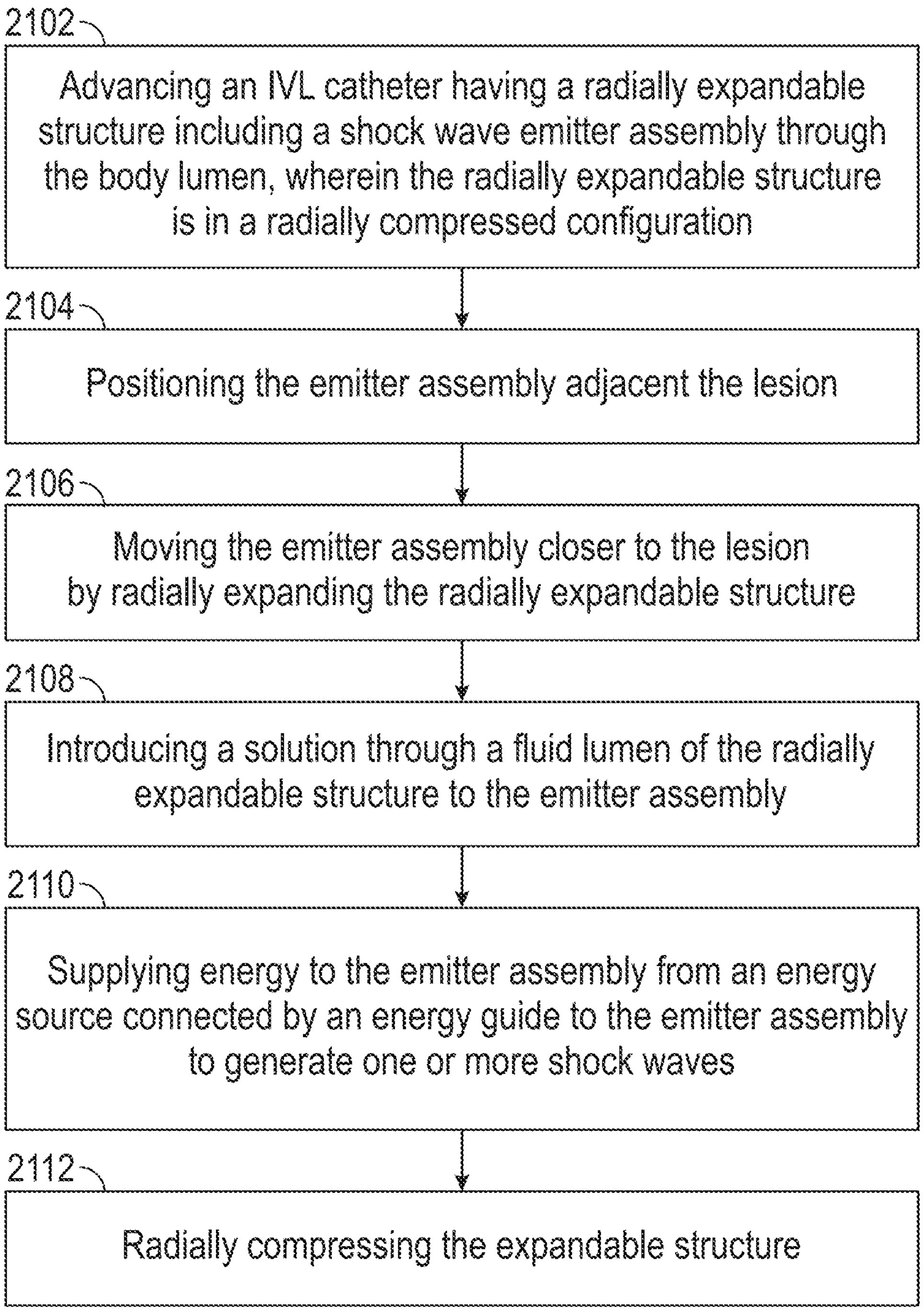
FIG. 21 illustrates a flowchart of an exemplary method for using a shock wave catheter having a laterally expandable structure.

FIG. 21 illustrates an exemplary method of treating a lesion in a body lumen. At block 2102 the method includes advancing an IVL catheter having a laterally expandable structure including a shock wave emitter assembly through the body lumen. The laterally expandable structure may be in a laterally collapsed configuration while the catheter is advanced within the body lumen. The catheter may include any of the features described with respect to the exemplary catheters disclosed herein. At block 2104, the method includes positioning the emitter assembly adjacent to the lesion. The emitter assembly may be advanced within the body lumen until one or more shock wave emitters are positioned at a location within the body lumen longitudinally aligned with the lesion.

At block 2106, the method includes moving the emitter assembly closer to the lesion by laterally expanding the laterally expandable structure. The laterally expandable structure may be expanded according to any of the methods described herein. In some examples, laterally expanding the laterally expandable structure includes moving a movable shaft connected to the laterally expandable structure from a distal position to a proximal position or moving the movable shaft from a proximal position to a distal position. In some examples, moving the emitter assembly closer to the lesion by laterally expanding the laterally expandable structure forms a plurality of gaps between a plurality of components (e.g., emitter supports 1822*a*-1822*c*) of the laterally expandable structure. The plurality of gaps enable blood to flow past the IVL catheter when the laterally expandable structure is expanded.

At block 2108, the method includes introducing a solution through a fluid lumen of the laterally expandable structure to the emitter assembly. In some examples, introducing the solution includes evacuating air from the laterally expandable structure by pulling vacuum on the fluid lumen at a proximal end of the fluid lumen and replacing the vacuum with a fluid source to fill the laterally expandable structure with the solution. The solution may be a conductive fluid such as saline or contrast solution. The solution may fill an enclosure of the laterally expandable structure. The enclosure may be pressurized by the solution to a pressure not greater than 5 atm. In some examples, a pressure of the enclosure may be 1 atm-4 atm. The enclosure may enclose the emitter assembly positioned on the laterally expandable support structure. The enclosure may have a uniform outer diameter and may be configured such that it does not inflate or inflates only minimally in a uniform manner along the length of the enclosure when filled with the solution. In some examples, introducing the solution through the fluid lumen causes the enclosures to inflate by at most 1 millimeter (1 mm) when filled and pressurized to a working pressure of up to 4 atmospheres (4 atm).

At block 2110, the method includes supplying energy to the emitter assembly from an energy source connected by an energy guide to the emitter assembly to generate one or more shock waves. The energy source may be a voltage generator or a laser. In examples where the emitter assembly includes a pair of electrodes, the energy guide may be a wire or other conductive member for transmitting a current to the emitter assembly. In examples, where the emitter assembly includes an end (e.g., distal end) of an optical fiber, the energy guide may be an optical fiber for transmitting a laser pulse from the laser to the distal end of the optical fiber. At block 2112, the method may include laterally collapsing the expandable structure. The method may include advancing the catheter further within the lumen, expanding the expandable structure again, and generating one or more additional shockwaves.

Figure 22:
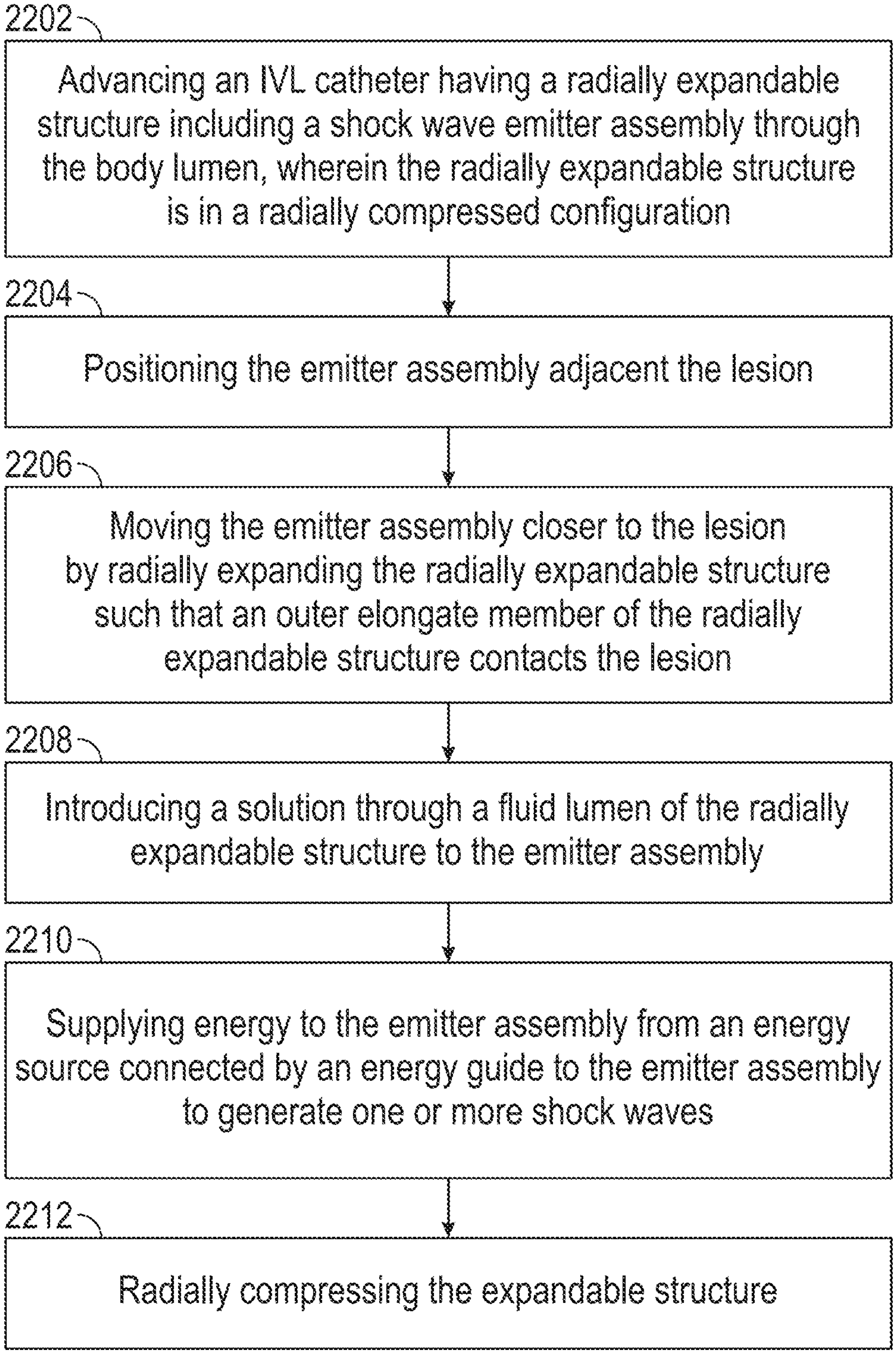
FIG. 22 illustrates a flowchart of another exemplary method for using a shock wave catheter having a laterally expandable structure.

FIG. 22 illustrates another exemplary method of treating a lesion in a body lumen in which an expandable structure is expanded such that an outer elongate member of a laterally expandable structure contacts the lesion. At block 2202, the method includes advancing an IVL catheter having a laterally expandable structure including a shock wave emitter assembly through the body lumen. The laterally expandable structure may be in a laterally collapsed configuration while the catheter is advanced within the body lumen. The catheter may include any of the features described with respect to the exemplary catheters disclosed herein. At block 2204, the method includes positioning the emitter assembly adjacent to the lesion. The emitter assembly may be advanced within the body lumen until one or more shock wave emitters are positioned at a location within the body lumen longitudinally aligned with the lesion.

At block 2206, the method includes moving the emitter assembly closer to the lesion by laterally expanding the laterally expandable structure such that an outer elongate member of the laterally expandable structure contacts the lesion. The laterally expandable structure may be expanded according to any of the methods described herein. In some examples, laterally expanding the expandable structure includes moving a movable shaft connected to the expandable structure from a distal position to a proximal position or moving the movable shaft from a proximal position to a distal position. In some examples, moving the emitter assembly closer to the lesion by laterally expanding the laterally expandable structure forms a plurality of gaps between a plurality of components (e.g., emitter supports 1822*a*-1822*c*) of the laterally expandable structure. The plurality of gaps enable blood to flow past the IVL catheter when the laterally expandable structure is expanded.

At block 2208, the method includes introducing a solution through a fluid lumen of the laterally expandable structure to the emitter assembly. In some examples, introducing the solution includes evacuating air from the laterally expandable structure by pulling vacuum on the fluid lumen at a proximal end of the fluid lumen and replacing the vacuum with a fluid source to fill the laterally expandable structure with the solution. The solution may be a conductive fluid such as saline or contrast solution. The solution may fill an enclosure of the laterally expandable structure. The enclosure may enclose the emitter assembly positioned on the laterally expandable structure. The enclosure may have a uniform outer diameter and may be configured such that it does not inflate or inflates only minimally in a uniform manner along the length of the enclosure when filled with the solution. In some examples, introducing the solution through the fluid lumen causes the enclosure to inflate by at most 1 millimeter (1 mm) when filled and pressurized to a working pressure of up to 4 atmospheres (4 atm).

At block 2210, the method includes supplying energy to the emitter assembly from an energy source connected by an energy guide to the emitter assembly to generate one or more shock waves. The energy source may be a voltage generator or a laser. In examples where the emitter assembly includes a pair of electrodes, the energy guide may be a wire or other conductive member for transmitting a current to the emitter assembly. In examples, where the emitter assembly includes an end (e.g., distal end) of an optical fiber, the energy guide may be an optical fiber for transmitting a laser pulse from the laser to the distal end of the optical fiber. At block 2212, the method may include laterally collapsing the expandable structure. The method may include advancing the catheter further within the lumen, expanding the expandable structure again, and generating one or more additional shockwaves.

Although the catheter devices and methods described herein have been discussed primarily in the context of treating coronary indications, such as lesions in vasculature, the catheter devices described herein can be used for a variety of indications. For instance, similar designs and methods could be used for treating soft tissues, such as cancer and tumors (i.e., non-thermal ablation methods), blood clots, fibroids, cysts, organs, scar and fibrotic tissue removal, or other tissue destruction and removal treatments. Catheter devices and methods could be used for neurostimulation treatments, targeted drug delivery, treatments of tumors in body lumens (e.g., tumors in blood vessels, the esophagus, intestines, stomach, or vagina), wound treatment, non-surgical removal, and destruction of tissue, or used in place of thermal treatments or cauterization for venous insufficiency and fallopian ligation (i.e., for permanent female contraception). In some examples, the catheters disclosed herein can be used to treat hardened tissue in the esophagus. The catheters described herein may be used for treating lumens in the car or nose, such as narrowed regions of lumens in the car or nose. The catheters disclosed herein may generate shock waves to break the bony structure in the narrowed region to restore proper drainage, while minimizing damage to soft tissues. Further, the catheter devices and methods described herein could also be used for tissue engineering methods, for instance, for mechanical tissue decellularization to create a bioactive scaffold in which new cells (e.g., exogenous and endogenous cells) can replace the old cells; introducing porosity to a site to improve cellular retention, cellular infiltration/migration, and diffusion of nutrients and signaling molecules to promote angiogenesis, cellular proliferation, and tissue regeneration similar to cell replacement therapy. Such tissue engineering methods may be useful for treating ischemic heart disease, fibrotic liver, fibrotic bowel, and traumatic spinal cord injury (SCI). For instance, for the treatment of spinal cord injury, the devices and assemblies described herein could facilitate the removal of scarred spinal cord tissue, which acts like a barrier for neuronal reconnection, before the injection of an anti-inflammatory hydrogel loaded with lentivirus to genetically engineer the spinal cord neurons to regenerate.

It should be noted that the elements and features of the example catheters illustrated throughout this specification and drawings may be rearranged, recombined, and modified without departing from the present disclosure. For instance, while this specification and drawings describe and illustrate catheters having several example balloon designs, the present disclosure is intended to include catheters having a variety of balloon configurations. The number, placement, and spacing of the electrode pairs of the shock wave emitters can be modified and the number, placement, and spacing of the enclosures of catheters can be modified without departing from the present disclosure.

It will be understood that the foregoing is only illustrative, and that various modifications, alterations and combinations can be made by those skilled in the art without departing from the scope and spirit of the disclosure. Any of the variations of the various catheters disclosed herein can include features described by any other catheters or combination of catheters herein. Furthermore, any of the methods can be used with any of the catheters disclosed. Accordingly, it is not intended that the systems, catheters, and methods described herein be limited, except as by the appended claims.

The invention claimed is:

1. A catheter for treating a lesion in a body lumen, the catheter comprising:
- an elongated tube;
- an enclosure sealed to a distal end of the elongated tube; and
- an emitter assembly disposed within the enclosure, the emitter assembly comprising:
  - at least one emitter configured to generate shock waves inside the enclosure when power is supplied to the at least one emitter;
  - a support structure supporting the at least one emitter, the support structure configured to expand outwardly relative to a central longitudinal axis of the elongated tube to move the at least one emitter farther from the central longitudinal axis, wherein the at least one emitter comprises a first emitter and a second emitter, and wherein lateral expansion of the support structure moves the first emitter and the second emitter laterally away from the longitudinal axis in opposing directions along a first plane intersecting the longitudinal axis; and
  - an elongate member that extends along the longitudinal axis through at least a portion of the support structure, wherein the support structure comprises one or more apertures and the elongate member extends through one or more of the apertures.

2. The catheter of claim 1, wherein the support structure comprises a plurality of segments connected by respective joints.

3. The catheter of claim 2, wherein the at least one emitter is mounted on the support structure proximate to one or more of the joints.

4. The catheter of claim 3, wherein the at least one emitter comprises a first emitter mounted proximate to a first joint of the support structure and a second emitter mounted proximate to a second joint of the support structure.

5. The catheter of claim 1, wherein movement of the elongate member in a proximal direction or a distal direction causes expansion of the support structure.

6. The catheter of claim 5, wherein a diameter of the support structure is controllable by moving the elongate member in the proximal direction or the distal direction.

7. The catheter of claim 6, wherein the elongate member includes one or more markings that indicate to a user an amount of movement of the elongate member associated with one or more expanded diameters of the support structure.

8. The catheter of claim 5, wherein the support structure comprises a first stop and a second stop that are spaced apart in a collapsed state of the support structure and abutting in an expanded state of the support structure.

9. The catheter of claim 5, wherein the elongate member comprises a first tube and a second tube surrounding at least a portion of the first tube, and wherein movement of the first tube relative to the second tube causes expansion of the support structure.

10. The catheter of claim 1, wherein the support structure is expandable to a diameter of at least 5 mm.

11. The catheter of claim 1, wherein the support structure is expandable to a diameter of at least 1 cm.

12. The catheter of claim 1, wherein the at least one emitter is oriented to generate shock waves outwardly from the longitudinal axis.

13. The catheter of claim 8, wherein the elongate member is operably coupled to at least one of the first stop and the second stop such that movement of the elongate member moves the first stop relative to the second stop.

14. The catheter of claim 5, wherein the elongate member comprises a wire, and wherein movement of the wire in a proximal direction causes expansion of the support structure.

15. The catheter of claim 5, wherein moving the elongate member a predetermined distance causes the support structure to reversibly lock in an expanded state.

16. The catheter of claim 1, wherein, in a collapsed state, the support structure has a diameter less than 1 mm.

17. The catheter of claim 1, wherein the enclosure is an angioplasty balloon.

18. The catheter of claim 1, wherein the enclosure has an inflated diameter between 8 mm and 12 mm.

19. The catheter of claim 1, wherein the enclosure has an inflated diameter greater than 20 mm.

20. The catheter of claim 1, wherein the body lumen is a blood vessel or a valve.

21. The catheter of claim 1, wherein the support structure is formed of a resilient material selected from the group consisting of a metal or a polymeric material.

22. The catheter of claim 1, wherein, prior to expansion, the support structure is in a collapsed state, and after expansion of the support structure, the structure can return to substantially the same configuration in the collapsed state.

23. The catheter of claim 1, wherein material properties of the support structure bias the support structure in a collapsed state.

24. The catheter of claim 1, wherein material properties of the support structure bias the support structure in an expanded state.

25. The catheter of claim 1, further comprising one or more springs connected to a proximal end or a distal end of the support structure.

26. The catheter of claim 25, wherein the one or more springs are configured to bias the support structure in a collapsed state.

27. The catheter of claim 25, wherein the one or more springs are configured to bias the support structure in an expanded state.

28. The catheter of claim 1, the emitter assembly further comprising a first wire and a second wire, the first and second wires extending along at least a portion of the elongated tube and configured to apply a voltage to one or more of the at least one emitter such that a current is transmitted across at least one electrode pair of the at least one emitter.

29. The catheter of claim 1, wherein at least a portion of the support structure is conductive and configured to provide a voltage to the at least one emitter.

30. A catheter for treating a lesion in a body lumen, the catheter comprising:

an elongated tube;

an enclosure sealed to a distal end of the elongated tube; and an emitter assembly disposed within the enclosure, the emitter assembly comprising:

at least one emitter configured to generate shock waves inside the enclosure when power is supplied to the at least one emitter; and a support structure supporting the at least one emitter, the support structure configured to expand outwardly relative to a central longitudinal axis of the elongated tube to move the at least one emitter farther from the central longitudinal axis, wherein the support structure comprises a plurality of segments connected by respective joints.

31. The catheter of claim 30, wherein the at least one emitter is mounted on the support structure proximate to one or more of the joints.

32. The catheter of claim 31, wherein the at least one emitter comprises a first emitter mounted proximate to a first joint of the support structure and a second emitter mounted proximate to a second joint of the support structure.

33. The catheter of claim 30, wherein the support structure is expandable to a diameter of at least 5 mm.

34. The catheter of claim 30, wherein the support structure is expandable to a diameter of at least 1 cm.

35. The catheter of claim 30, wherein the at least one emitter is oriented to generate shock waves outwardly from the longitudinal axis.

36. The catheter of claim 30, wherein, in a collapsed state, the support structure has a diameter less than 1 mm.

37. The catheter of claim 30, wherein the enclosure has an inflated diameter between 8 mm and 12 mm.

38. The catheter of claim 30, wherein the enclosure has an inflated diameter greater than 20 mm.

39. The catheter of claim 30, wherein the support structure is formed of a resilient material selected from the group consisting of a metal or a polymeric material.

40. The catheter of claim 30, wherein, prior to expansion, the support structure is in a collapsed state, and after expansion of the support structure, the structure can return to substantially the same configuration in the collapsed state.

41. The catheter of claim 30, wherein material properties of the support structure bias the support structure in a collapsed state.

42. The catheter of claim 30, wherein material properties of the support structure bias the support structure in an expanded state.

43. The catheter of claim 30, the emitter assembly further comprising a first wire and a second wire, the first and second wires extending along at least a portion of the elongated tube and configured to apply a voltage to one or more of the at least one emitter such that a current is transmitted across at least one electrode pair of the at least one emitter.

44. The catheter of claim 30, wherein at least a portion of the support structure is conductive and configured to provide a voltage to the at least one emitter.

45. A catheter for treating a lesion in a body lumen, the catheter comprising:

an elongated tube;

an enclosure sealed to a distal end of the elongated tube; and an emitter assembly disposed within the enclosure, the emitter assembly comprising:

at least one emitter configured to generate shock waves inside the enclosure when power is supplied to the at least one emitter;

a support structure supporting the at least one emitter, the support structure configured to expand outwardly relative to a central longitudinal axis of the elongated tube to move the at least one emitter farther from the central longitudinal axis; and an elongate member that extends along the longitudinal axis through at least a portion of the support structure, wherein movement of the elongate member in a proximal direction or a distal direction causes expansion of the support structure.

46. The catheter of claim 45, wherein a diameter of the support structure is controllable by moving the elongate member in the proximal direction or the distal direction.

47. The catheter of claim 46, wherein the elongate member includes one or more markings that indicate to a user an amount of movement of the elongate member associated with one or more expanded diameters of the support structure.

48. The catheter of claim 45, wherein the support structure comprises a first stop and a second stop that are spaced apart in a collapsed state of the support structure and abutting in an expanded state of the support structure.

49. The catheter of claim 45, wherein the elongate member comprises a first tube and a second tube surrounding at least a portion of the first tube, and wherein movement of the first tube relative to the second tube causes expansion of the support structure.

50. The catheter of claim 45, wherein the support structure is expandable to a diameter of at least 5 mm.

51. The catheter of claim 45, wherein the support structure is expandable to a diameter of at least 1 cm.

52. The catheter of claim 45, wherein the at least one emitter is oriented to generate shock waves outwardly from the longitudinal axis.

53. The catheter of claim 45, wherein the support structure comprises one or more apertures and the elongate member extends through one or more of the apertures.

54. The catheter of claim 48, wherein the elongate member is operably coupled to at least one of the first stop and the second stop such that movement of the elongate member moves the first stop relative to the second stop.

55. The catheter of claim 45, wherein the elongate member comprises a wire, and wherein movement of the wire in a proximal direction causes expansion of the support structure.

56. The catheter of claim 45, wherein moving the elongate member a predetermined distance causes the support structure to reversibly lock in an expanded state.

57. The catheter of claim 45, wherein, in a collapsed state, the support structure has a diameter less than 1 mm.

58. The catheter of claim 45, wherein the enclosure has an inflated diameter between 8 mm and 12 mm.

59. The catheter of claim 45, wherein the enclosure has an inflated diameter greater than 20 mm.

60. The catheter of claim 45, wherein the support structure is formed of a resilient material selected from the group consisting of a metal or a polymeric material.

61. The catheter of claim 45, wherein, prior to expansion, the support structure is in a collapsed state, and after expansion of the support structure, the structure can return to substantially the same configuration in the collapsed state.

62. The catheter of claim 45, wherein material properties of the support structure bias the support structure in a collapsed state.

63. The catheter of claim 45, wherein material properties of the support structure bias the support structure in an expanded state.

64. The catheter of claim 45, the emitter assembly further comprising a first wire and a second wire, the first and second wires extending along at least a portion of the elongated tube and configured to apply a voltage to one or more of the at least one emitter such that a current is transmitted across at least one electrode pair of the at least one emitter.

65. The catheter of claim 45, wherein at least a portion of the support structure is conductive and configured to provide a voltage to the at least one emitter.

66. A catheter for treating a lesion in a body lumen, the catheter comprising:
- an elongated tube;
- an enclosure sealed to a distal end of the elongated tube; and
- an emitter assembly disposed within the enclosure, the emitter assembly comprising:
  - at least one emitter configured to generate shock waves inside the enclosure when power is supplied to the at least one emitter;
  - a support structure supporting the at least one emitter, the support structure configured to expand outwardly relative to a central longitudinal axis of the elongated tube to move the at least one emitter farther from the central longitudinal axis; and
  - one or more springs connected to a proximal end or a distal end of the support structure.

67. The catheter of claim 66, wherein the support structure is expandable to a diameter of at least 5 mm.

68. The catheter of claim 66, wherein the support structure is expandable to a diameter of at least 1 cm.

69. The catheter of claim 66, wherein the at least one emitter is oriented to generate shock waves outwardly from the longitudinal axis.

70. The catheter of claim 66, wherein, in a collapsed state, the support structure has a diameter less than 1 mm.

71. The catheter of claim 66, wherein the enclosure has an inflated diameter between 8 mm and 12 mm.

72. The catheter of claim 66, wherein the enclosure has an inflated diameter greater than 20 mm.

73. The catheter of claim 66, wherein the support structure is formed of a resilient material selected from the group consisting of a metal or a polymeric material.

74. The catheter of claim 66, wherein, prior to expansion, the support structure is in a collapsed state, and after expansion of the support structure, the structure can return to substantially the same configuration in the collapsed state.

75. The catheter of claim 66, wherein material properties of the support structure bias the support structure in a collapsed state.

76. The catheter of claim 66, wherein material properties of the support structure bias the support structure in an expanded state.

77. The catheter of claim 66, wherein the one or more springs are configured to bias the support structure in a collapsed state.

78. The catheter of claim 66, wherein the one or more springs are configured to bias the support structure in an expanded state.

79. The catheter of claim 66, the emitter assembly further comprising a first wire and a second wire, the first and second wires extending along at least a portion of the elongated tube and configured to apply a voltage to one or more of the at least one emitter such that a current is transmitted across at least one electrode pair of the at least one emitter.

80. The catheter of claim 66, wherein at least a portion of the support structure is conductive and configured to provide a voltage to the at least one emitter.

* * * * *